United States Patent
Haas et al.

(10) Patent No.: US 12,378,315 B2
(45) Date of Patent: Aug. 5, 2025

(54) ANTI-RABBIT CD19 ANTIBODIES AND METHODS OF USE

(71) Applicant: Hoffmann-La Roche Inc., Little Falls, NJ (US)

(72) Inventors: Alexander Haas, Penzberg (DE); Friederike Jung, Penzberg (DE); Stefan Klostermann, Penzberg (DE); Sonja Offner, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 961 days.

(21) Appl. No.: 17/362,126

(22) Filed: Jun. 29, 2021

(65) Prior Publication Data

US 2022/0135672 A1     May 5, 2022

Related U.S. Application Data

(63) Continuation of application No. PCT/EP2019/087064, filed on Dec. 27, 2019.

(30) Foreign Application Priority Data

Dec. 30, 2018   (EP) ................................. 18215920

(51) Int. Cl.
*C07K 16/28* (2006.01)
*C12N 5/0781* (2010.01)

(52) U.S. Cl.
CPC ........ *C07K 16/2803* (2013.01); *C12N 5/0635* (2013.01); *C07K 2317/24* (2013.01); *C12N 2500/80* (2013.01); *C12N 2502/30* (2013.01)

(58) Field of Classification Search
CPC ............ C07K 16/2803; C07K 2317/24; C07K 2317/33; C07K 2317/565; C12N 5/0635; C12N 2500/80; C12N 2502/30
See application file for complete search history.

(56) References Cited

U.S. PATENT DOCUMENTS

| | | | |
|---|---|---|---|
| 7,109,304 | B2 | 9/2006 | Hansen et al. |
| 2006/0233791 | A1 | 10/2006 | Tedder et al. |
| 2006/0257398 | A1 | 11/2006 | Hansen et al. |
| 2006/0280738 | A1 | 12/2006 | Tedder |
| 2008/0138336 | A1 | 12/2008 | Damschroder et al. |

FOREIGN PATENT DOCUMENTS

| | | | |
|---|---|---|---|
| EP | 1648512 A2 | 4/2006 | |
| EP | 1629012 B1 | 11/2018 | |
| WO | 03/048209 A1 | 6/2003 | |
| WO | 2004/106381 A1 | 12/2004 | |
| WO | 2005/012493 A1 | 2/2005 | |
| WO | 2006/089133 A2 | 8/2006 | |
| WO | 2006/121852 A2 | 11/2006 | |
| WO | 2006/133450 A2 | 12/2006 | |
| WO | 2007/002223 A2 | 1/2007 | |
| WO | 2008/022152 A2 | 2/2008 | |
| WO | 2011/147834 A1 | 12/2011 | |
| WO | 2011/147903 A1 | 12/2011 | |
| WO | 2013/076139 A1 | 5/2013 | |
| WO | 2016/092315 A1 | 6/2016 | |
| WO | 2017/055541 A1 | 4/2017 | |
| WO | 2017/0136807 A1 | 8/2017 | |
| WO | 2017/195749 A1 | 11/2017 | |

OTHER PUBLICATIONS

Bejcek, B., et al., "Development and Characterization of Three Recombinant Single Chain Antibody Fragments (scFvs) Directed against the CD19 Antigen" Cancer Res 55(11):2346-2351 (Jun. 1, 1995).
Bruenke, J., et al., "Effective lysis of lymphoma cells with a stabilised bispecific single-chain Fv antibody against CD19 and FcγRIII (CD16)" BR J Haematol 130(2):218-228 (Jul. 1, 2005).
Carter, R., et al., "Roles of CD19 Signal Transduction in B Cell Biology" Immunol Res 26(1-3):45-54 (Aug. 1, 2002).
Eberl, G., et al., "An anti-CD19 antibody coupled to a tetanus toxin peptide induces efficient Fas ligand (FasL)-mediated cytotoxicity of a transformed human B cell line by specific CD4+ T cells" Clin Exp Immunol 114(2):173-178 (Nov. 1, 1998).
Ghetie, M. A., et al., "An anti-CD19 antibody inhibits the interaction between P-glycoprotein (P-gp) and CD19, causes P-gp to translocate out of lipid rafts, and chemosensitizes a multidrug-resistant (MDR) lymphoma cell line" BLOOD 104(1):178-183 (Jul. 1, 2004).
Haagen, I.A., et al., "The efficacy of CD3 x CD19 bispecific monoclonal antibody (BsAb) in a clonogenic assay: the effect of repeated addition of BsAb and interleukin-2" Blood 85(11):3208-3212 (Jun. 1, 1995).
"International Preliminary Report on Patentability—PCT/EP2019/087064" (Report Issuance Date: Jun. 16, 2021; Chapter I), :pp. 1-8 (Jul. 15, 2021).
"International Search Report—PCT/EP2019/087064" (w/Written Opinion), :pp. 1-15 (Apr. 20, 2020).
Lang, P., et al., "Chimeric CD19 antibody mediates cytotoxic activity against leukemic blasts with effector cells from pediatric patients who received T-cell-depleted allografts" Blood 103(10):3982-3985 (May 15, 2004).
Le Gall, F., et al., "Di-, tri-and tetrameric single chain Fv antibody fragments against human CD19: effect of valency on cell binding" FEBS LETT 453(1-2):164-168 (Jun. 18, 1999).
Lebien, T., et al., "B lymphocytes: how they develop and function" BLOOD 112(5):1570-1580 (Sep. 1, 2008).

(Continued)

*Primary Examiner* — Kimberly Ballard
*Assistant Examiner* — Stacey N MacFarlane
(74) *Attorney, Agent, or Firm* — Nicole M. Fortuné

(57) ABSTRACT

Herein is reported an antibody binding to rabbit CD19 comprising (a) a HVR-H1 comprising the amino acid sequence of SEQ ID NO: 32 or 33 or 34, (b) a HVR-H2 comprising the amino acid sequence of SEQ ID NO: 35 or 36, (c) a HVR-H3 comprising the amino acid sequence of SEQ ID NO: 37, (d) a HVR-L1 comprising the amino acid sequence of SEQ ID NO: 38, (e) a HVR-L2 comprising the amino acid sequence of SEQ ID NO: 39, and (f) a HVR-L3 comprising the amino acid sequence of SEQ ID NO: 40, as well as methods of using the same, especially in the identification and selection of antibody producing rabbit B-cells.

15 Claims, 11 Drawing Sheets

Figure 1A:
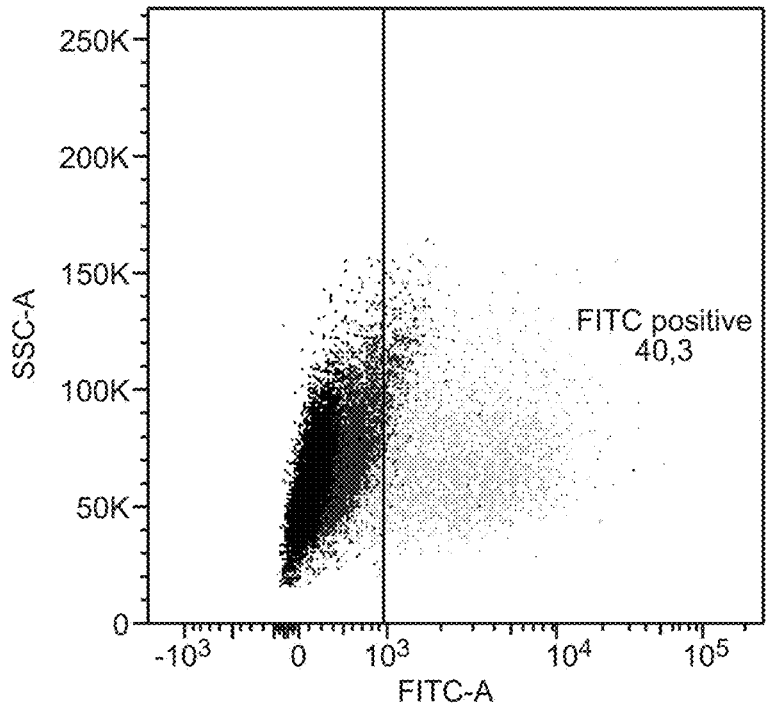

Specification includes a Sequence Listing.

(56) References Cited

OTHER PUBLICATIONS

Li, Q., et al., "Pharmacokinetics and biodistribution of radioimmunoconjugates of anti-CD19 Antibody and single-chain Fv for treatment of human B-cell malignancy" Cancer Immunol Immunother 47(3):121-130 (Nov. 1, 1998).

Loeffler, A., et al., "A recombinant bispecific single-chain antibody, CD19 x CD3, induces rapid and high lymphoma-directed cytotoxicity by unstimulated T lymphocytes" Blood 95(6):2098-2103 (Mar. 15, 2000).

Myers, D. E., et al., "Favorable pharmacodynamic features and superior anti-leukemic activity of B43 (anti-CD19) immunotoxins containing two pokeweed antiviral protein molecules covalently linked to each monoclonal antibody molecule" Leuk Lymphoma 18(1-2):93-102 (Jun. 1, 1995).

Pezzutto, A., et al., "CD19 monoclonal antibody HD37 inhibits anti-immunoglobulin-induced B cell activation and proliferation" J Immunol 138(9):2793-2799 (May 1, 1987).

Pietersz, G.A., et al., "In vitro and in vivo antitumor activity of a chimeric anti-CD19 antibody" Cancer Immunol Immunother 41(1):53-60 (Jul. 1, 1995).

Rhodes, E.G., et al., "A method for clinical purging of myeloma bone marrow using peanut agglutinin as an anti-plasma cell agent, in combination with CD19 monoclonal antibody" Bone Marrow Transplant 10(6):485-489 (Dec. 1, 1992).

Starkie, D., et al., "Generation of Recombinant Monoclonal Antibodies from Immunised Mice and Rabbits via Flow Cytometry and Sorting of Antigen-Specific IgG+ Memory B Cells" PLOS ONE 11(3):e0152282 (1-26) (Mar. 29, 2016).

Tedder, T.F., "CD19: a promising B cell target for rheumatoid arthritis" Nat Rev Rheumatol 5(10):572-577 (Oct. 1, 2019).

Uckun, F.M., et al., "Detailed studies on expression and function of CD19 surface determinant by using B43 monoclonal antibody and the clinical potential of anti-CD19 immunotoxins" Blood 71(1):13-29 (Jan. 1, 1988).

Vallera, D.A., et al., "Radiotherapy of CD19 expressing Daudi tumors in nude mice with Yttrium-90-labeled anti-CD19 antibody" Cancer Biother Radiopharm 19(1):11-23 (Feb. 1, 2004).

Vlasveld, L.T., et al., "Treatment of low-grade non-Hodgkin's lymphoma with continuous infusion of low-dose recombinant interleukin-2 in combination with the B-cell-specific monoclonal antibody CLB-CD19" Cancer Immunol Immunother 40(1):37-47 (Jan. 1, 1995).

Watanabe, M., et al., "Effect of Liposomes Containing Sodium Butyrate Conjugated with Anti-CD19 Monoclonal Antibody on in Vitro and in Vivo Growth of Malignant Lymphoma" Cancer Res 50(11):3245-3248 (Jun. 1, 1990).

Zhang, Z., et al., "Advances in the Isolation of Specific Monoclonal Rabbit Antibodies" Front Immunol 8(494):1-6 (May 5, 2017).

Zola, H., et al., "Preparation and characterization of a chimeric CD19 monoclonal antibody" Immunol Cell Biol 69(Pt. 6):411-422 (Dec. 1, 1991).

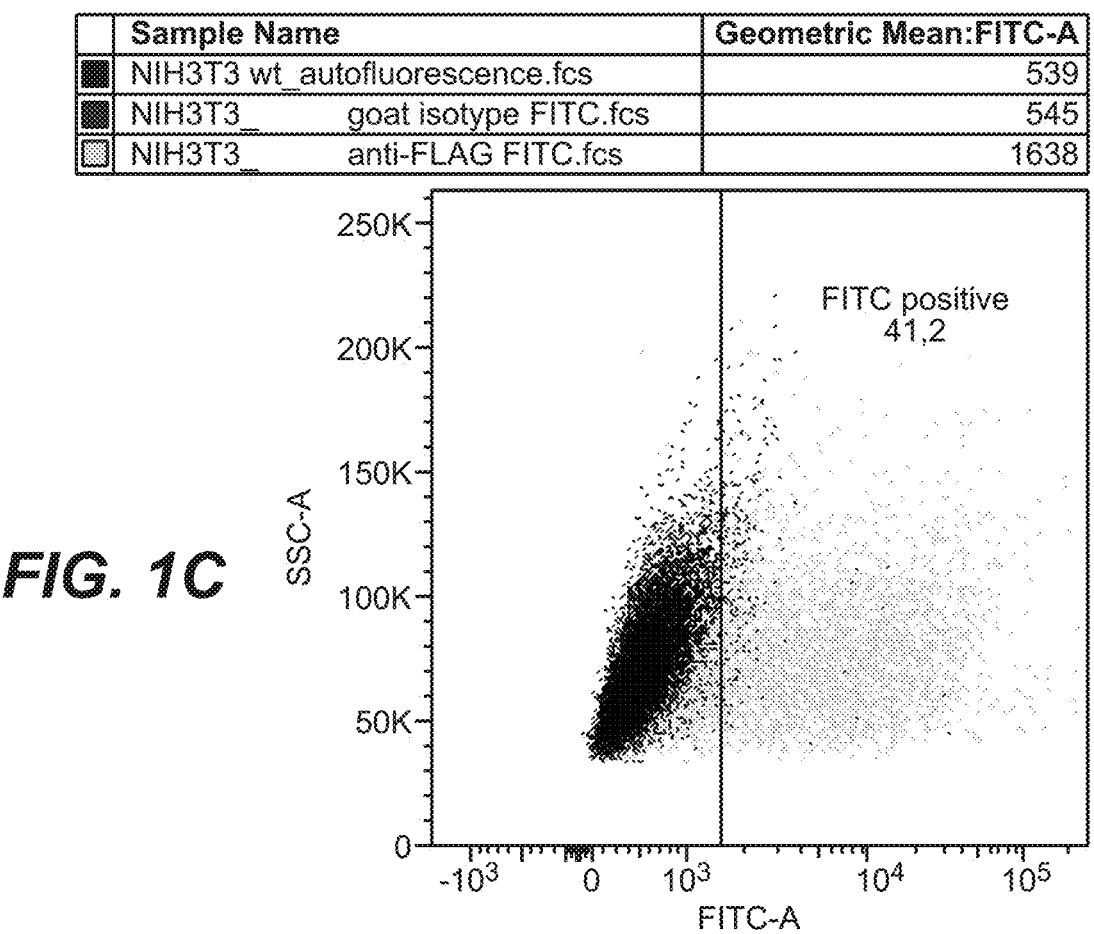

ANTI-RABBIT CD19 ANTIBODIES AND METHODS OF USE

CROSS REFERENCE TO RELATED APPLICATIONS

This application is a continuation of International Application No. PCT/EP2019/087064, filed Dec. 27, 2019, claiming priority to European Application No. 18215920.2, filed Dec. 30, 2018, which are incorporated herein by reference in their entirety.

SEQUENCE LISTING

This application contains a Sequence Listing which has been submitted electronically in ASCII format and is hereby incorporated by reference in its entirety. Said ASCII copy, created on Jun. 16, 2021, is named Sequence_listing.txt and is 111,329 bytes in size.

FIELD OF THE INVENTION

The present invention relates to antibodies against rabbit CD19 (anti-rabbit CD19 antibody), methods for their production, and uses thereof.

BACKGROUND

B-cells develop from pro-B and pre-B cells, and mature in the bone marrow to express antigen-specific cell surface antibody molecules, then progress through the transitional T1 and T2 stages of immature B-cell development within lymphoid tissues. In the spleen, the majority of B-cells partition into the mature follicular compartment or the numerically minor marginal zone, B1a, and regulatory B10 cell subsets. Mature antigen-specific B-cells activated by foreign antigens clonally expand and differentiate into short-lived plasma cells. Follicular B-cells can also enter germinal centers where antigen-selected B-cells expand, and their antigen receptors undergo affinity maturation and class-switch recombination (CSR). B-cells leave germinal centers as either memory B-cells or differentiate into long-lived plasma blasts that migrate to the bone marrow. B-cells are also found within the peritoneal cavity, including the regulatory B10 cell subset that can produce interleukin-10, the B1a subset that produces the majority of natural Ab, and the B1b subset that produces adaptive antibody responses to TI antigens. The majority of mature B-cells express CD20, while CD19 is expressed by mature B-cells, and some pre-B cells, plasmablasts, and short- and long-lived plasma cells. CD19 is expressed at higher densities by peritoneal B1a and B1b cells (Tedder, T. F., Nat Rev. Rheumatol. 5 (2009) 572-577; LeBien, T. W. and Tedder, T. F., Blood 112 (2008) 1570-1580).

CD19 is a transmembrane protein (B-cell co-receptor). The human CD19 structural gene encodes a cell surface molecule that assembles with the B-cell receptor in order to decrease the threshold for antigen receptor-dependent stimulation. CD19 primarily acts as a B-cell co-receptor in conjunction with CD21 and CD81. CD19 and CD21 are required for normal B-cell differentiation (Carter, R. H., et al., Immunol. Res. 26 (2002) 45-54). Upon activation, the cytoplasmic tail of CD19 becomes phosphorylated, which leads to binding by Src-family kinases and recruitment of PI-3 kinase.

Antibodies against human CD19 are e.g. mentioned in WO 2004/106381, WO 2005/012493, WO 2006/089133, WO 2007/002223, WO 2006/133450, WO 2006/121852, WO 2003/048209, U.S. Pat. No. 7,109,304, US 2006/0233791, US 2006/0280738, US 2006/0263357, US 2006/0257398, EP 1648512, EP 1629012, US 2008/0138336, WO 2008/022152, WO 2011/147834 and in Bruenke, J., et al., Br. J. Hematol. 130 (2005) 218-228; Vallera, D. A., et al., Cancer Biother. Radiopharm. 19 (2004) 11-23; Ghetie, M. A., et al., Blood 104 (2004) 178-183; Lang, P., et al., Blood 103 (2004) 3982-3985; Loeffler, A., et al., Blood 95 (2000) 2098-2103; Le Gall, F., et al., FEBS Lett. 453 (1999) 164-168; Li, Q., et al., Cancer Immunol. Immunother. 47 (1998) 121-130; Eberl, G., et al., Clin. Exp. Immunol. 114 (1998) 173-178; Pietersz, G. A., et al., Cancer Immunol. Immunother. 41 (1995) 53-60; Myers, D. E., et al., Leuk. Lymphoma. 18 (1995) 93-102; Bejcek, B. E., et al., Cancer Res. 55 (1995) 2346-2351; Hagen, I. A., et al, Blood 85 (1995) 3208-3212; Vlasfeld, L. T., et al., Cancer Immunol. Immunother. 40 (1995) 37-47; Rhodes, E. G. et al., Bone Marrow Transplant. 10 (1992) 485-489; Zola, H., et al., Immunol. Cell Biol. 69 (1991) 411-422; Watanabe, M., et al., Cancer Res. 50 (1990) 3245-3248; Uckun, F. M., et al., Blood 71 (1988) 13-29; Pezzutto, A., et al.; J Immunol. 138 (1987) 2793-2799. Monoclonal antibody SJ25-C1 is commercially available (Product No. 4737, Sigma-Aldrich Co. USA, SEQ ID NO: 21 to 24). Antibodies with increased affinity to the FcγRIIIA are mentioned in WO 2008/022152.

The rabbit genome has been sequenced and assembled in 2009 with a redundancy of 6.51 (see http://www.broadinstitute.org/science/projects/mammals-models/rabbit/rabbit-genome-sequencing-project).

No monoclonal anti-rabbit CD19 antibodies have been reported so far. Although alleged by some polyclonal antibodies cross-reactivity of anti-human CD19 antibodies or anti-mouse CD19 antibodies with rabbit CD19 could not be proven.

Thus, there is a need for providing a monoclonal anti-rabbit CD19 antibody.

SUMMARY

The current invention is directed to an anti-rabbit CD19 antibody and its use in labelling rabbit B-cells.

With the antibody according to the current invention it is possible, amongst other things, at least

- to characterize the B-cells in rabbit PBMCs or splenocytes;
- to enrich antigen-specific B-cells after macrophage depletion either before or after antigen panning;
- to selectively stain B-cells after co-cultivation with feeder cells (feeder cells out-grow B-cells by orders of magnitude);
- to sort and select B-cells with improved yield and quality (optionally in combination with one or more further markers).

One aspect of the current invention is an isolated antibody that specifically bind to rabbit CD19 comprising (a) a HVR-H1 comprising the amino acid sequence of SEQ ID NO: 32 or 33 or 34, (b) a HVR-H2 comprising the amino acid sequence of SEQ ID NO: 35 or 36, (c) a HVR-H3 comprising the amino acid sequence of SEQ ID NO: 37, (d) a HVR-L1 comprising the amino acid sequence of SEQ ID NO: 38, (e) a HVR-L2 comprising the amino acid sequence of SEQ ID NO: 39, and (f) a HVR-L3 comprising the amino acid sequence of SEQ ID NO: 40.

In one embodiment the antibody is a monoclonal antibody.

In one embodiment the antibody is a chimeric or humanized antibody.

In one embodiment the antibody comprises a variable heavy chain domain of SEQ ID NO: 30 and a variable light chain domain of SEQ ID NO: 26.

One aspect is a method for selecting a B-cell comprising the following steps:
- a) obtaining B-cells from the blood of a rabbit,
- b) incubating the B-cells with an antibody according to the current invention,
- c) selecting one or more B-cells to which the antibody according to the invention is bound.

In one embodiment the method further comprises one or more of the following steps:
- after step b) and prior to step c): incubating the B-cells at 37° C. for one hour in co-cultivation medium,
- c) (single) depositing one or more B-cells to which the antibody according to the invention is bound in an individual container,
- d) co-cultivating the (single) deposited cells with a feeder cell in a co-cultivation medium,
- e) selecting a B-cell proliferating in step d) and thereby selecting a B-cell.

One aspect as reported herein is a method for selecting a B-cell comprising the following steps:
- a) co-cultivating each of the B-cells of a population of B-cells, which has been deposited by FACS as single cell based on the binding of a labelled antibody according to the current invention thereto, with murine EL-4 B5 cells as feeder cells, and
- b) selecting a B-cell clone proliferating and secreting antibody in step a).

In one embodiment the co-cultivating is in the presence of a synthetic feeder mix that comprises IL-1β, TNFα, IL-10, and one or more selected from IL-21, SAC, BAFF, IL-2, IL-4, and IL-6.

In one embodiment the B-cell is a rabbit B-cell.

One aspect as reported herein is a method for producing an antibody binding to a target antigen comprising the following steps
- a) co-cultivating one or more B-cells of a population of B-cells, which has/have been deposited by FACS in an individual container based on the binding of a labelled antibody according to the current invention thereto, optionally in the presence of murine EL-4 B5 cells as feeder cells and IL-1β, TNFα, IL-10, and one or more selected from IL-21, SAC, BAFF, IL-2, IL-4, and IL-6 as feeder mix,
- b) selecting a B-cell clone producing an antibody specifically binding to the target antigen,
- b1) determining the nucleic acid sequence encoding the variable light chain domain and the variable heavy chain domain of the antibody by a reverse transcriptase PCR,
- b2) transfecting a cell with a nucleic acid comprising the nucleic acid sequence encoding the antibody variable light chain domain and the variable heavy chain domain,
- c) cultivating the cell, which contains the nucleic acid that encodes the antibody produced by the B-cell clone selected in step b) or a humanized variant thereof, and recovering the antibody from the cell or the cultivation supernatant and thereby producing the antibody.

In one embodiment the B-cell is a rabbit B-cell.

One aspect as reported herein is a method for co-cultivating one or more rabbit B-cells comprising the steps of incubating a multitude of rabbit B-cells/labelling individual B-cells of a multitude of rabbit B-cells with an antibody according to the current invention that is conjugated to a detectable label, selecting/depositing one or more rabbit B-cells that have the antibody according to the invention bound to their surface/that have been labelled either as individual B-cells (single deposited B-cell) or as a pool of B-cells (in an individual container), and co-cultivating the single deposited rabbit B-cells or the pool of rabbit B-cells with feeder cells, optionally incubating after the co-cultivation the obtained cell mixture with an antibody according to the current invention that is conjugated to a detectable label and selecting/depositing/counting rabbit B-cells that have the antibody according to the invention bound to their surface/that have been labelled.

One aspect as reported herein is a method for selecting a B-cell/removing non B-cells for a cultivation comprising the following steps:
- a) co-cultivating B-cells, which have been deposited either as single cells or as pool of cells, with feeder cells,
- b) incubating the cells from the co-cultivations obtained in step a) with the antibody according to the current invention, and
- c) selecting one or more B-cells to which the antibody according to the current invention is bound and thereby removing non-B-cells.

In one embodiment the B-cell is a rabbit B-cell.

One aspect as reported herein is a method for determining the number B-cells after cultivation of a single deposited B-cell comprising the following steps:
- a) co-cultivating a single deposited B-cell with feeder cells,
- b) incubating the cells from the co-cultivations obtained in step a) with the antibody according to the current invention, and
- c) determining the number of B-cells in the cultivation by counting the number of cells to which the antibody according to the current invention is bound.

In one embodiment the B-cell is a rabbit B-cell.

One aspect of the current invention is a method for removing non B-cells for a mixture of cells, such as e.g. a cultivation, comprising the following steps:
- a) co-cultivating a single deposited B-cell or a pool of B-cells with feeder cells,
- b) incubating the cells from the co-cultivation obtained in step a) with the antibody according to the invention, and
- c) selecting one or more cells to which the antibody according to the invention is bound and thereby selecting B-cells and removing non-B-cells from a mixture of cells.

In one embodiment the B-cell is a rabbit B-cell.

One aspect according to the current invention is a method for determining the number B-cells in a co-cultivation of a single deposited B-cell with feeder cells comprising the following steps:
- a) co-cultivating a single deposited B-cell with feeder cells,
- b) incubating the cells from the co-cultivation obtained in step a) with the antibody according to the invention, and c) determining the number of B-cells in the cultivation by counting the number of cells to which the antibody according to the invention is bound.

In one embodiment the B-cell is a rabbit B-cell.

DETAILED DESCRIPTION OF EMBODIMENTS OF THE INVENTION

CD19 is the optimal pan-B-cell marker as it is expressed in almost all stages of B-cell development until terminal differentiation into plasma cells (see e.g. Tedder above).

I. DEFINITIONS

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). The amino acid positions of all constant regions and domains of the heavy and light chain can be numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically, the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype, and the Kabat EU index numbering system (see pages 661-723) is used for the constant heavy chain domains (CH1, Hinge, CH2 and CH3, which is herein further clarified by referring to "numbering according to Kabat EU index" in this case).

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

It is also to be noted that the terms "comprising", "including", and "having" can be used interchangeably.

To a person skilled in the art procedures and methods are well known to convert an amino acid sequence, e.g. of a peptidic linker or fusion polypeptide, into a corresponding encoding nucleic acid sequence. Therefore, a nucleic acid is characterized by its nucleic acid sequence consisting of individual nucleotides and likewise by the amino acid sequence of a peptidic linker or fusion polypeptide encoded thereby.

The use of recombinant DNA technology enables the generation derivatives of a nucleic acid. Such derivatives can, for example, be modified in individual or several nucleotide positions by substitution, alteration, exchange, deletion or insertion. The modification or derivatization can, for example, be carried out by means of site directed mutagenesis. Such modifications can easily be carried out by a person skilled in the art (see e.g. Sambrook, J., et al., Molecular Cloning: A laboratory manual (1999) Cold Spring Harbor Laboratory Press, New York, USA; Hames, B. D., and Higgins, S. G., Nucleic acid hybridization—a practical approach (1985) IRL Press, Oxford, England).

Useful methods and techniques for carrying out the current invention are described in e.g. Ausubel, F. M. (ed.), Current Protocols in Molecular Biology, Volumes I to III (1997); Glover, N. D., and Hames, B. D., ed., DNA Cloning: A Practical Approach, Volumes I and II (1985), Oxford University Press; Freshney, R. I. (ed.), Animal Cell Culture—a practical approach, IRL Press Limited (1986); Watson, J. D., et al., Recombinant DNA, Second Edition, CHSL Press (1992); Winnacker, E. L., From Genes to Clones; N.Y., VCH Publishers (1987); Celis, J., ed., Cell Biology, Second Edition, Academic Press (1998); Freshney, R. I., Culture of Animal Cells: A Manual of Basic Technique, second edition, Alan R. Liss, Inc., N.Y. (1987).

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some aspects, the number of amino acid changes are 10 or less, 9 or less, 8 or less, 7 or less, 6 or less, 5 or less, 4 or less, 3 or less, or 2 or less. In some aspects, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein.

The terms "anti-rabbit CD19 antibody" and "an antibody that specifically binds to rabbit CD19" refer to an antibody that is capable of binding rabbit CD19 with sufficient affinity such that the antibody is useful as a diagnostic agent in targeting rabbit CD19.

The term "antibody" herein is used in the broadest sense and encompasses various antibody structures, including but not limited to monoclonal antibodies, multispecific antibodies (e.g., bispecific antibodies), and antibody fragments so long as they exhibit the desired rabbit CD19-binding activity.

An "antibody fragment" refers to a molecule other than an intact antibody that comprises a portion of an intact antibody that binds to rabbit CD19. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "Fc-region" is used herein to define a C-terminal region fragment of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) or glycine-lysine dipeptide (Gly446-Lys447), respectively, of the Fc-region may or may not be present. Numbering according to Kabat EU index.

The term "constant region (of an antibody)" is used herein to define the part of an immunoglobulin heavy chain excluding the variable domain. The term includes native sequence constant regions and variant constant regions. In one embodiment, a human IgG heavy chain constant region extends from Ala114 to the carboxyl-terminus of the heavy chain. However, the C-terminal lysine (Lys447) or glycine-lysine dipeptide (Gly446-Lys447), respectively, of the Fc-region may or may not be present. Numbering according to Kabat EU index.

The antibody according to the current invention comprise as Fc-region, in one embodiment an Fc-region derived from human origin. In one embodiment the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat). Antibodies of human subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG1 or IgG4 subclass. In one embodiment the Fc-region is of the human IgG4 subclass comprising the mutations S228P and/or L235E (numbering according to EU index of Kabat). In one embodiment the Fc-region is of the human IgG1 subclass comprising the mutations L234A, L235A and optionally P329G (numbering according to EU index of Kabat).

The term "detectable label" as used herein encompasses chromogens (fluorescent or luminescent groups and dyes), enzymes, NMR-active groups, metal particles, or haptens, such as digoxygenin. In one embodiment the detectable label is a fluorescent dye. Metal chelates which can be detected by electrochemiluminescense are also in one embodiment signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one aspect, for the VL, the subgroup is subgroup kappa I or III as in Kabat et al., supra. In one aspect, for the VH, the subgroup is subgroup III as in Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody," and "whole antibody" are used herein interchangeably to refer to an antibody having a structure substantially similar to a native antibody structure or having heavy chains that contain an Fc region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242.);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-rabbit CD19 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, ClustalW, Megalign (DNASTAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, percent amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from www.fasta.bioch.virginia.edu/fasta_www2/fasta_down.shtml or www.ebi.ac.uk/Tools/sss/fasta. Alternatively, a public server accessible at fasta.bioch.virginia.edu/fasta_www2/index.cgi can be used to compare the sequences, using the ggsearch (global protein: protein) program and default options (BLOSUM50; open: −10; ext: −2; Ktup=2) to ensure a global, rather than local, alignment is performed. Percent amino acid identity is given in the output alignment header.

The term "CD19", as used herein, refers to rabbit B-lymphocyte antigen CD19 (alternative name(s) are: Differentiation antigen CD19, B-lymphocyte surface antigen B4, T-cell surface antigen Leu-12). The term encompasses "full-length" unprocessed rabbit CD19 (SEQ ID NO: 02) as well as any form of rabbit CD19 that results from processing in the cell thereof, e.g. by cleavage of the signal peptide, as long as the antibody as reported herein binds thereto, such as e.g. SEQ ID NO: 01 and fragments thereof.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (see, e.g., Kindt, T. J., et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

via surface presented CD19 allows for an improved B-cell enrichment or even sorting. The improvement is in, amongst other things, a more specific labelling and thereby enrichment/sorting/single cell deposition or/and a facilitated process wherein the number of B-cells to be processed is reduced and at the same time the number of B-cells producing an antigen-specific antibody is increased.

The invention is based at least in part on the finding that the anti-rabbit CD19 antibody according to the invention when compared to an anti-rabbit CD20 antibody does not result in apoptosis of the B-cells when used as cell surface marker.

Until the current invention was made, the only antibodies that were useful to specifically stain rabbit B-cells were antibodies against cell surface immunoglobulins like IgG, IgM, IgA, or human light chain in human transgenic rabbits. No specific B-cell marker was available for specifically staining the entire B-cell population. With the anti-rabbit CD19 antibody according to the current invention, it is for the first time possible to identify and specifically stain the entire rabbit B-cell population.

The rabbit CD19 sequence comprises an extended gap in exon #3 when compared to other non-rodent mammalian species (see alignment).

```
hamster          RDLDCGLENR  SSGSHRPSSG  SHNSSWLYVW  AKDHPEVVGT  169 mouse            RDLDCDLRNR  SSGSHRSTSG  ....SQLYVW  AKDHPKVWGT  165 rat              GDLDCDLGNR  SSGSHRSTSG  ....SQLYVW  ATDHPEVWKT  165 squirrel         EALKCSRGNM  SSGGTGLSSA  PPNTSQLYVW  AKDHPKIWNT  136 rabbit           GGPGCGLGNE  SS........  ...SSQPYVW  DRDHPKEWDM  157 marmoset         SGQGCGLENR  SSEDPSSPSG  NLMSSQLYVN  AKDRPKIWEG  170 rhesus macaque   GGLGCGLKNR  SSEGPSSPSG  KLNSSQLYVW  AKDRPEMWEG  169 human            GGLGCGLKNR  SSEGPSSPSG  KLMSPKLYVW  AKDRPEIWEG  169 cat              NDPGCGLGNR  SSEGPKPSSG  YPTSSQLYVW  AKGHPEIWET  165 naked mole rat   GDLSCGPGNG  SSGRPRLAPH  HRNNSQLYVW  NKGHPEIWEA  169 guinea pig       GDFSCGPGNG  SSEGPTPSSQ  HPNSSQLYVW  DKRDSPSWEP   45
(SEQ ID NO from top to bottom: 04, 05, 06, 07, 02, 08, 09, 10, 11,
12, 13 corresponding to TR_ROD:G3I7M5_CRIGR[1039:], SW:CD19_MOUSE,
TR_ROD:F1LNH2_RAT, TR_ROD:I3MSE7_SPETR[38:], TR_VRT:G1TWR4_RABIT,
SW:CD19_CALJA, TR_VRT:F7F486_MACMU, SW:CD19_HUMAN,
TR_VRT:M3VZQ6_FELCA, TR_ROD:G5BRD9_HETGA, SW:CD19_CAVPO,
SW_ROD:CD19_CAVPO, TR_ROD:H0UXI6_CAVPO)
```

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. COMPOSITIONS AND METHODS

The invention is based at least in part on the finding that rabbit CD19 is a highly valuable, pan rabbit B-cell marker.

In more detail, it has been found that rabbit CD19 is an advantageous cell surface marker for the analysis and characterization of rabbit B-cells. The labelling of rabbit B-cells For the isolation of the gene from the rabbit genome the 5'/3'-UTR regions have been extracted from rabbit, human and mouse and compared to result in regions that PCR primers can be placed in (rb_5 UTR_primer_region1 (SEQ ID NO: 17), rb_5UTR_primer_region2 (SEQ ID NO: 18), rb_3 UTR_primer_region (SEQ ID NO: 19)). Exemplary primers have the sequence of SEQ ID NO: 53 (binding in 3' UTR) and SEQ ID NO: 54 (binding in 5' UTR).

For the isolation of rabbit CD19 genomic DNA either the primer combinations of rbCD19 UTR forward primer and rbCD19 UTR reverse primer (binding in the 5'/3'-UTR sequences of the rabbit CD19 structural gene; SEQ ID NO: 20 and 21) or the primer combination rbCD19 CDS forward primer and rbCD19 CDS reverse primer (binding at the start- and the stop-codon, respectively, of the rabbit CD19 structural gene; SEQ ID NO: 22 and 23) can be used. The respective amplification products have a length of 1831 bp or 1663 bp, respectively.

The antibody according to the current invention was generated by immunizing mice with a rabbit-CD19 expression plasmid. Prior to harvest of the B-cells the immunized mice were boosted with rabbit CD19 presenting cells transfected with rabbit CD19 DNA. The harvested B-cells were fused with myeloma cells to generate hybridoma cells.

The rabbit CD19 expressing cells used in the boost are NIH/3T3 (ATCC® CRL-1658™) mouse embryo fibroblast cells that have been transfected with a rabbit-CD19-GPI anchor-FLAG-tag fusion polypeptide. Rabbit CD19 expression on cell surface works well in NIH/3T3 cells (about 40% FITC positive cells after 24 hours) with high signal with intracellular staining. Unexpectedly when closely related C2C12 (ATCC® CRL-1772™) mouse muscle myoblast cells were used no expression of said construct could be detected (almost no rabbit CD19 positive cells detectable; about 9% FITC positive cells after 24 hours). A further improvement in the rabbit CD19 expression could be achieved by using a reverse transfection approach (see FIGS. 1A-1C). It has been shown for CHO and HEK cells that the FLAG-tag can be used as surrogate for the detection of cell surface expressed rabbit CD19 (see following tables).

| cell line | total cell number [n] | anti-FlagTag antibody-Alexa 488-conjugate stained cells absolute [n]/ relative to total number [%] |
|---|---|---|
| CHO wt | 25354 | 1/0.0 |
| CHO-S transfected with CD19 expression plasmid | 21142 | 719/3.4 |

| cell line | total cell number [n] | anti-FlagTag antibody-Alexa 488-conjugate stained cells absolute [n]/ relative to total number [%] |
|---|---|---|
| HEK wt | 24156 | 7/0.0 |
| HEK293F transfected with CD19 expression plasmid | 20052 | 7333/36.6 |

Figure 2A:
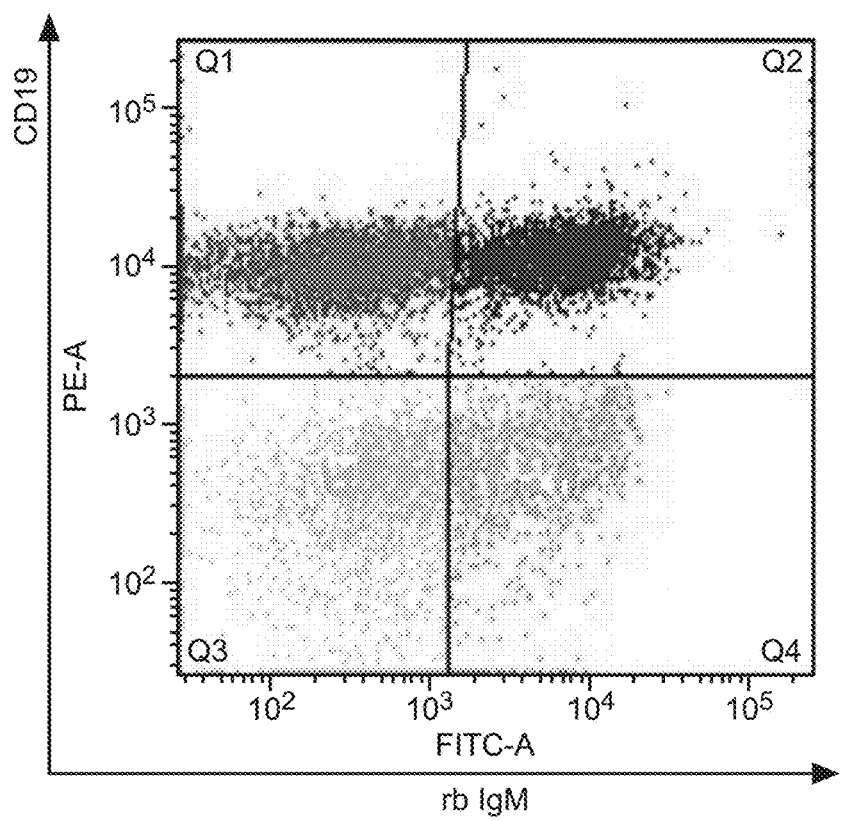
Figure 2B:
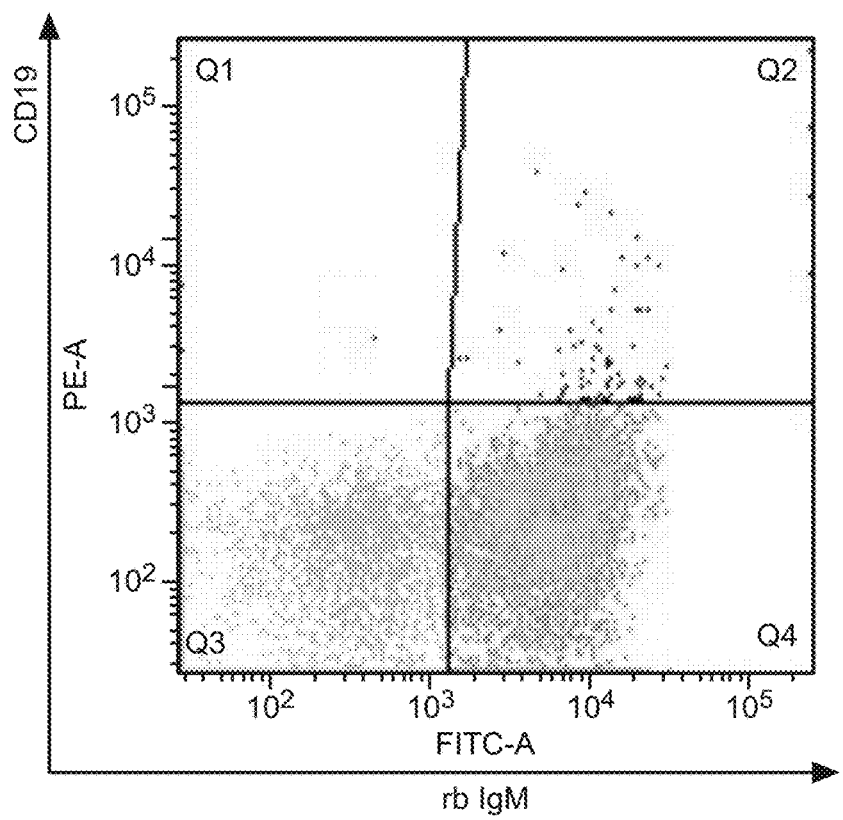

| cell line | total cell number [n] | polyclonal anti-mIgG antibody-APC-conjugate stained cells absolute [n]/ relative to total number [%] |
|---|---|---|
| CHO wt | 25414 | 4/0.0 |
| CHO-S transfected with CD19 expression plasmid | 21266 | 975/4.6 |
| HEK wt | 24409 | 2/0.0 |
| HEK293F transfected with CD19 expression plasmid | 20303 | 7293/35.9 | anti-FlagTag antibody-Alexa 488-conjugate = detection of FLAG-tag by anti-Flag-tag antibody labelled with Alexa 488
polyclonal anti-mIgG antibody-APC-conjugate = detection of anti-rabbit CD19 antibody by anti-murine IgG antibody labelled with APC Out of 356 generated hybridoma cells only a single cell, clone 1H2, expressed an anti-rabbit CD19 antibody with a (decent) affinity to native rabbit CD19 on the B-cell surface (see FIGS. 2A-2B and following Table).

| plate-well | All Events #Events | PBLs #Events | rbIgM #Events | aMouse-PE #Events | Q1 #Events | Q2 #Events | Q3 #Events | Q4 #Events | Ratio Q2/IgM (%) |
|---|---|---|---|---|---|---|---|---|---|
| 1-A1 | 12970 | 10135 | 4268 | 14 | 4 | 9 | 5337 | 4376 | 0.21 |
| 1-A2 | 12943 | 10127 | 3981 | 10 | 1 | 9 | 5658 | 4096 | 0.23 |
| 1-A3 | 12919 | 10103 | 4177 | 12 | 1 | 8 | 5471 | 4274 | 0.19 |
| 1-A4 | 12988 | 10136 | 4404 | 9 | 0 | 5 | 5185 | 4510 | 0.11 |
| 1-A5 | 13176 | 10133 | 4344 | 10 | 3 | 3 | 5298 | 4435 | 0.07 |
| 1-A6 | 13086 | 10128 | 4211 | 10 | 1 | 7 | 5371 | 4339 | 0.17 |
| 1-A7 | 12984 | 10118 | 4117 | 7 | 0 | 4 | 5461 | 4254 | 0.10 |
| 1-A8 | 13006 | 10114 | 4151 | 8 | 0 | 7 | 5392 | 4298 | 0.17 |
| 1-A9 | 13333 | 10134 | 4186 | 4 | 0 | 4 | 5466 | 4298 | 0.10 |
| 1-A10 | 12872 | 10098 | 4150 | 7 | 0 | 6 | 5468 | 4257 | 0.14 |
| 1-A11 | 15661 | 10165 | 3983 | 5 | 0 | 4 | 5765 | 4096 | 0.10 |
| 1-A12 | 12972 | 10118 | 4095 | 12 | 0 | 9 | 5562 | 4218 | 0.22 |
| 1-B1 | 12819 | 10116 | 4168 | 5 | 2 | 3 | 5442 | 4287 | 0.07 |
| 1-B2 | 12876 | 10096 | 4314 | 11 | 3 | 5 | 5320 | 4382 | 0.12 |
| 1-B3 | 12933 | 10107 | 4103 | 11 | 1 | 7 | 5438 | 4268 | 0.17 |
| 1-B4 | 12826 | 10113 | 4277 | 10 | 0 | 8 | 5362 | 4369 | 0.19 |
| 1-B5 | 12712 | 10113 | 4177 | 5 | 1 | 4 | 5459 | 4272 | 0.10 |
| 1-B6 | 12799 | 10132 | 4234 | 9 | 1 | 7 | 5435 | 4330 | 0.17 |
| 1-B7 | 12823 | 10124 | 4104 | 19 | 2 | 14 | 5580 | 4198 | 0.34 |
| 1-B8 | 12743 | 10118 | 4155 | 6 | 0 | 5 | 5480 | 4255 | 0.12 |
| 1-B9 | 13202 | 10139 | 4024 | 9 | 0 | 5 | 5679 | 4142 | 0.12 |
| 1-B10 | 12713 | 10130 | 4069 | 14 | 2 | 9 | 5581 | 4219 | 0.22 |
| 1-B11 | 12744 | 10116 | 4242 | 7 | 1 | 3 | 5449 | 4349 | 0.07 |
| 1-B12 | 12769 | 10128 | 4083 | 3 | 1 | 2 | 5588 | 4208 | 0.05 |
| 1-C1 | 12651 | 10100 | 4171 | 9 | 0 | 8 | 5474 | 4287 | 0.19 |
| 1-C2 | 13540 | 10134 | 4265 | 47 | 4 | 34 | 5390 | 4364 | 0.80 |
| 1-C3 | 12711 | 10102 | 4142 | 8 | 1 | 6 | 5478 | 4269 | 0.14 |
| 1-C4 | 12804 | 10112 | 4172 | 6 | 0 | 3 | 5454 | 4273 | 0.07 |
| 1-C5 | 12678 | 10153 | 3959 | 15 | 0 | 9 | 5763 | 4072 | 0.23 |
| 1-C6 | 12709 | 10125 | 3974 | 6 | 1 | 3 | 5721 | 4068 | 0.08 |
| 1-C7 | 12582 | 10141 | 3887 | 10 | 1 | 7 | 5849 | 4010 | 0.18 |
| 1-C8 | 12915 | 10119 | 4081 | 12 | 2 | 8 | 5531 | 4212 | 0.20 |
| 1-C9 | 12651 | 10132 | 3938 | 8 | 1 | 5 | 5714 | 4072 | 0.13 |
| 1-C10 | 13517 | 10115 | 3874 | 6 | 4 | 0 | 5781 | 4043 | 0.00 |
| 1-C11 | 12860 | 10141 | 4102 | 6 | 2 | 3 | 5597 | 4235 | 0.07 |

-continued

| plate-well | All Events #Events | PBLs #Events | rbIgM #Events | aMouse-PE #Events | Q1 #Events | Q2 #Events | Q3 #Events | Q4 #Events | Ratio Q2/IgM (%) |
|---|---|---|---|---|---|---|---|---|---|
| 1-C12 | 12823 | 10132 | 3939 | 3 | 1 | 2 | 5756 | 4069 | 0.05 |
| 1-D1 | 12710 | 10098 | 4067 | 6 | 2 | 4 | 5625 | 4147 | 0.10 |
| 1-D2 | 12675 | 10119 | 4026 | 6 | 1 | 4 | 5628 | 4182 | 0.10 |
| 1-D3 | 12599 | 10141 | 3853 | 2341 | 1 | 2020 | 5893 | 1952 | 52.43 |
| 1-D4 | 12599 | 10123 | 3954 | 15 | 1 | 10 | 5703 | 4074 | 0.25 |
| 1-D5 | 12500 | 10112 | 4043 | 11 | 2 | 9 | 5607 | 4158 | 0.22 |
| 1-D6 | 12648 | 10131 | 3941 | 10 | 0 | 7 | 5716 | 4077 | 0.18 |
| 1-D7 | 12679 | 10121 | 3877 | 6 | 0 | 4 | 5767 | 4050 | 0.10 |
| 1-D8 | 12969 | 10118 | 3803 | 14 | 3 | 7 | 5836 | 3959 | 0.18 |
| 1-D9 | 12630 | 10173 | 3574 | 6 | 0 | 4 | 6264 | 3749 | 0.11 |
| 1-D10 | 12863 | 10138 | 3791 | 5 | 1 | 4 | 5794 | 3996 | 0.11 |
| 1-D11 | 12888 | 10143 | 4089 | 14 | 0 | 12 | 5622 | 4215 | 0.29 |
| 1-D12 | 12881 | 10142 | 3914 | 18 | 2 | 11 | 5772 | 4091 | 0.28 |
| 1-E1 | 12557 | 10117 | 4023 | 9 | 2 | 6 | 5611 | 4163 | 0.15 |
| 1-E2 | 12837 | 10133 | 3930 | 23 | 2 | 17 | 5641 | 4128 | 0.43 |
| 1-E3 | 12768 | 10127 | 3963 | 8 | 1 | 5 | 5709 | 4109 | 0.13 |
| 1-E4 | 12585 | 10159 | 3668 | 9 | 2 | 5 | 6130 | 3800 | 0.14 |
| 1-E5 | 14898 | 10208 | 3458 | 19 | 2 | 9 | 6290 | 3708 | 0.26 |
| 1-E6 | 12830 | 10183 | 3545 | 11 | 2 | 7 | 6354 | 3656 | 0.20 |
| 1-E7 | 13233 | 10143 | 3660 | 14 | 4 | 7 | 5960 | 3871 | 0.19 |
| 1-E8 | 12706 | 10161 | 3553 | 8 | 1 | 7 | 6182 | 3742 | 0.20 |
| 1-E9 | 12648 | 10155 | 3793 | 8 | 1 | 5 | 5908 | 3941 | 0.13 |
| 1-E10 | 12828 | 10170 | 3375 | 10 | 2 | 7 | 6305 | 3623 | 0.21 |
| 1-E11 | 12735 | 10194 | 3533 | 3 | 1 | 2 | 6188 | 3739 | 0.06 |
| 1-E12 | 15157 | 10226 | 3978 | 247 | 5 | 171 | 5670 | 4095 | 4.30 |
| 1-F1 | 12722 | 10131 | 4046 | 10 | 3 | 7 | 5636 | 4192 | 0.17 |
| 1-F2 | 12664 | 10145 | 3503 | 9 | 0 | 7 | 6092 | 3743 | 0.20 |
| 1-F3 | 13391 | 10172 | 3330 | 3 | 0 | 3 | 6373 | 3563 | 0.09 |
| 1-F4 | 12662 | 10129 | 3802 | 12 | 1 | 8 | 5840 | 3963 | 0.21 |
| 1-F5 | 12716 | 10140 | 3684 | 9 | 2 | 6 | 5967 | 3894 | 0.16 |
| 1-F6 | 15065 | 10136 | 3431 | 9 | 1 | 7 | 6114 | 3694 | 0.20 |
| 1-F7 | 12789 | 10124 | 3786 | 8 | 1 | 6 | 5762 | 3986 | 0.16 |
| 1-F8 | 12753 | 10147 | 3690 | 7 | 1 | 4 | 5958 | 3881 | 0.11 |
| 1-F9 | 12728 | 10141 | 3841 | 10 | 0 | 7 | 5766 | 4053 | 0.18 |
| 1-F10 | 12970 | 10155 | 3831 | 4 | 1 | 2 | 5744 | 4083 | 0.05 |
| 1-F11 | 13382 | 10222 | 3493 | 10 | 1 | 9 | 6304 | 3758 | 0.26 |
| 1-F12 | 12748 | 10151 | 3586 | 6 | 2 | 4 | 6074 | 3801 | 0.11 |
| 1-G1 | 12713 | 10108 | 3954 | 18 | 2 | 10 | 5647 | 4137 | 0.25 |
| 1-G2 | 12587 | 10124 | 3569 | 5 | 2 | 1 | 5982 | 3845 | 0.03 |
| 1-G3 | 12772 | 10140 | 3384 | 7 | 1 | 3 | 6120 | 3684 | 0.09 |
| 1-G4 | 12731 | 10193 | 3364 | 11 | 2 | 7 | 6459 | 3534 | 0.21 |
| 1-G5 | 12548 | 10177 | 3471 | 17 | 3 | 13 | 6372 | 3601 | 0.37 |
| 1-G6 | 13090 | 10198 | 3623 | 6 | 2 | 2 | 6266 | 3786 | 0.06 |
| 1-G7 | 15347 | 10229 | 4109 | 543 | 23 | 370 | 5524 | 3991 | 9.00 |
| 1-G8 | 12787 | 10137 | 3745 | 6 | 0 | 5 | 5824 | 3974 | 0.13 |
| 1-G9 | 12897 | 10148 | 3775 | 5 | 2 | 2 | 5925 | 3948 | 0.05 |
| 1-G10 | 12776 | 10141 | 3570 | 8 | 3 | 4 | 5943 | 3872 | 0.11 |
| 1-G11 | 12861 | 10129 | 3726 | 4 | 1 | 2 | 5759 | 4051 | 0.05 |
| 1-G12 | 12818 | 10135 | 3811 | 6 | 1 | 4 | 5740 | 4043 | 0.10 |
| 1-H1 | 12904 | 10120 | 3592 | 31 | 3 | 18 | 5907 | 3823 | 0.50 |
| 1-H2 | 12588 | 10142 | 3516 | 4857 | 1458 | 3276 | 4775 | 411 | 93.17 |
| 1-H3 | 12676 | 10126 | 3753 | 21 | 6 | 15 | 5755 | 3954 | 0.40 |
| 1-H4 | 12626 | 10115 | 3413 | 11 | 4 | 7 | 6132 | 3651 | 0.21 |
| 1-H5 | 12658 | 10159 | 3628 | 2 | 1 | 1 | 6028 | 3842 | 0.03 |
| 1-H6 | 12783 | 10149 | 3614 | 3 | 2 | 1 | 5862 | 3886 | 0.03 |
| 1-H7 | 14697 | 10229 | 3841 | 650 | 25 | 418 | 5540 | 3811 | 10.88 |
| 1-H8 | 12847 | 10140 | 3569 | 10 | 2 | 5 | 5900 | 3870 | 0.14 |
| 1-H9 | 12704 | 10147 | 3330 | 13 | 2 | 6 | 6247 | 3631 | 0.18 |
| 1-H10 | 12746 | 10105 | 3422 | 5 | 1 | 3 | 5944 | 3797 | 0.09 |
| 1-H11 | 12771 | 10146 | 3574 | 14 | 1 | 10 | 5989 | 3790 | 0.28 |
| 1-H12 | 315 | 138 | 57 | 2 | 0 | 2 | 70 | 59 | 3.51 |
| 2-A1 | 12516 | 10000 | 3806 | 4 | 0 | 3 | 5849 | 3906 | 0.08 |
| 2-A2 | 12680 | 10000 | 3758 | 5 | 0 | 3 | 5970 | 3875 | 0.08 |
| 2-A3 | 12987 | 10000 | 3716 | 9 | 2 | 6 | 6081 | 3817 | 0.16 |
| 2-A4 | 13822 | 10000 | 3541 | 43 | 5 | 32 | 6189 | 3637 | 0.90 |
| 2-A5 | 12964 | 10000 | 3675 | 15 | 0 | 7 | 6087 | 3797 | 0.19 |
| 2-A6 | 14786 | 10000 | 3960 | 582 | 68 | 394 | 5433 | 3777 | 9.95 |
| 2-A7 | 15245 | 10000 | 3811 | 309 | 16 | 190 | 5679 | 3834 | 4.99 |
| 2-A8 | 15379 | 10000 | 4088 | 641 | 50 | 390 | 5367 | 3970 | 9.54 |
| 2-A9 | 13968 | 10000 | 3689 | 419 | 80 | 226 | 5772 | 3702 | 6.13 |
| 2-A10 | 13058 | 10000 | 3556 | 12 | 0 | 8 | 6149 | 3715 | 0.22 |
| 2-A11 | 14999 | 10000 | 3942 | 334 | 33 | 177 | 5653 | 3980 | 4.49 |
| 2-A12 | 13517 | 10000 | 3675 | 11 | 0 | 11 | 6076 | 3797 | 0.30 |
| 2-B1 | 12656 | 10000 | 3943 | 12 | 2 | 9 | 5614 | 4106 | 0.23 |
| 2-B2 | 12631 | 10000 | 3530 | 5 | 2 | 1 | 6053 | 3718 | 0.03 |
| 2-B3 | 13039 | 10000 | 3594 | 8 | 1 | 7 | 6123 | 3729 | 0.19 |

-continued

| plate-well | All Events #Events | PBLs #Events | rbIgM #Events | aMouse-PE #Events | Q1 #Events | Q2 #Events | Q3 #Events | Q4 #Events | Ratio Q2/IgM (%) |
|---|---|---|---|---|---|---|---|---|---|
| 2-B4 | 12549 | 10000 | 3487 | 9 | 2 | 6 | 6183 | 3653 | 0.17 |
| 2-B5 | 12541 | 10000 | 3443 | 7 | 0 | 5 | 6214 | 3574 | 0.15 |
| 2-B6 | 14887 | 10000 | 3944 | 717 | 64 | 469 | 5271 | 3812 | 11.89 |
| 2-B7 | 12727 | 10000 | 3278 | 8 | 0 | 7 | 6369 | 3509 | 0.21 |
| 2-B8 | 15115 | 10000 | 4012 | 542 | 84 | 377 | 5272 | 3835 | 9.40 |
| 2-B9 | 15122 | 10000 | 3930 | 529 | 55 | 372 | 5469 | 3847 | 9.47 |
| 2-B10 | 12861 | 10000 | 3578 | 10 | 1 | 6 | 6046 | 3778 | 0.17 |
| 2-B11 | 12781 | 10000 | 3480 | 12 | 2 | 7 | 6191 | 3661 | 0.20 |
| 2-B12 | 12643 | 10000 | 3493 | 5 | 0 | 3 | 6210 | 3648 | 0.09 |
| 2-C1 | 12677 | 10000 | 3776 | 4 | 1 | 3 | 5812 | 3950 | 0.08 |
| 2-C2 | 12676 | 10000 | 4055 | 8 | 0 | 8 | 5485 | 4228 | 0.20 |
| 2-C3 | 12879 | 10000 | 3471 | 13 | 4 | 8 | 6116 | 3662 | 0.23 |
| 2-C4 | 12769 | 10000 | 3343 | 14 | 2 | 8 | 6359 | 3502 | 0.24 |
| 2-C5 | 12593 | 10000 | 3550 | 7 | 2 | 4 | 6048 | 3718 | 0.11 |
| 2-C6 | 12876 | 10000 | 3413 | 14 | 0 | 14 | 6245 | 3618 | 0.41 |
| 2-C7 | 12527 | 10000 | 3313 | 10 | 3 | 5 | 6278 | 3576 | 0.15 |
| 2-C8 | 14229 | 10000 | 3637 | 7 | 0 | 6 | 6089 | 3802 | 0.16 |
| 2-C9 | 13222 | 10000 | 3638 | 32 | 2 | 15 | 6057 | 3815 | 0.41 |
| 2-C10 | 13066 | 10000 | 3424 | 10 | 1 | 8 | 6252 | 3620 | 0.23 |
| 2-C11 | 13085 | 10000 | 3592 | 9 | 1 | 7 | 6120 | 3762 | 0.19 |
| 2-C12 | 13267 | 10000 | 3434 | 7 | 0 | 7 | 6263 | 3654 | 0.20 |
| 2-D1 | 12623 | 10000 | 3820 | 2 | 0 | 2 | 5673 | 4054 | 0.05 |
| 2-D2 | 12543 | 10000 | 3386 | 7 | 1 | 4 | 6241 | 3599 | 0.12 |
| 2-D3 | 12686 | 10000 | 3795 | 8 | 0 | 5 | 5754 | 3987 | 0.13 |
| 2-D4 | 12772 | 10000 | 3323 | 4 | 1 | 2 | 6289 | 3556 | 0.06 |
| 2-D5 | 12727 | 10000 | 3396 | 7 | 0 | 7 | 6232 | 3618 | 0.21 |
| 2-D6 | 12812 | 10000 | 3426 | 10 | 0 | 8 | 6256 | 3628 | 0.23 |
| 2-D7 | 12780 | 10000 | 3248 | 6 | 0 | 5 | 6358 | 3506 | 0.15 |
| 2-D8 | 12701 | 10000 | 3216 | 12 | 3 | 7 | 6335 | 3488 | 0.22 |
| 2-D9 | 12895 | 10000 | 3421 | 7 | 0 | 5 | 6236 | 3637 | 0.15 |
| 2-D10 | 12824 | 10000 | 3418 | 10 | 4 | 4 | 6243 | 3617 | 0.12 |
| 2-D11 | 12953 | 10000 | 3575 | 33 | 2 | 11 | 6131 | 3744 | 0.31 |
| 2-D12 | 12948 | 10000 | 3205 | 4 | 1 | 3 | 6411 | 3458 | 0.09 |
| 2-E1 | 12600 | 10000 | 3706 | 10 | 0 | 7 | 5767 | 3941 | 0.19 |
| 2-E2 | 12767 | 10000 | 3741 | 4 | 0 | 4 | 5829 | 3925 | 0.11 |
| 2-E3 | 13422 | 10000 | 3704 | 14 | 2 | 7 | 6032 | 3847 | 0.19 |
| 2-E4 | 12674 | 10000 | 3495 | 7 | 1 | 6 | 6121 | 3686 | 0.17 |
| 2-E5 | 12842 | 10000 | 3614 | 6 | 0 | 5 | 5993 | 3821 | 0.14 |
| 2-E6 | 12699 | 10000 | 3230 | 11 | 0 | 8 | 6380 | 3471 | 0.25 |
| 2-E7 | 13468 | 10000 | 3426 | 337 | 25 | 181 | 6025 | 3576 | 5.28 |
| 2-E8 | 12804 | 10000 | 3658 | 11 | 2 | 5 | 5900 | 3892 | 0.14 |
| 2-E9 | 12617 | 10000 | 3229 | 9 | 0 | 6 | 6345 | 3479 | 0.19 |
| 2-E10 | 12975 | 10000 | 3305 | 5 | 1 | 2 | 6312 | 3571 | 0.06 |
| 2-E11 | 12773 | 10000 | 3568 | 7 | 0 | 5 | 5998 | 3801 | 0.14 |
| 2-E12 | 12649 | 10000 | 3581 | 13 | 1 | 9 | 5899 | 3823 | 0.25 |
| 2-F1 | 12812 | 10000 | 3773 | 8 | 3 | 4 | 5726 | 3968 | 0.11 |
| 2-F2 | 14086 | 10000 | 3567 | 111 | 2 | 55 | 5979 | 3743 | 1.54 |
| 2-F3 | 12747 | 10000 | 3671 | 10 | 0 | 7 | 5780 | 3925 | 0.19 |
| 2-F4 | 12758 | 10000 | 3672 | 10 | 1 | 7 | 5803 | 3920 | 0.19 |
| 2-F5 | 12513 | 10000 | 3430 | 10 | 2 | 8 | 6005 | 3734 | 0.23 |
| 2-F6 | 12633 | 10000 | 3647 | 12 | 3 | 7 | 5821 | 3876 | 0.19 |
| 2-F7 | 12698 | 10000 | 3297 | 5 | 0 | 5 | 6149 | 3616 | 0.15 |
| 2-F8 | 12671 | 10000 | 3386 | 4 | 1 | 3 | 6213 | 3585 | 0.09 |
| 2-F9 | 12635 | 10000 | 3121 | 4 | 2 | 1 | 6405 | 3402 | 0.03 |
| 2-F10 | 12661 | 10000 | 3525 | 10 | 1 | 9 | 5917 | 3784 | 0.26 |
| 2-F11 | 12928 | 10000 | 3227 | 6 | 1 | 5 | 6410 | 3473 | 0.15 |
| 2-F12 | 12751 | 10000 | 3357 | 4 | 0 | 3 | 6154 | 3636 | 0.09 |
| 2-G1 | 12732 | 10000 | 3716 | 12 | 2 | 10 | 5759 | 3935 | 0.27 |
| 2-G2 | 12696 | 10000 | 3537 | 11 | 1 | 10 | 6117 | 3745 | 0.28 |
| 2-G3 | 12593 | 10000 | 3362 | 7 | 1 | 4 | 6221 | 3591 | 0.12 |
| 2-G4 | 12967 | 10000 | 3349 | 4 | 0 | 2 | 6282 | 3590 | 0.06 |
| 2-G5 | 12737 | 10000 | 3073 | 6 | 0 | 4 | 6459 | 3384 | 0.13 |
| 2-G6 | 12724 | 10000 | 3447 | 9 | 2 | 2 | 6126 | 3684 | 0.06 |
| 2-G7 | 12606 | 10000 | 3428 | 7 | 2 | 3 | 6185 | 3628 | 0.09 |
| 2-G8 | 12568 | 10000 | 3613 | 8 | 0 | 5 | 5964 | 3803 | 0.14 |
| 2-G9 | 15153 | 10000 | 4221 | 522 | 43 | 352 | 5125 | 4103 | 8.34 |
| 2-G10 | 12799 | 10000 | 3712 | 8 | 0 | 7 | 5772 | 3952 | 0.19 |
| 2-G11 | 12966 | 10000 | 3699 | 8 | 1 | 5 | 5837 | 3920 | 0.14 |
| 2-G12 | 12984 | 10000 | 3563 | 77 | 6 | 47 | 5830 | 3844 | 1.32 |
| 2-H1 | 12954 | 10000 | 3640 | 5 | 0 | 4 | 5844 | 3869 | 0.11 |
| 2-H2 | 12704 | 10000 | 3852 | 4 | 2 | 2 | 5646 | 4077 | 0.05 |
| 2-H3 | 12935 | 10000 | 3848 | 12 | 2 | 5 | 5637 | 4076 | 0.13 |
| 2-H4 | 12546 | 10000 | 3729 | 5 | 1 | 4 | 5823 | 3912 | 0.11 |
| 2-H5 | 12486 | 10000 | 3667 | 6 | 1 | 5 | 5790 | 3871 | 0.14 |
| 2-H6 | 12461 | 10000 | 3357 | 6 | 0 | 6 | 6194 | 3586 | 0.18 |
| 2-H7 | 12606 | 10000 | 3575 | 10 | 0 | 7 | 5926 | 3820 | 0.20 |

-continued

| plate-well | All Events #Events | PBLs #Events | rbIgM #Events | aMouse-PE #Events | Q1 #Events | Q2 #Events | Q3 #Events | Q4 #Events | Ratio Q2/IgM (%) |
|---|---|---|---|---|---|---|---|---|---|
| 2-H8 | 13023 | 10000 | 3172 | 21 | 3 | 10 | 6416 | 3464 | 0.32 |
| 2-H9 | 13646 | 10000 | 3461 | 291 | 42 | 162 | 5964 | 3601 | 4.68 |
| 2-H10 | 12696 | 10000 | 3218 | 7 | 2 | 5 | 6200 | 3512 | 0.16 |
| 2-H11 | 12616 | 10000 | 3593 | 8 | 1 | 4 | 6005 | 3794 | 0.11 |
| 2-H12 | 12894 | 10000 | 3569 | 8 | 1 | 3 | 5915 | 3805 | 0.08 |
| 3-A1 | 13246 | 10000 | 3811 | 5 | 0 | 5 | 5999 | 3903 | 0.13 |
| 3-A2 | 12834 | 10000 | 3971 | 9 | 1 | 7 | 5738 | 4081 | 0.18 |
| 3-A3 | 12732 | 10000 | 4061 | 2 | 0 | 1 | 5613 | 4168 | 0.02 |
| 3-A4 | 12757 | 10000 | 3865 | 8 | 1 | 3 | 5788 | 3997 | 0.08 |
| 3-A5 | 13132 | 10000 | 3774 | 11 | 3 | 7 | 5955 | 3922 | 0.19 |
| 3-A6 | 12878 | 10000 | 3441 | 11 | 0 | 6 | 6028 | 3744 | 0.17 |
| 3-A7 | 12721 | 10000 | 3622 | 6 | 1 | 4 | 5983 | 3815 | 0.11 |
| 3-A8 | 12880 | 10000 | 3813 | 9 | 1 | 6 | 5921 | 3932 | 0.16 |
| 3-A9 | 12916 | 10000 | 4189 | 15 | 1 | 12 | 5443 | 4306 | 0.29 |
| 3-A10 | 12832 | 10000 | 3908 | 2 | 0 | 2 | 5780 | 4028 | 0.05 |
| 3-A11 | 12794 | 10000 | 4168 | 4 | 0 | 4 | 5474 | 4296 | 0.10 |
| 3-A12 | 12868 | 10000 | 4260 | 2 | 0 | 2 | 5346 | 4390 | 0.05 |
| 3-B1 | 13068 | 10000 | 4099 | 14 | 1 | 7 | 5483 | 4243 | 0.17 |
| 3-B2 | 12890 | 10000 | 4027 | 6 | 0 | 6 | 5582 | 4174 | 0.15 |
| 3-B3 | 13005 | 10000 | 4125 | 16 | 2 | 9 | 5474 | 4264 | 0.22 |
| 3-B4 | 12851 | 10000 | 4072 | 10 | 1 | 5 | 5539 | 4206 | 0.12 |
| 3-B5 | 12931 | 10000 | 3747 | 9 | 0 | 8 | 6031 | 3846 | 0.21 |
| 3-B6 | 13233 | 10000 | 3538 | 22 | 4 | 13 | 6126 | 3723 | 0.37 |
| 3-B7 | 12961 | 10000 | 4189 | 3 | 0 | 3 | 5400 | 4355 | 0.07 |
| 3-B8 | 12911 | 10000 | 3989 | 9 | 3 | 5 | 5527 | 4192 | 0.13 |
| 3-B9 | 13924 | 10000 | 3849 | 16 | 7 | 6 | 5770 | 4016 | 0.16 |
| 3-B10 | 12770 | 10000 | 4238 | 11 | 0 | 8 | 5369 | 4363 | 0.19 |
| 3-B11 | 13013 | 10000 | 4087 | 6 | 0 | 4 | 5488 | 4257 | 0.10 |
| 3-B12 | 12908 | 10000 | 4023 | 10 | 0 | 8 | 5549 | 4197 | 0.20 |
| 3-C1 | 13369 | 10000 | 4092 | 3 | 1 | 1 | 5447 | 4282 | 0.02 |
| 3-C2 | 14017 | 10000 | 4064 | 15 | 7 | 5 | 5455 | 4250 | 0.12 |
| 3-C3 | 13045 | 10000 | 4067 | 9 | 1 | 6 | 5591 | 4192 | 0.15 |
| 3-C4 | 12857 | 10000 | 4145 | 9 | 4 | 5 | 5433 | 4281 | 0.12 |
| 3-C5 | 13725 | 10000 | 3895 | 10 | 0 | 7 | 5661 | 4067 | 0.18 |
| 3-C6 | 13443 | 10000 | 3726 | 36 | 11 | 18 | 5789 | 3907 | 0.48 |
| 3-C7 | 13149 | 10000 | 4191 | 16 | 1 | 10 | 5358 | 4364 | 0.24 |
| 3-C8 | 12981 | 10000 | 4291 | 7 | 0 | 6 | 5275 | 4465 | 0.14 |
| 3-C9 | 13575 | 10000 | 3885 | 99 | 14 | 23 | 5557 | 4074 | 0.59 |
| 3-C10 | 13131 | 10000 | 4178 | 11 | 0 | 7 | 5431 | 4326 | 0.17 |
| 3-C11 | 12940 | 10000 | 3988 | 8 | 0 | 8 | 5575 | 4162 | 0.20 |
| 3-C12 | 13046 | 10000 | 4159 | 4 | 1 | 3 | 5456 | 4291 | 0.07 |
| 3-D1 | 12927 | 10000 | 4046 | 6 | 1 | 4 | 5477 | 4218 | 0.10 |
| 3-D2 | 12926 | 10000 | 4171 | 14 | 0 | 9 | 5412 | 4329 | 0.22 |
| 3-D3 | 12933 | 10000 | 4120 | 6 | 3 | 2 | 5429 | 4293 | 0.05 |
| 3-D4 | 13279 | 10000 | 4191 | 15 | 2 | 10 | 5424 | 4318 | 0.24 |
| 3-D5 | 13270 | 10000 | 4037 | 8 | 0 | 6 | 5478 | 4251 | 0.15 |
| 3-D6 | 12937 | 10000 | 3984 | 8 | 2 | 3 | 5590 | 4166 | 0.08 |
| 3-D7 | 12958 | 10000 | 4002 | 9 | 1 | 4 | 5506 | 4209 | 0.10 |
| 3-D8 | 13248 | 10000 | 3938 | 12 | 2 | 7 | 5568 | 4125 | 0.18 |
| 3-D9 | 13147 | 10000 | 3921 | 8 | 2 | 4 | 5582 | 4133 | 0.10 |
| 3-D10 | 13342 | 10000 | 4227 | 12 | 2 | 6 | 5359 | 4372 | 0.14 |
| 3-D11 | 12776 | 10000 | 4108 | 7 | 0 | 5 | 5419 | 4275 | 0.12 |
| 3-D12 | 12997 | 10000 | 4118 | 8 | 2 | 6 | 5428 | 4297 | 0.15 |
| 3-E1 | 12877 | 10000 | 3911 | 8 | 0 | 6 | 5693 | 4077 | 0.15 |
| 3-E2 | 12900 | 10000 | 4058 | 7 | 0 | 4 | 5515 | 4222 | 0.10 |
| 3-E3 | 12853 | 10000 | 4023 | 8 | 0 | 5 | 5534 | 4191 | 0.12 |
| 3-E4 | 12816 | 10000 | 3876 | 18 | 7 | 11 | 5646 | 4069 | 0.28 |
| 3-E5 | 12781 | 10000 | 3616 | 11 | 2 | 6 | 5941 | 3851 | 0.17 |
| 3-E6 | 13107 | 10000 | 3972 | 12 | 2 | 3 | 5614 | 4168 | 0.08 |
| 3-E7 | 12733 | 10000 | 4090 | 8 | 2 | 4 | 5544 | 4231 | 0.10 |
| 3-E8 | 13177 | 10000 | 3792 | 9 | 3 | 5 | 5685 | 4026 | 0.13 |
| 3-E9 | 13098 | 10000 | 3955 | 10 | 1 | 6 | 5633 | 4106 | 0.15 |
| 3-E10 | 12983 | 10000 | 4129 | 5 | 1 | 4 | 5412 | 4306 | 0.10 |
| 3-E11 | 12970 | 10000 | 3891 | 10 | 0 | 9 | 5674 | 4077 | 0.23 |
| 3-E12 | 13186 | 10000 | 4022 | 9 | 2 | 7 | 5542 | 4202 | 0.17 |
| 3-F1 | 12596 | 10000 | 3638 | 8 | 0 | 6 | 5948 | 3835 | 0.16 |
| 3-F2 | 12824 | 10000 | 3550 | 8 | 0 | 7 | 6080 | 3773 | 0.20 |
| 3-F3 | 15475 | 10000 | 4156 | 861 | 42 | 581 | 5026 | 3883 | 13.98 |
| 3-F4 | 12932 | 10000 | 3995 | 3 | 0 | 3 | 5528 | 4162 | 0.08 |
| 3-F5 | 13000 | 10000 | 3988 | 7 | 1 | 5 | 5550 | 4203 | 0.13 |
| 3-F6 | 12785 | 10000 | 3998 | 10 | 1 | 5 | 5496 | 4202 | 0.13 |
| 3-F7 | 12930 | 10000 | 4280 | 10 | 1 | 7 | 5271 | 4439 | 0.16 |
| 3-F8 | 13355 | 10000 | 3862 | 22 | 3 | 15 | 5632 | 4060 | 0.39 |
| 3-F9 | 13150 | 10000 | 4209 | 10 | 1 | 7 | 5359 | 4381 | 0.17 |
| 3-F10 | 13082 | 10000 | 4179 | 10 | 1 | 8 | 5374 | 4346 | 0.19 |
| 3-F11 | 12845 | 10000 | 3998 | 10 | 0 | 9 | 5487 | 4198 | 0.23 |

-continued

| plate-well | All Events #Events | PBLs #Events | rbIgM #Events | aMouse-PE #Events | Q1 #Events | Q2 #Events | Q3 #Events | Q4 #Events | Ratio Q2/IgM (%) |
|---|---|---|---|---|---|---|---|---|---|
| 3-F12 | 13592 | 10000 | 3963 | 27 | 11 | 10 | 5520 | 4191 | 0.25 |
| 3-G1 | 12926 | 10000 | 4060 | 5 | 0 | 5 | 5429 | 4270 | 0.12 |
| 3-G2 | 12923 | 10000 | 3705 | 7 | 1 | 6 | 6012 | 3854 | 0.16 |
| 3-G3 | 12961 | 10000 | 4055 | 3 | 0 | 2 | 5486 | 4241 | 0.05 |
| 3-G4 | 12895 | 10000 | 3866 | 7 | 0 | 6 | 5701 | 4064 | 0.16 |
| 3-G5 | 12996 | 10000 | 3665 | 10 | 2 | 7 | 6001 | 3819 | 0.19 |
| 3-G6 | 12719 | 10000 | 3741 | 3 | 0 | 3 | 5831 | 3941 | 0.08 |
| 3-G7 | 13154 | 10000 | 3884 | 7 | 2 | 5 | 5857 | 4026 | 0.13 |
| 3-G8 | 13109 | 10000 | 4061 | 8 | 1 | 4 | 5462 | 4230 | 0.10 |
| 3-G9 | 12987 | 10000 | 4034 | 15 | 0 | 12 | 5563 | 4153 | 0.30 |
| 3-G10 | 13082 | 10000 | 4233 | 11 | 1 | 7 | 5360 | 4360 | 0.17 |
| 3-G11 | 13014 | 10000 | 3999 | 4 | 1 | 2 | 5503 | 4226 | 0.05 |
| 3-G12 | 13122 | 10000 | 4147 | 6 | 2 | 4 | 5396 | 4335 | 0.10 |
| 3-H1 | 12983 | 10000 | 4143 | 5 | 1 | 4 | 5373 | 4335 | 0.10 |
| 3-H2 | 12850 | 10000 | 3802 | 6 | 1 | 4 | 5889 | 3912 | 0.11 |
| 3-H3 | 13306 | 10000 | 4037 | 21 | 2 | 13 | 5502 | 4198 | 0.32 |
| 3-H4 | 12865 | 10000 | 3931 | 9 | 1 | 5 | 5627 | 4111 | 0.13 |
| 3-H5 | 12843 | 10000 | 3931 | 3 | 0 | 2 | 5631 | 4097 | 0.05 |
| 3-H6 | 13079 | 10000 | 3949 | 8 | 1 | 7 | 5530 | 4178 | 0.18 |
| 3-H7 | 13344 | 10000 | 3691 | 10 | 1 | 6 | 5993 | 3853 | 0.16 |
| 3-H8 | 12976 | 10000 | 3992 | 23 | 3 | 16 | 5620 | 4119 | 0.40 |
| 3-H9 | 13000 | 10000 | 3862 | 6 | 2 | 1 | 5791 | 4007 | 0.03 |
| 3-H10 | 12967 | 10000 | 3823 | 10 | 1 | 5 | 5781 | 3996 | 0.13 |
| 3-H11 | 12942 | 10000 | 3649 | 6 | 1 | 3 | 5895 | 3859 | 0.08 |
| 3-H12 | 13082 | 10000 | 4153 | 10 | 0 | 9 | 5425 | 4307 | 0.22 |
| 4-A1 | 12898 | 10000 | 4468 | 7 | 0 | 4 | 5087 | 4609 | 0.09 |
| 4-A2 | 12732 | 10000 | 4621 | 4 | 0 | 3 | 4927 | 4809 | 0.06 |
| 4-A3 | 12620 | 10000 | 4211 | 3 | 0 | 0 | 5278 | 4459 | 0.00 |
| 4-A4 | 12932 | 10000 | 4137 | 11 | 3 | 6 | 5375 | 4304 | 0.15 |
| 4-A5 | 12694 | 10000 | 4310 | 2 | 0 | 2 | 5214 | 4498 | 0.05 |
| 4-A6 | 12774 | 10000 | 4360 | 11 | 1 | 8 | 5194 | 4504 | 0.18 |
| 4-A7 | 12951 | 10000 | 4185 | 3 | 0 | 1 | 5329 | 4416 | 0.02 |
| 4-A8 | 12852 | 10000 | 4079 | 8 | 2 | 4 | 5512 | 4245 | 0.10 |
| 4-A9 | 13933 | 10000 | 4337 | 8 | 1 | 5 | 5165 | 4546 | 0.12 |
| 4-B1 | 12765 | 10000 | 4541 | 7 | 1 | 3 | 4989 | 4719 | 0.07 |
| 4-B2 | 12824 | 10000 | 4567 | 8 | 0 | 7 | 4982 | 4720 | 0.15 |
| 4-B3 | 12839 | 10000 | 4347 | 6 | 2 | 2 | 5142 | 4571 | 0.05 |
| 4-B4 | 12887 | 10000 | 4466 | 3 | 1 | 2 | 5057 | 4659 | 0.04 |
| 4-B5 | 13267 | 10000 | 4454 | 10 | 1 | 9 | 5112 | 4608 | 0.20 |
| 4-B6 | 12863 | 10000 | 4462 | 5 | 1 | 3 | 5035 | 4640 | 0.07 |
| 4-B7 | 12878 | 10000 | 4456 | 5 | 0 | 5 | 5118 | 4614 | 0.11 |
| 4-B8 | 13274 | 10000 | 4409 | 12 | 1 | 6 | 5102 | 4621 | 0.14 |
| 4-B9 | 12977 | 10000 | 4457 | 22 | 2 | 10 | 4998 | 4681 | 0.22 |
| 4-C1 | 12890 | 10000 | 4475 | 5 | 0 | 5 | 5048 | 4647 | 0.11 |
| 4-C2 | 12809 | 10000 | 4421 | 19 | 3 | 9 | 5073 | 4617 | 0.20 |
| 4-C3 | 12981 | 10000 | 4313 | 8 | 0 | 6 | 5177 | 4508 | 0.14 |
| 4-C4 | 13060 | 10000 | 4303 | 18 | 3 | 8 | 5144 | 4535 | 0.19 |
| 4-C5 | 12772 | 10000 | 4368 | 5 | 0 | 4 | 5100 | 4599 | 0.09 |
| 4-C6 | 13067 | 10000 | 4412 | 6 | 0 | 6 | 5072 | 4593 | 0.14 |
| 4-C7 | 12905 | 10000 | 4316 | 4 | 0 | 3 | 5165 | 4530 | 0.07 |
| 4-C8 | 12935 | 10000 | 4456 | 7 | 1 | 3 | 5054 | 4627 | 0.07 |
| 4-C9 | 12913 | 10000 | 4330 | 7 | 1 | 4 | 5197 | 4497 | 0.09 |
| 4-D1 | 12994 | 10000 | 4348 | 4 | 1 | 2 | 5112 | 4566 | 0.05 |
| 4-D2 | 12784 | 10000 | 4358 | 2 | 1 | 1 | 5123 | 4580 | 0.02 |
| 4-D3 | 12965 | 10000 | 4368 | 5 | 2 | 2 | 5160 | 4541 | 0.05 |
| 4-D4 | 12907 | 10000 | 4164 | 6 | 2 | 4 | 5217 | 4475 | 0.10 |
| 4-D5 | 12808 | 10000 | 4456 | 3 | 0 | 3 | 5033 | 4670 | 0.07 |
| 4-D6 | 12874 | 10000 | 4297 | 11 | 2 | 9 | 5182 | 4498 | 0.21 |
| 4-D7 | 13028 | 10000 | 4494 | 3 | 0 | 3 | 5026 | 4702 | 0.07 |
| 4-D8 | 13115 | 10000 | 4473 | 11 | 4 | 5 | 5020 | 4672 | 0.11 |
| 4-D9 | 12943 | 10000 | 4128 | 4 | 2 | 1 | 5399 | 4324 | 0.02 |
| 4-E1 | 12848 | 10000 | 4388 | 9 | 3 | 6 | 5129 | 4580 | 0.14 |
| 4-E2 | 12857 | 10000 | 4316 | 7 | 3 | 2 | 5191 | 4481 | 0.05 |
| 4-E3 | 13069 | 10000 | 4215 | 7 | 0 | 7 | 5242 | 4426 | 0.17 |
| 4-E4 | 12806 | 10000 | 3628 | 5 | 0 | 4 | 5879 | 3896 | 0.11 |
| 4-E5 | 13017 | 10000 | 4111 | 6 | 1 | 5 | 5370 | 4314 | 0.12 |
| 4-E6 | 12819 | 10000 | 4059 | 8 | 0 | 6 | 5466 | 4249 | 0.15 |
| 4-E7 | 14819 | 10000 | 4172 | 67 | 0 | 26 | 5434 | 4370 | 0.62 |
| 4-E8 | 12956 | 10000 | 3806 | 9 | 0 | 8 | 5834 | 3957 | 0.21 |
| 4-E9 | 12876 | 10000 | 3739 | 9 | 0 | 8 | 6016 | 3869 | 0.21 |
| 4-F1 | 12800 | 10000 | 4371 | 8 | 1 | 7 | 5116 | 4529 | 0.16 |
| 4-F2 | 12973 | 10000 | 4180 | 8 | 0 | 8 | 5309 | 4396 | 0.19 |
| 4-F3 | 12991 | 10000 | 4256 | 5 | 1 | 3 | 5185 | 4489 | 0.07 |
| 4-F4 | 12997 | 10000 | 4089 | 11 | 1 | 6 | 5335 | 4323 | 0.15 |
| 4-F5 | 12936 | 10000 | 4236 | 8 | 2 | 4 | 5269 | 4418 | 0.09 |
| 4-F6 | 12940 | 10000 | 4244 | 8 | 1 | 3 | 5266 | 4441 | 0.07 |

-continued

| plate-well | All Events #Events | PBLs #Events | rbIgM #Events | aMouse-PE #Events | Q1 #Events | Q2 #Events | Q3 #Events | Q4 #Events | Ratio Q2/IgM (%) |
|---|---|---|---|---|---|---|---|---|---|
| 4-F7 | 13035 | 10000 | 4125 | 9 | 1 | 7 | 5352 | 4320 | 0.17 |
| 4-F8 | 12882 | 10000 | 3876 | 6 | 1 | 5 | 5620 | 4098 | 0.13 |
| 4-F9 | 12622 | 10000 | 3644 | 4 | 1 | 3 | 5996 | 3812 | 0.08 |
| 4-G1 | 13075 | 10000 | 4332 | 54 | 1 | 25 | 5176 | 4487 | 0.58 |
| 4-G2 | 12861 | 10000 | 4301 | 7 | 1 | 5 | 5177 | 4471 | 0.12 |
| 4-G3 | 12762 | 10000 | 3976 | 5 | 1 | 3 | 5637 | 4121 | 0.08 |
| 4-G4 | 12636 | 10000 | 3666 | 8 | 0 | 6 | 6007 | 3814 | 0.16 |
| 4-G5 | 12574 | 10000 | 3771 | 4 | 0 | 3 | 5898 | 3931 | 0.08 |
| 4-G6 | 12858 | 10000 | 3864 | 2 | 0 | 1 | 5832 | 4015 | 0.03 |
| 4-G7 | 12841 | 10000 | 3731 | 5 | 0 | 3 | 5839 | 3957 | 0.08 |
| 4-H1 | 12964 | 10000 | 4150 | 4 | 1 | 2 | 5346 | 4321 | 0.05 |
| 4-H2 | 13080 | 10000 | 4247 | 24 | 0 | 7 | 5169 | 4479 | 0.16 |
| 4-H3 | 12963 | 10000 | 4440 | 5 | 0 | 4 | 5052 | 4621 | 0.09 |
| 4-H4 | 12653 | 10000 | 3928 | 6 | 1 | 4 | 5529 | 4136 | 0.10 |
| 4-H5 | 13038 | 10000 | 4096 | 9 | 2 | 5 | 5381 | 4303 | 0.12 |
| 4-H6 | 12987 | 10000 | 3918 | 3 | 0 | 2 | 5514 | 4181 | 0.05 |
| 4-H7 | 12894 | 10000 | 4068 | 4 | 1 | 3 | 5414 | 4266 | 0.07 |

The invention is based at least in part on the finding that a specific immunization protocol has to be followed to obtain an anti-rabbit CD19 antibody expressing B-cell or hybridoma, respectively. It has been found that with the combination of DNA-immunization and a boost with a cell expressing rabbit CD19 on its surface prior to harvest a B-cell can be obtained that expresses a rabbit CD19 specific antibody.

Without being bound by this theory it is assumed that no anti-rabbit CD19 antibody, let alone a monoclonal antibody, was available until now because such an antibody is really difficult to generate. For example, experience revealed that immunization with CD19 as a recombinant protein or solely as a recombinant cell line does not lead to antibodies binding native CD19 on B cells. Therefore, DNA only immunization including final cellular boost was performed assuming that CD19 being present in the animal as a native confirmation.

Herein are provided antibodies against rabbit CD19 which are useful as tool for the labeling and enrichment/selection of rabbit B-cells.

Without being bound by this theory it is assumed that these antibodies can be used amongst other things beneficially after macrophage depletion and/or for staining of IgM-IgG+CD19+-B-cells.

The invention is based at least in part on the finding that CD19 can be used to label B-cells for single cell deposition or pool sorting. It has been found that all B-cells producing antigen-specific IgG were CD19-positive on the day of the deposition or sorting, respectively. Thus, CD19 on rabbit cells can be used to select antigen-specific antibody producing B-cells (see FIGS. 3A-3D and the following table).

| Plates | count [n] | kind |
|---|---|---|
| 8 | 14 | antigen-specific |
|  | 48 | IgG-positive wells |
|  | 84 | sorted cells |
| 7 | 16 | antigen-specific |
|  | 59 | IgG-positive wells |
|  | 84 | sorted cells |
| 6 | 19 | antigen-specific |
|  | 57 | IgG-positive wells |
|  | 84 | sorted cells |
| 5 | 13 | antigen-specific |
|  | 56 | IgG-positive wells |
|  | 84 | sorted cells |

-continued

| Plates | count [n] | kind |
|---|---|---|
| 4 | 17 | antigen-specific |
|  | 55 | IgG-positive wells |
|  | 84 | sorted cells |
| 3 | 13 | antigen-specific |
|  | 44 | IgG-positive wells |
|  | 84 | sorted cells |
| 2 | 18 | antigen-specific |
|  | 56 | IgG-positive wells |
|  | 84 | sorted cells |
| 1 | 18 | antigen-specific |
|  | 47 | IgG-positive wells |
|  | 84 | sorted cells |

The anti-rabbit CD19 antibody according to the current invention can be used to detect IgG- and IgM-positive B-cells whereby all antigen specific IgG-positive B-cells have high levels of CD19. With the antibody according to the invention it could be determined for the first time that of the B-cells in spleen about 5.4% of total cells were CD19-positive and in peripheral blood mononucleated cells (PBMCs) on average 38.7% of total cells were CD19-positive. It has to be pointed out that the percentage of rabbit CD19-positive cells in rabbit PBMCs, freshly isolated from blood, is higher than the sum of the immunoglobulin-stained B-cells implying that the anti-rabbit CD19 antibody is a superior marker for labeling all rabbit B-cells. The results are presented in the following tables.

| from blood population | total | % | % of total |
|---|---|---|---|
| all events | 13826 |  | 100.0 |
| lymphocytes | 9330 | 67.5 (of parent) | 67.5 |
| CD 19-positive | 5787 | 64.5 (of parent) | 41.9 |
| IgG-positive | 102 | 1.1 (of CD19+) | 0.7 |
| IgM-positive | 3818 | 42.6 (of CD19+) | 27.6 |

| from spleen population | total | % | % of total |
|---|---|---|---|
| all events | 27654 | | 100.0 |
| lymphocytes | 9177 | 33.2 (of parent) | 33.2 |
| live, single cells | 7474 | 81.4 (of parent) | 27.0 |
| CD 19-positive | 1817 | 24.3 (of parent) | 6.6 |
| IgG-positive | 46 | 0.6 (of CD19+) | 0.2 |
| IgM-positive | 1126 | 15.1 (of CD19+) | 4.1 |

Especially for the IgG sorted B-cell population it is important that all IgG-positive cells have high levels of CD19 (see data in the following Table).

| from blood population | total | % | % of total |
|---|---|---|---|
| all events | 14460 | | 100.0 |
| lymphocytes | 8486 | 58.69 (of parent) | 58.69 |
| live, single cells | 8087 | 95.30 (of parent) | |
| CD 19-positive | 5404 | 66.82 (of parent) | 37.37 |
| IgG-positive | 79 | 0.98 (of CD19+) | 0.55 |
| CD19– and IgG-double positive | 79 | 0.98 (of CD19+) | 0.55 |

The invention is based at least in part on the finding that CD19 can be used to differentiate B-cells from feeder cells in a B-cell co-cultivation. Single deposited B-cells require the presence of feeder cells in the cultivation for growth and cell division. Although feeder cells are irradiated prior to co-cultivation with B-cells to reduce their growth and cell division the total number thereof and the cell size is in the same order of magnitude as the number and the cell size of B-cells obtained after the co-cultivation. With the anti-rabbit CD19 antibody according to the current invention it is now possible to differentiate between feeder cells and B-cells by simple FACS analysis after co-cultivation. Thereby the total number of B-cells can be identified. This allows for the normalization of other cultivation parameters, such as antibody production rate or yield (see FIGS. 4A-4C and 5A-5C).

Prior to the current invention it was not possible to estimate the size of the grown B-cell clone after culture in terms of B-cell count since rabbit IgG as a cell surface B-cell marker is not suitable as its expression decreases during culture and therefore cannot be used as a B-cell marker. The use of the anti-rabbit CD19 antibody according to the current invention solves this problem as rabbit CD19 is still expressed on the B-cells after culture and thereby enables to count the B-cells after culture (B cells/well=Event Nbr in CD19+ gate/volume Facsed×sample volume).

In the following Table the B-cell counts (CD19-positive PI-cells) of 36 single wells after cultivation are shown. The B-cell counts were over a broad range. The calculation CD19-positive B-cell count was done as follows: Count in FACS gate/150 (volume Facsed)*200 (total sample volume).

| Sample ID | Lymphocyte population in FSC-SSC | B-cells CD19+ | Count in FACS gate | absoloute CD19+ B-cell count, calculated | Live CD19+ | Mean (Alexa Fluor 647-A) | IgG conc. [µg/ml] | antigen-binding OD |
|---|---|---|---|---|---|---|
| C3 | 11266 | 10822 | 14429 | 7290 | 7.50 | −0.01 |
| C4 | 309 | 62 | 83 | 4764 | 0.77 | 0.00 |
| C5 | 450 | 247 | 329 | 5726 | 2.73 | 0.00 |
| C6 | 6396 | 5782 | 7709 | 11085 | 4.24 | 0.00 |
| C7 | 514 | 239 | 319 | 5713 | 4.29 | 2.46 |
| C8 | 454 | 135 | 180 | 6424 | 2.11 | 1.91 |
| C9 | 535 | 188 | 251 | 5864 | 4.18 | −0.01 |
| C10 | 3293 | 2684 | 3579 | 7400 | 3.08 | −0.01 |
| C11 | 261 | 8 | 11 | 3753 | 0.57 | 0.75 |
| D3 | 166 | 3 | 4 | 4712 | 0.01 | −0.01 |
| D4 | 355 | 138 | 184 | 6336 | 1.27 | 0.01 |
| D5 | 7524 | 6921 | 9228 | 10148 | 6.31 | 0.00 |
| D6 | 3391 | 2807 | 3743 | 4844 | 7.50 | −0.01 |
| D7 | 137 | 0 | 0 | n/a | 0.01 | 0.00 |
| D8 | 25411 | 24404 | 32539 | 10873 | 7.50 | 2.80 |
| D9 | 2034 | 1298 | 1731 | 9104 | 7.50 | −0.01 |
| D10 | 1119 | 638 | 851 | 5851 | 7.50 | −0.01 |
| D11 | 417 | 5 | 7 | 6100 | 0.19 | −0.01 |
| E3 | 13550 | 12504 | 16672 | 7804 | 7.50 | 2.69 |
| E4 | 6136 | 5402 | 7203 | 6152 | 7.50 | 0.02 |
| E5 | 343 | 160 | 213 | 5470 | 3.82 | 0.02 |
| E6 | 10228 | 8379 | 11172 | 10324 | 7.50 | 0.06 |
| E7 | 209 | 0 | 0 | n/a | 0.01 | 0.01 |
| E8 | 475 | 254 | 339 | 6318 | 5.44 | 0.02 |
| E9 | 4719 | 3873 | 5164 | 17049 | 0.48 | 0.01 |
| E10 | 5436 | 4948 | 6597 | 8346 | 6.80 | 2.27 |
| E11 | 6928 | 5791 | 7721 | 5301 | 7.50 | 2.52 |
| F3 | 3908 | 3627 | 4836 | 8155 | 7.50 | 0.01 |
| F4 | 3382 | 2773 | 3697 | 8696 | 5.78 | 0.01 |
| F5 | 584 | 284 | 379 | 5625 | 1.22 | 0.00 |
| F6 | 1294 | 664 | 885 | 3806 | 7.50 | 0.00 |
| F7 | 3164 | 2514 | 3352 | 6052 | 7.50 | 0.00 |
| F8 | 2514 | 1992 | 2656 | 9539 | 7.40 | 0.00 |
| F9 | 8436 | 7602 | 10136 | 6443 | 7.50 | 2.98 |
| F10 | 1568 | 985 | 1313 | 5174 | 7.50 | −0.01 |
| F11 | 271 | 6 | 8 | 4936 | 0.01 | 0.00 |

Every time a B-cell clone is present, CD19-positive B-cells could be detected and counted omitting live feeder cells. It can be seen that the cell count (=total number of cells) of the B-cell clones are very heterogeneous over a broad range.

The size of the B-cell clone is a very suitable surrogate marker for the success of the B-cell proliferation. In addition, the size of the B-cell clone can be correlated with the previous sorted B-cell population and the ELISA results enabling better characterization of the system.

Furthermore, it is possible to identify slow growing as well as low producing B-cells, especially in the large excess of feeder cells. At the same time dead feeder cells do not interfere with the staining and analysis/selection process. Due to this specific labelling the counting of B-cells in the presence of (dead or alive) feeder cells is possible directly in the cultivation, e.g. in a well of a multi-well plate.

The invention is based at least in part on the finding that CD19 level on the surface of the cell upon deposition is positively correlated to the obtained IgG titer after cultivation. This correlation can be used for the selection of high-producing B-cells directly after isolation from the rabbit and without the need to perform a co-cultivation.

The invention is based at least in part on the finding that CD19 can be used to enrich rabbit B-cells and thereby increase the B-cell population for single cell sort, e.g. IgG+ B-cell population, and thereby decreasing number of undesired cells. Without being bound by this theory, this property can result amongst other things in improved sorting results.

The invention is based at least in part on the finding that the anti-rabbit CD19 antibody according to the invention can be used for the identification of primary rabbit B-cells.

With the antibodies according to the invention it was possible to determine the fraction of CD19 positive B-cells in samples, such as e.g. in rabbit PBMCs or rabbit splenocytes. The results for PBMCs are shown in the following Table.

| population | number [n] | fraction of total [%] |
|---|---|---|
| all cells | 21,510 | 100 |
| CD19 positive | 7,904 | 36.7 |
| IgM positive | 6,835 | 31.8 |
| IgG positive | 71 | 0.3 |

Figure 6A:
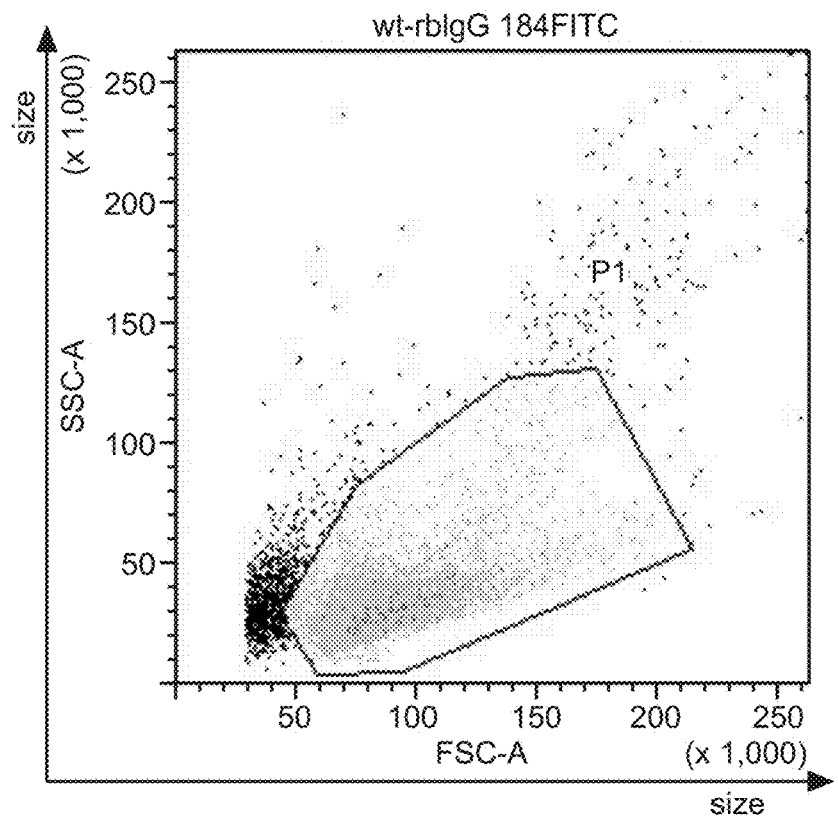
Figure 6B:
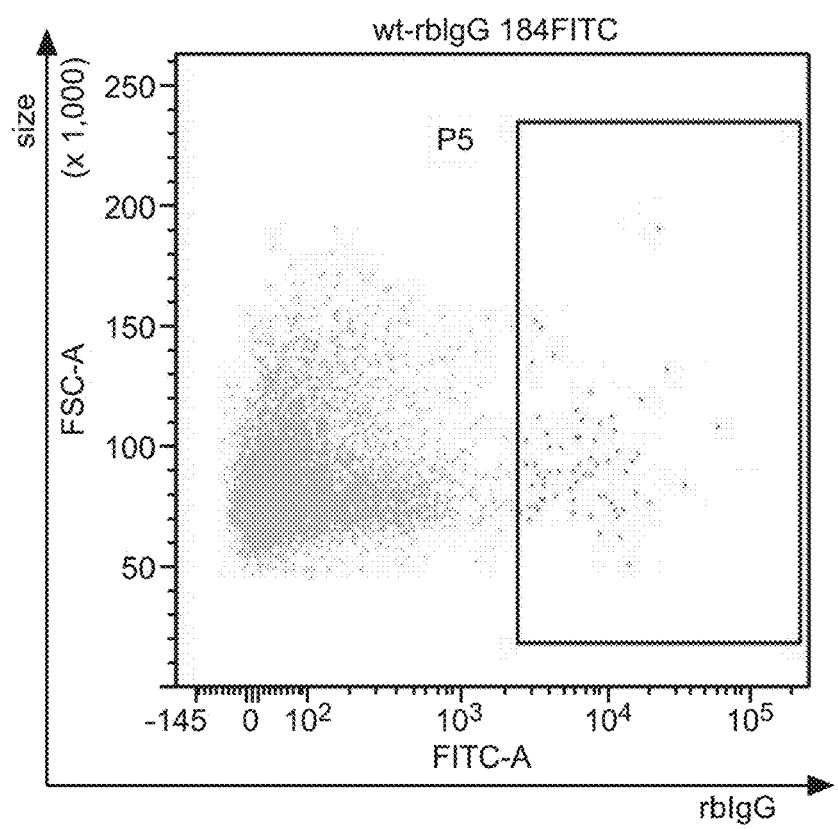

A commercially available goat anti-rabbit IgG polyclonal antibody (AbD Serotec STAR121F) conjugated to FITC labels between 0.2% and 2% of rabbit PBMCs (FIGS. 6A-6C).

Cells were double stained with an FITC-labelled anti-IgG antibody and the anti-rabbit CD19 antibody according to the invention labelled with APC. Cell were subsequently Index-sorted for FSC and IgG. Results show that only CD19 and IgG positive cells produced IgG in a subsequent ELISA. It was then checked for the percentage of CD19 positive cells that were sorted. This was used as a measure to estimate by how much sorting efficiency could be improved by using the antibody according to the invention. On average, efficiency can be improved by about 14% when only sorting IgG and CD19 double positive cells, and in the best cases with over 20% without any significant loss in IgG positive or antigen-specific cells. The results are shown in the following Table.

| Samples | Percentage of antigen-specific IgG producing cells in IgG/CD19-double positive cells |
|---|---|
| 1 | 90.9% |
| 2 | 97.7% |
| 3 | 77.3% |
| 4 | 80.9% |

Different conditions for a bead-based selection/extraction process have been tested as follows:
- magnetic bead based panning with biotinylated antigen and streptavidin beads, followed by sorting gating for FSC and IgG (FITC) and CD19 (APC) double stained cells, and
- magnetic bead based panning with biotinylated anti-CD19 antibody according to the invention and streptavidin beads, followed by sorting gating for FCS and IgG (FITC) and antigen (APC) double stained cells.

In both cases life-dead staining was performed with 7AAD.

It has been found that panning with the anti-CD19 antibody according to the invention results in increased viability (4 times higher) of B-cells. Without being bound by this theory it is assumed that the increased viability might be caused because of reduced cross-linking and activation.

The invention is based, at least in part, on the finding that by using an anti-CD19 antibody according to the invention in a panning step for enriching B-cells from a population of cells, a higher percentage of sorted B-cell are producing an antibody specific for the antigen as shown in a subsequent ELISA. Additionally, there are also less cells positive in a cross-reactivity assay, resulting in a higher number of clones that can be used. This might be related to the increased viability of the cells.

The results obtained with B-cells from different immunization campaigns (different antigens) are shown in the following Table.

| antigen 1 | IgG-positive cells after panning | antigen-specific IgG producing cells after panning |
|---|---|---|
| antigen panning | 55.8% | 45.6% |
| anti-CD19 antibody panning | 69.9% | 61.8% |

| antigen 2 | IgG-positive cells after panning | antigen-specific IgG producing cells after panning | cells producing cross reactive antibody |
|---|---|---|---|
| antigen panning | 21.5% | 16.8% | 29.1% |
| anti-CD19 antibody panning | 33.9% | 15.3% | 14.9% |

A. Exemplary Anti-Rabbit CD19 Antibodies and Uses Thereof

A.1 Exemplary Antibodies

It has been found that rabbit CD19 is an advantageous cell surface marker for the analysis and characterization of rabbit B-cells. The labelling of rabbit B-cells via surface presented CD19 allows for an improved B-cell sorting. The improvement is in, amongst other things, a more specific labelling and thereby sorting/single cell deposition or/and a facilitated process wherein the number of B-cells to be processed is reduced and at the same time the number of B-cells producing an antigen-specific antibody is increased.

In one aspect, herein is provided an isolated antibody that specifically bind to rabbit CD19 comprising at least one, two, three, four, five, or six HVRs selected from (a) HVR-H1 comprising the amino acid sequence of SEQ ID NO: 32 or 33 or 34, (b) HVR-H2 comprising the amino acid sequence of SEQ ID NO: 35 or 36, (c) HVR-H3 comprising the amino acid sequence of SEQ ID NO: 37, (d) HVR-L1 comprising the amino acid sequence of SEQ ID NO: 38, (e) HVR-L2 comprising the amino acid sequence of SEQ ID NO: 39, and (0 HVR-L3 comprising the amino acid sequence of SEQ ID NO: 40.

In one aspect, herein is provided an anti-rabbit CD19 antibody comprising at least one, two, three, four, five, or six HVRs selected from (a) HVR-H1 comprising the amino acid sequence of SEQ ID NO: 33, (b) HVR-H2 comprising the amino acid sequence of SEQ ID NO: 36, (c) HVR-H3 comprising the amino acid sequence of SEQ ID NO: 37, (d) HVR-L1 comprising the amino acid sequence of SEQ ID NO: 38, (e) HVR-L2 comprising the amino acid sequence of SEQ ID NO: 39, and (f) HVR-L3 comprising the amino acid sequence of SEQ ID NO: 40.

In one aspect, herein is provided an anti-rabbit CD19 antibody comprising at least one, two, three, four, five, or six HVRs selected from (a) HVR-H1 comprising the amino acid sequence of SEQ ID NO: 32, (b) HVR-H2 comprising the amino acid sequence of SEQ ID NO: 35, (c) HVR-H3 comprising the amino acid sequence of SEQ ID NO: 37, (d)

HVR-L1 comprising the amino acid sequence of SEQ ID NO: 38, (e) HVR-L2 comprising the amino acid sequence of SEQ ID NO: 39, and (f) HVR-L3 comprising the amino acid sequence of SEQ ID NO: 40.

In one aspect, herein is provided an anti-rabbit CD19 antibody comprising at least one, two, three, four, five, or six HVRs selected from (a) HVR-H1 comprising the amino acid sequence of SEQ ID NO: 34, (b) HVR-H2 comprising the amino acid sequence of SEQ ID NO: 36, (c) HVR-H3 comprising the amino acid sequence of SEQ ID NO: 37, (d) HVR-L1 comprising the amino acid sequence of SEQ ID NO: 38, (e) HVR-L2 comprising the amino acid sequence of SEQ ID NO: 39, and (f) HVR-L3 comprising the amino acid sequence of SEQ ID NO: 40.

In one aspect, herein is provided an isolated antibody that specifically bind to rabbit CD19 comprising (a) a HVR-H1 comprising the amino acid sequence of SEQ ID NO: 32 or 33 or 34, (b) a HVR-H2 comprising the amino acid sequence of SEQ ID NO: 35 or 36, (c) a HVR-H3 comprising the amino acid sequence of SEQ ID NO: 37, (d) a HVR-L1 comprising the amino acid sequence of SEQ ID NO: 38, (e) a HVR-L2 comprising the amino acid sequence of SEQ ID NO: 39, and (0 a HVR-L3 comprising the amino acid sequence of SEQ ID NO: 40.

In one aspect, herein is provided an anti-rabbit CD19 antibody comprising (a) a HVR-H1 comprising the amino acid sequence of SEQ ID NO: 33, (b) a HVR-H2 comprising the amino acid sequence of SEQ ID NO: 36, (c) a HVR-H3 comprising the amino acid sequence of SEQ ID NO: 37, (d) a HVR-L1 comprising the amino acid sequence of SEQ ID NO: 38, (e) a HVR-L2 comprising the amino acid sequence of SEQ ID NO: 39, and (0 a HVR-L3 comprising the amino acid sequence of SEQ ID NO: 40.

In one aspect, herein is provided an anti-rabbit CD19 antibody comprising (a) a HVR-H1 comprising the amino acid sequence of SEQ ID NO: 32, (b) a HVR-H2 comprising the amino acid sequence of SEQ ID NO: 35, (c) a HVR-H3 comprising the amino acid sequence of SEQ ID NO: 37, (d) a HVR-L1 comprising the amino acid sequence of SEQ ID NO: 38, (e) a HVR-L2 comprising the amino acid sequence of SEQ ID NO: 39, and (0 a HVR-L3 comprising the amino acid sequence of SEQ ID NO: 40.

In one aspect, herein is provided an anti-rabbit CD19 antibody comprising (a) a HVR-H1 comprising the amino acid sequence of SEQ ID NO: 34, (b) a HVR-H2 comprising the amino acid sequence of SEQ ID NO: 36, (c) a HVR-H3 comprising the amino acid sequence of SEQ ID NO: 37, (d) a HVR-L1 comprising the amino acid sequence of SEQ ID NO: 38, (e) a HVR-L2 comprising the amino acid sequence of SEQ ID NO: 39, and (0 a HVR-L3 comprising the amino acid sequence of SEQ ID NO: 40.

In another aspect, the anti-rabbit CD19 antibody as reported herein comprises (i) a VH domain comprising at least one, at least two, or all three VH HVR sequences selected from (a) HVR-H1 comprising the amino acid sequence of SEQ ID NO: 32 or 33 or 34, (b) HVR-H2 comprising the amino acid sequence of SEQ ID NO: 35 or 36, (c) HVR-H3 comprising the amino acid sequence of SEQ ID NO: 37, and (ii) a VL domain comprising at least one, at least two, or all three VL HVR sequences selected from (a) HVR-L1 comprising the amino acid sequence of SEQ ID NO: 38, (b) HVR-L2 comprising the amino acid sequence of SEQ ID NO: 39, and (c) HVR-L3 comprising the amino acid sequence of SEQ ID NO: 40.

In another aspect, the anti-rabbit CD19 antibody as reported herein comprises (i) a VH domain comprising at least one, at least two, or all three VH HVR sequences selected from (a) HVR-H1 comprising the amino acid sequence of SEQ ID NO: 33, (b) HVR-H2 comprising the amino acid sequence of SEQ ID NO: 36, (c) HVR-H3 comprising the amino acid sequence of SEQ ID NO: 37, and (ii) a VL domain comprising at least one, at least two, or all three VL HVR sequences selected from (a) HVR-L1 comprising the amino acid sequence of SEQ ID NO: 38, (b) HVR-L2 comprising the amino acid sequence of SEQ ID NO: 39, and (c) HVR-L3 comprising the amino acid sequence of SEQ ID NO: 40.

In another aspect, the anti-rabbit CD19 antibody as reported herein comprises (i) a VH domain comprising at least one, at least two, or all three VH HVR sequences selected from (a) HVR-H1 comprising the amino acid sequence of SEQ ID NO: 32, (b) HVR-H2 comprising the amino acid sequence of SEQ ID NO: 35, (c) HVR-H3 comprising the amino acid sequence of SEQ ID NO: 37, and (ii) a VL domain comprising at least one, at least two, or all three VL HVR sequences selected from (a) HVR-L1 comprising the amino acid sequence of SEQ ID NO: 38, (b) HVR-L2 comprising the amino acid sequence of SEQ ID NO: 39, and (c) HVR-L3 comprising the amino acid sequence of SEQ ID NO: 40.

In another aspect, the anti-rabbit CD19 antibody as reported herein comprises (i) a VH domain comprising at least one, at least two, or all three VH HVR sequences selected from (a) HVR-H1 comprising the amino acid sequence of SEQ ID NO: 34, (b) HVR-H2 comprising the amino acid sequence of SEQ ID NO: 36, (c) HVR-H3 comprising the amino acid sequence of SEQ ID NO: 37, and (ii) a VL domain comprising at least one, at least two, or all three VL HVR sequences selected from (a) HVR-L1 comprising the amino acid sequence of SEQ ID NO: 38, (b) HVR-L2 comprising the amino acid sequence of SEQ ID NO: 39, and (c) HVR-L3 comprising the amino acid sequence of SEQ ID NO: 40.

In another aspect, an anti-rabbit CD19 antibody is provided that is a humanized antibody. In one embodiment, the humanized anti-rabbit CD19 antibody comprises HVRs as in any of the above embodiments, and further comprises an acceptor human framework, e.g. a human immunoglobulin (germline) framework or a human consensus framework.

In a further aspect, herein is provided an antibody that binds to the same epitope as an anti-rabbit CD19 antibody as reported herein. For example, in certain embodiments, an antibody is provided that binds to the same epitope as an anti-rabbit CD19 antibody comprising a VH sequence of SEQ ID NO: 30 and a VL sequence of SEQ ID NO: 26.

In one embodiment, an anti-rabbit CD19 antibody according to any of the above embodiments is a monoclonal antibody. In one embodiment, an anti-rabbit CD19 antibody is an antibody fragment, e.g., an Fv, Fab, Fab', scFv, diabody, or F(ab')$_2$ fragment. In another embodiment, the antibody is a full length antibody, e.g., an intact IgG1 or IgG 4 antibody or other antibody class or isotype as defined herein.

In one embodiment of all aspects the antibody comprises (all positions according to EU index of Kabat)
  i) a homodimeric Fc-region of the human IgG1 subclass optionally with the mutations P329G, L234A and L235A, or
  ii) a homodimeric Fc-region of the human IgG4 subclass optionally with the mutations P329G, S228P and L235E, or
  iii) a homodimeric Fc-region of the human IgG1 subclass with the mutations (P329G, L234A, L235A) I253A, H310A, and H435A, or with the mutations (P329G, L234A, L235A) H310A, H433A, and Y436A, or iv) a heterodimeric Fc-region whereof
   a) one Fc-region polypeptide comprises the mutation T366W, and the other Fc-region polypeptide comprises the mutations T366S, L368A and Y407V, or
   b) one Fc-region polypeptide comprises the mutations T366W and Y349C, and the other Fc-region polypeptide comprises the mutations T366S, L368A, Y407V, and S354C, or
   c) one Fc-region polypeptide comprises the mutations T366W and S354C, and the other Fc-region polypeptide comprises the mutations T366S, L368A, Y407V and Y349C,
   or
v) a heterodimeric Fc-region of the human IgG1 subclass whereof both Fc-region polypeptides comprise the mutations P329G, L234A and L235A and
   a) one Fc-region polypeptide comprises the mutation T366W, and the other Fc-region polypeptide comprises the mutations T366S, L368A and Y407V, or
   b) one Fc-region polypeptide comprises the mutations T366W and Y349C, and the other Fc-region polypeptide comprises the mutations T366S, L368A, Y407V, and S354C, or
   c) one Fc-region polypeptide comprises the mutations T366W and S354C, and the other Fc-region polypeptide comprises the mutations T366S, L368A, Y407V and Y349C,
   or
vi) a heterodimeric Fc-region of the human IgG4 subclass whereof both Fc-region polypeptides comprise the mutations P329G, S228P and L235E and
   a) one Fc-region polypeptide comprises the mutation T366W, and the other Fc-region polypeptide comprises the mutations T366S, L368A and Y407V, or
   b) one Fc-region polypeptide comprises the mutations T366W and Y349C, and the other Fc-region polypeptide comprises the mutations T366S, L368A, Y407V, and S354C, or
   c) one Fc-region polypeptide comprises the mutations T366W and S354C, and the other Fc-region polypeptide comprises the mutations T366S, L368A, Y407V and Y349C, or
   vii) a combination of one of iii) with one of vi), v) and vi).

In a further aspect, an anti-rabbit CD19 antibody according to any of the above embodiments may incorporate any of the features, singly or in combination, as described in the sections below:

1. Antibody Fragments

In certain embodiments, an antibody provided herein is an antibody fragment. Antibody fragments include, but are not limited to, Fab, Fab', Fab'-SH, F(ab')₂, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. E. coli or phage), as described herein.

2. Chimeric and Humanized Antibodies

An antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

A humanized antibody is a chimeric antibody is. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633; and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

3. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in the Table below under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue.

Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody as reported herein may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc-region residues according to Kabat); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, herein is provided an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

A.2 Exemplary Uses

The anti-rabbit CD-19 antibody according to the invention can be used in any method that requires the specific labelling and detection of rabbit B-cells.

The individual methods are for
i) the isolation of a B-cell or a B-cell clone from a population of B-cells or other cells, whereby the isolated B-cell or B-cell clone produces an antibody specifically binding to a target,
ii) the co-cultivation of single deposited B-cells,
iii) the labeling of B-cells for counting and selection/deposition, and
iv) the production of an antibody.

Concomitantly with the methods also the corresponding uses are also encompassed and disclosed.

One aspect is a method for selecting a B-cell comprising the following steps:
a) obtaining B-cells from the blood of a rabbit,
b) incubating the B-cells with an antibody according to the current invention,
c) selecting one or more B-cells to which the antibody according to the invention is bound.

In one embodiment the method further comprises one or more of the following steps:
after step b) and prior to step c): incubating the B-cells at 37° C. for one hour in co-cultivation medium,
c) depositing one or more B-cells to which the antibody according to the invention is bound (in an individual container),
d) co-cultivating the deposited cells with a feeder cell in a co-cultivation medium,
e) selecting a B-cell proliferating in step d) and thereby selecting a B-cell.

One aspect as reported herein is a method for selecting a B-cell comprising the following steps:
a) co-cultivating each of the B-cells of a population of B-cells, which has been deposited by FACS as single cell based on the binding of a labelled antibody according to the current invention thereto, with murine EL-4 B5 cells as feeder cells, and
b) selecting a B-cell clone proliferating and secreting antibody in step a).

One aspect as reported herein is a method for producing an antibody binding to a target antigen comprising the following steps
a) co-cultivating one or more B-cells of a population of B-cells, which has/have been deposited by FACS in an individual container based on the binding of a labelled antibody according to the current invention thereto, optionally in the presence of murine EL-4 B5 cells as feeder cells and IL-1β, TNFα, IL-10, and one or more selected from IL-21, SAC, BAFF, IL-2, IL-4, and IL-6 as feeder mix,
b) selecting a B-cell clone producing an antibody specifically binding to the target antigen,
b1) determining the nucleic acid sequence encoding the variable light chain domain and the variable heavy chain domain of the antibody by a reverse transcriptase PCR,
b2) transfecting a cell with a nucleic acid comprising the nucleic acid sequence encoding the antibody variable light chain domain and the variable heavy chain domain,
c) cultivating the cell, which contains the nucleic acid that encodes the antibody produced by the B-cell clone selected in step b) or a humanized variant thereof, and recovering the antibody from the cell or the cultivation supernatant and thereby producing the antibody.

One aspect as reported herein is a method for co-cultivating one or more rabbit B-cells comprising the steps of
incubating a multitude of rabbit B-cells/labelling individual B-cells of a multitude of rabbit B-cells with an antibody according to the current invention that is conjugated to a detectable label,
selecting/depositing one or more rabbit B-cells that have the antibody according to the invention bound to their surface/that have been labelled either as individual B-cells (single deposited B-cell) or as a pool of B-cells, and
co-cultivating the single deposited rabbit B-cells or the pool of rabbit B-cells with feeder cells,
optionally incubating after the co-cultivation the obtained cell mixture with an antibody according to the current invention that is conjugated to a detectable label and selecting/depositing/counting rabbit B-cells that have the antibody according to the invention bound to their surface/that have been labelled.

One aspect of the current invention is a method for removing non B-cells for a mixture of cells, such as e.g. a cultivation, comprising the following steps:
- a) co-cultivating a single deposited B-cell or a pool of B-cells with feeder cells,
- b) incubating the cells from the co-cultivation obtained in step a) with the antibody according to the invention, and
- c) selecting one or more cells to which the antibody according to the invention is bound and thereby selecting B-cells and removing non-B-cells from a mixture of cells.

One aspect according to the current invention is a method for determining the number B-cells in a co-cultivation of a single deposited B-cell with feeder cells comprising the following steps:
- a) co-cultivating a single deposited B-cell with feeder cells,
- b) incubating the cells from the co-cultivation obtained in step a) with the antibody according to the invention, and
- c) determining the number of B-cells in the cultivation by counting the number of cells to which the antibody according to the invention is bound.

In one embodiment of all corresponding aspects or embodiments the co-cultivating is in the presence of a synthetic feeder mix that comprises IL-1β, TNFα, IL-10, and one or more selected from IL-21, SAC, BAFF, IL-2, IL-4, and IL-6.

In one embodiment of all corresponding aspects or embodiments the feeder cells are EL-4 B5 cells.

In one embodiment of all corresponding aspects or embodiments the number of feeder cells (at the start of the co-cultivation) is less than $5\times10^4$ per B-cell.

In one embodiment of all corresponding aspects or embodiments the feeder cells have been irradiated prior to the co-cultivation. In one embodiment the irradiation is with a dose of about 50 Gy or less. In one embodiment the irradiation is with a dose of 9.5 Gy or less and more than 0 Gy.

In one embodiment of all corresponding aspects or embodiments the number of EL-4 B5 cells is less than $1\times10^4$ EL-4 B5 cells per B-cell (whereby in this embodiment the irradiation is with 0 Gy). In one embodiment the number of EL-4 B5 cells is less than $7.5\times10^3$ EL-4 B5 cells per B-cell.

In one embodiment of all corresponding aspects or embodiments the co-cultivating is additionally in the presence of a feeder mix.

In one embodiment of all corresponding aspects or embodiments the feeder mix (cytokine mix, CM) comprises one or more of
- i) interleukin-1 beta and tumor necrosis factor alpha,
- ii) interleukin-2 (IL-2) and/or interleukin-10 (IL-10),
- iii) *Staphylococcus aureus* strain Cowan's cells (SAC),
- iv) interleukin-21 (IL-21) and optionally interleukin-2 (IL-2),
- v) B-cell activation factor of the tumor necrosis factor family (BAFF),
- vi) interleukin-6 (IL-6),
- vii) interleukin-4 (IL-4), and
- viii) thymocyte cultivation supernatant.

In one embodiment of all corresponding aspects or embodiments the feeder mix comprises
up to about 2 ng/ml (murine) IL-1beta,
up to about 2 ng/ml (murine) TNFalpha,
up to about 50 ng/ml (murine) IL-2,
up to about 10 ng/ml (murine) IL-10, and
up to about 10 ng/ml (murine) IL-6,
or a fraction thereof.

In one embodiment of all corresponding aspects or embodiments the feeder mix comprises
up to about 2 ng/ml with $5.5\text{-}14*10^8$ IU/mg (murine) IL-1beta,
up to about 2 ng/ml with $2.3\text{-}2.9*10^8$ U/mg (murine) TNFalpha,
up to about 50 ng/ml with 6-7 (preferably 6.3)*$10^6$ IU/mg (murine) IL-2,
up to about 10 ng/ml with $6\text{-}7.5*10^5$ IU/mg (murine) IL-10, and
up to about 10 ng/ml with $9.2\text{-}16.1*10^8$ U/mg (murine) IL-6,
or a fraction thereof.

In one embodiment of all corresponding aspects or embodiments the fraction of the feeder mix is in the range of from 1.0- to 0.015-times of each of said concentrations of IL-1beta, TNFalpha, IL-2, IL-10, and IL-6.

In one embodiment of all corresponding aspects or embodiments the fraction of the feeder mix is selected from the group of fractions consisting of 0.75-, 0.5-, 0.32-, 0.25-, 0.1-, 0.066-, 0.032-, 0.015-, 0.01-, 0.0075-, and 0.0038-times of each of said concentrations of IL-1beta, TNFalpha, IL-2, IL-10, and IL-6.

In one embodiment of all corresponding aspects or embodiments the feeder mix further comprises about 0.01 ng/ml-1.0 ng/ml phorbol myristate acetate (PMA). In one embodiment the feeder mix further comprises about 0.01 ng/ml to 0.5 ng/ml phorbol myristate acetate.

In one embodiment of all corresponding aspects or embodiments the (co-)cultivating of one or more B-cells comprising the step of
co-cultivating one or more B-cells with EL-4 B5 cells in the presence of a feeder mix,
wherein the EL-4 B5 cells have been irradiated prior to the co-cultivation with a dose of 9.5 Gy or less,
wherein the number of EL-4 B5 cells (at the beginning of the co-cultivating) is less than $4\times10^4$ EL-4 B5 cells per B-cell,
wherein the feeder mix feeder mix comprises
up to about 2 ng/ml with $5.5\text{-}14*10^8$ IU/mg (murine) IL-1beta,
up to about 2 ng/ml with $2.3\text{-}2.9*10^8$ U/mg (murine) TNFalpha,
up to about 50 ng/ml with 6-7 (preferably 6.3)*$10^6$ IU/mg (murine) IL-2,
up to about 10 ng/ml with $6\text{-}7.5*10^5$ IU/mg (murine) IL-10, and
up to about 10 ng/ml with $9.2\text{-}16.1*10^8$ U/mg (murine) IL-6,
or a fraction of 0.75-, 0.5-, 0.32-, 0.25-, 0.1-, 0.066-, 0.032-, 0.015-, 0.01-, 0.0075-, or 0.0038-times of each of said concentrations of IL-1beta, TNFalpha, IL-2, IL-10, and IL-6,
and
wherein the feeder mix further comprises about 0.01 ng/ml-1.0 ng/ml phorbol myristate acetate.

In one embodiment of all corresponding aspects or embodiments the feeder mix comprises *Staphylococcus aureus* strain Cowan's cells (SAC) and thymocyte cultivation supernatant.

In one embodiment of all corresponding aspects or embodiments the method is for the co-cultivation of one B-cell. In one preferred embodiment the one B-cell is a single deposited B-cell.

In one embodiment of all corresponding aspects or embodiments the co-cultivating is for 5 to 10 days. In one preferred embodiment the co-cultivating is for about 7 days.

One aspect as reported herein is a method for producing an antibody comprising the co-cultivation method as reported herein.

All methods and uses as reported herein comprise the step of (individually) co-cultivating (each single deposited or a pool of) B-cell(s) with feeder cells in a co-cultivation medium, which has been supplemented with a feeder mix.

The result of the co-cultivation is a B-cell clone, i.e. a population of B-cells that are the progeny of a single B-cell.

In one embodiment of all corresponding aspects or embodiments the methods as reported herein further comprises prior to the co-cultivating step the following step:

depositing those B-cells of a population of B-cells that has been contacted with a labelled antibody according to the current invention and thereby fluorophores bound and/or not-bound to the B-cells in one or more individual containers.

In one embodiment of all corresponding aspects or embodiments the methods as reported herein further comprises prior to the co-cultivating step the following step:

depositing those B-cells of a population of B-cells that has been contacted with a labelled antibody according to the current invention and thereby fluorophores bound and/or not-bound to the B-cells as single B-cells.

In one embodiment of all corresponding aspects or embodiments the method as reported herein further comprises prior to the co-cultivating step the following step:

depositing those B-cells of a population of B-cells that has been contacted with an antibody according to the current invention and one to four additional antibodies each specifically binding to a different B-cell surface antigen, that are labelled with one to five fluorescence dyes as single cells, whereby each antibody is conjugated to a different fluorescent dye.

The labeling is by contacting the B-cell population (sequentially or simultaneously) with the fluorescently labeled antibodies. Thereby a labeled B-cell preparation is obtained. Each of the fluorescently labeled antibodies binds to a different B-cell surface marker/target.

The depositing is by introducing the labeled B-cell preparation into a flow cytometer and depositing those cells as single cells that have been labeled with one to three fluorescent labels. As it is possible to incubate the cells with more fluorescent dyes as those which are used for selecting the cells in the cell sorter the cells can be selected for the presence of specific surface markers and (optionally) simultaneously for the absence of other surface markers.

The labeling and single cell deposition is done in order to reduce the complexity of the B-cell population by depleting those B-cells that are not likely to produce an antibody having the intended characteristics. The labeled antibodies bind to a specific polypeptide displayed on the surface of B-cells and, thus, provide for a positive selection label. Likewise, it is also possible to select cells that are only labeled with a reduced number of fluorescent dyes compared to the number of labeled antibodies with which the B-cell had been incubated, such as e.g. cells having one fluorescent label out of two (i.e. incubation with two fluorescently labelled antibodies has been performed but only one thereof binds to the B-cells). Based on the binding/non-binding of the fluorescently labeled antibodies to the individual B-cells of the B-cell population it is possible to identify and separate target B-cells using a microfluidic sorting apparatus. Concomitantly with the selection also the amount of the label can be determined.

In one embodiment of all corresponding aspects or embodiments the method as reported herein further comprises the step of incubating the population of B-cells without feeder cells/in the absence of feeder cells in the co-cultivation medium prior to the single cell depositing/deposition. In one embodiment the incubating is at about 37° C. In one embodiment the incubating is for about 0.5 to about two hours. In one embodiment the incubating is for about one hour. In one preferred embodiment the incubating is at about 37° C. for about one hour.

In one embodiment of all corresponding aspects or embodiments the method as reported herein further comprises after the depositing step and before the co-cultivating step but after the addition of the EL-4 B5 feeder cells the step of centrifuging the single cell deposited B-cells. Without being bound by this theory it is assumed that thereby the physical contact between the feeder cells and the B-cell is increased. In one embodiment the centrifuging is for about 1 min. to about 30 min. In one embodiment the centrifuging is for about 5 min. In one embodiment the centrifuging is at about 100×g to about 1,000×g. In one embodiment the centrifuging is at about 300×g. In one preferred embodiment the centrifuging is for about 5 min. at about 300×g.

In one embodiment of all corresponding aspects or embodiments the method for selecting/obtaining a B-cell (clone) further comprises the following steps:

a) labeling the B-cells of a population of B-cells with (one to five) fluorescent dyes (optionally by incubating the B-cell population with two to five fluorescently labeled antibodies specifically binding to two to five different pre-determined B-cell surface markers), whereof one is (conjugated to) the antibody according to the current invention, b) optionally incubating the labelled cells in co-cultivation medium, c) depositing those B-cells of the population of B-cells that have been labeled with at least one (one to five) fluorescent dye(s) (and optionally not labeled with the other fluorescent dye(s)) as single cells on EL-4 B5 feeder cells that have been irradiated with a dose of 9.5 Gy or less, d) optionally centrifuging the single deposited B-cells/feeder cell mixture, e) (individually) co-cultivating each single deposited B-cell with feeder the cells in a co-cultivation medium, which has been supplemented with a feeder mix, f) selecting a B-cell clone proliferating and secreting an antibody in step e).

In one embodiment of all corresponding aspects or embodiments the method for producing an antibody specifically binding to a target further comprises the following steps a) labeling the B-cells of a population of B-cells with (one to five) fluorescent dyes (optionally by incubating the B-cell population with two to five fluorescently labeled antibodies specifically binding to two to five different pre-determined B-cell surface markers), whereof one is (conjugated to) the antibody according to the current invention, b) optionally incubating the cells in co-cultivation medium, c) depositing those B-cells of the population of B-cells that have been labeled with at least one (one to five) fluorescent dye(s) (and optionally not labeled with the other fluorescent dye(s)) as single cells EL-4 B5 feeder cells that have been irradiated with a dose of 9.5 Gy or less,
d) optionally centrifuging the single deposited B-cell/feeder cell mixture,
e) (individually) co-cultivating each single deposited B-cell with the feeder cells in a co-cultivation medium, which has been supplemented with a feeder mix,
f) selecting a B-cell clone of step e) secreting an antibody,
g) i) obtaining one or more nucleic acids encoding the secreted antibody's variable domains from the B-cell clone selected in step g),
   ii) if the B-cell clone is not a human B-cell clone humanizing the variable domains and providing the respective encoding nucleic acids, and
   iii) introducing the one or more nucleic acids in one or more expression vectors in frame with nucleic acid sequences encoding constant regions,
h) cultivating a cell (optionally selected from CHO and BHK cells), which has been transfected with the one or more expression vectors of step g), and recovering the antibody from the cell or the cultivation supernatant and thereby producing the antibody.

In one embodiment of all corresponding aspects or embodiments the method for producing an antibody further comprises the following steps
a) labeling the B-cells of a population of B-cells with (one to five) fluorescent dyes (optionally by incubating the B-cell population with two to five fluorescently labeled antibodies specifically binding to two to five different pre-determined B-cell surface markers), whereof one is (conjugated to) the antibody according to the current invention,
b) optionally incubating the cells in co-cultivation medium,
c) depositing those B-cells of a population of B-cells that have been labeled with at least one (one to five) fluorescent dyes (and optionally not labeled with the other fluorescent dye(s)) as single cells on EL-4 B5 feeder cells that have been irradiated with a dose of 9.5 Gy or less,
d) optionally centrifuging the single deposited B-cell/feeder cell mixture,
e) (individually) co-cultivating each single deposited B-cell with the feeder cells in a co-cultivation medium, which has been supplemented with a feeder mix,
f) determining the binding specificity of the antibodies secreted in the cultivation medium of the co-cultivated B-cells for each supernatant individually,
g) selecting a B-cell clone of step 0 based on the binding properties of the secreted antibody,
h) obtaining one or more nucleic acids encoding the secreted antibody's variable domains from the B-cell clone selected in step g) by a reverse transcriptase PCR and nucleotide sequencing, (and thereby obtaining a monoclonal antibody variable light and heavy chain domain encoding nucleic acid,)
i) if the B-cell is a non-human B-cell humanizing the variable light and heavy chain domain and providing a nucleic acid encoding the humanized variable domains,
j) introducing the monoclonal antibody variable light and heavy chain variable domain encoding nucleic acid in one or more expression vectors (in frame with nucleic acids encoding antibody constant domains) for the expression of an (human or humanized) antibody,
k) introducing the expression vector(s) into a mammalian cell (optionally selected from CHO and BHK cells),
l) cultivating the cell and recovering the antibody from the cell or the cell culture supernatant and thereby producing the antibody.

In one embodiment of all corresponding aspects or embodiments the obtaining one or more nucleic acids encoding the secreted antibody's variable domains from the B-cell clone further comprises the following steps:
   extracting total RNA from the antibody-producing B-cell clone,
   performing a single stranded cDNA synthesis/reverse transcription of the extracted polyA$^+$ mRNA,
   performing a PCR with a set of species specific primer,
   optionally removal of the PCR primer/purification of the PCR product,
   optionally sequencing of the PCR product.

In one embodiment of all corresponding aspects or embodiments the introducing the monoclonal antibody variable light and/or heavy chain variable domain encoding nucleic acid in an expression vector for the expression of an (human or humanized) antibody further comprises the following steps:
   T4 polymerase incubation of the variable light and heavy chain variable domain,
   linearization and amplification of the expression vector,
   T4 polymerase incubation of the amplified expression vector,
   sequence and ligation independent cloning of the variable domain encoding nucleic acid into the amplified expression vector, and
   preparation of the vector(s) from pool of vector transformed E. coli cells.

In one embodiment of all corresponding aspects or embodiments the method further comprises immediately prior to the labeling step the following step:
   incubating the population of B-cells with (target) antigen, which is soluble, fluorescent-labelled or immobilized on a solid surface, and recovering (only) B-cells bound to the (immobilized) antigen.

In one embodiment of all corresponding aspects or embodiments the population of B-cells is obtained from the blood of a rabbit at least 4 days after the immunization. In one embodiment the population of B-cells is obtained from the blood of a rabbit of from 4 days up to at most 13 days after immunization.

In one embodiment of all corresponding aspects or embodiments the population of B-cells is obtained from blood by density gradient centrifugation.

In one embodiment of all corresponding aspects or embodiments the B-cells are mature B-cells.

In one embodiment of all corresponding aspects or embodiments the single cells are deposited (individually) into the wells of a multi-well plate.

In one embodiment of all corresponding aspects or embodiments the feeder mix is natural thymocyte cultivation supernatant (TSN) or a defined and/or synthetic feeder mix. In one embodiment the thymocyte cultivation supernatant is obtained from thymocytes of the thymus gland of a young animal.

In one embodiment of all corresponding aspects or embodiments the feeder mix is a defined and/or synthetic feeder mix. In one embodiment the defined and/or synthetic feeder mix comprises
   i) interleukin-1 beta and tumor necrosis factor alpha, and/or ii) interleukin-2 (IL-2) and/or interleukin-10 (IL-10), and/or
iii) *Staphylococcus aureus* strain Cowan's cells (SAC), and/or
iv) interleukin-21 (IL-21) and optionally interleukin-2 (IL-2), and/or
v) B-cell activation factor of the tumor necrosis factor family (BAFF), and/or
vi) interleukin-6 (IL-6), and/or
vii) interleukin-4 (IL-4).

In one embodiment of all corresponding aspects or embodiments the feeder mix comprises IL-1β and TNF-α and one or more selected from IL-10, IL-21, SAC, BAFF, IL-2, IL-4, and IL-6.

In one embodiment of all corresponding aspects or embodiments the feeder mix comprises IL-1β, TNF-α, IL-10, SAC and IL-2.

In one embodiment of all corresponding aspects or embodiments the B-cell population is a rabbit B-cell population and feeder mix is a thymocyte cultivation supernatant.

In one embodiment of all corresponding aspects or embodiments the B-cell population is a rabbit B-cell population and the feeder mix is consisting of IL-1β, TNF-α, and any two of IL-2, IL-6 and IL-10.

In one embodiment of all corresponding aspects or embodiments the B-cell population is a rabbit B-cell population and the feeder mix is consisting of IL-1β, TNF-α, IL-6 and IL-10.

In one embodiment of all corresponding aspects or embodiments the B-cell population is a rabbit B-cell population and the feeder mix comprises IL-1β, TNF-α, IL-10, SAC and IL-2 or IL-6.

In one embodiment of all corresponding aspects or embodiments the B-cell population is a rabbit B-cell population and the feeder mix comprises IL-1β, TNF-α, IL-21 and at least one of IL-2, IL-10 and IL-6.

In one embodiment of all corresponding aspects or embodiments the antibody is a monoclonal antibody.

In one embodiment of all corresponding aspects or embodiments the labeling is of B-cell surface IgG.

In one preferred embodiment of all corresponding aspects or embodiments the incubation is with a fluorescently labelled antibody according to the current invention, a fluorescently labeled anti-IgG antibody and a fluorescently labeled anti-IgM antibody (the labeling is of cell surface IgG and cell surface IgM) and the selection is of cells positive for cell surface CD19, cell surface IgG and negative for cell surface IgM (results in single cell deposition of CD19$^+$IgG$^+$IgM$^-$-B-cells).

In one embodiment of all corresponding aspects or embodiments the incubation is with a fluorescently labelled antibody according to the current invention, a fluorescently labeled anti-IgG antibody and a fluorescently labeled anti-light chain antibody (the labeling is of cell surface IgG and cell surface antibody light chain) and the selection is of cells positive for cell surface CD19, cell surface IgG and cell surface antibody light chain (results in single cell deposition of IgG+LC+-B-cells).

In one embodiment of all corresponding aspects or embodiments the incubation is in addition with a fluorescently labeled anti-light chain antibody (the labeling is of cell surface antibody light chain in addition to the other two labels) and the selection is of cells positive for cell surface antibody light chain (results in single cell deposition of LC+-B-cells).

In one preferred embodiment of all corresponding aspects or embodiments the incubation is with a fluorescently labelled antibody according to the current invention, a fluorescently labeled anti-IgG antibody and a fluorescently labeled anti-IgM antibody (the labeling is of cell surface CD19, cell surface IgG and cell surface IgM) and the selection is of cells positive for cell surface CD19 and IgG and negative for cell surface IgM (results in single cell deposition of CD19$^+$IgG$^+$IgM$^-$-B-cells), whereby the population of B-cells has been incubated with (target) antigen, which is immobilized on a solid surface, and (only) B-cells bound to the immobilized antigen have been recovered and subjected to the incubation with the fluorescently labeled antibodies.

In one embodiment of all corresponding aspects or embodiments the co-cultivating is in a co-cultivation medium comprising RPMI 1640 medium supplemented with 10% (v/v) FCS, 1% (w/v) of a 200 mM glutamine solution that comprises penicillin and streptomycin, 2% (v/v) of a 100 mM sodium pyruvate solution, and 1% (v/v) of a 1 M 2-(4-(2-hydroxyethyl)-1-piperazine)-ethane sulfonic acid (HEPES) buffer. In one embodiment the co-cultivation medium further comprises 0.05 mM beta-mercaptoethanol.

In a further method the antibody according to the current invention or a rabbit CD19 binding fragment thereof is immobilized on a solid phase and used to capture rabbit CD19-positive B-cells. The solid surface may by any surface including the wells of a multi-well plate or beads, especially magnetic beads. These immobilized antibodies according to the invention can be used in a similar manner as labelled antibody according to the invention, i.e. to selectively bind rabbit CD19 positive B-cells. A person skilled in the art knows how to replace the FACS-based steps in the methods described above with a bead based approach.

For example, one aspect of the current invention is a method for selecting B-cells comprising the following steps:
a) obtaining B-cells from the blood of a rabbit,
b) incubating the B-cells with an antibody according to the current invention immobilized to a bead,
c) washing the beads to remove non-bound B-cells,
d) optionally recovering the B-cells from the beads and thereby selecting one or more B-cells to which the antibody according to the invention is bound.

In one embodiment of all corresponding aspects or embodiments the bead is a magnetic bead. In a further embodiment the method comprises after step b) and before step c) the step of bc) binding the beads to a magnet.

In one embodiment of all corresponding aspects or embodiments the method further comprises one or more of the following steps:
d) optionally incubating the B-cells at 37° C. for one hour in co-cultivation medium,
e) depositing one or more B-cells or beads in an individual container, f) co-cultivating the deposited cells with a feeder cell in a co-cultivation medium,
g) selecting a B-cell proliferating in step 0 and thereby selecting a B-cell.

One aspect as reported herein is a method for selecting a B-cell comprising the following steps:
a) co-cultivating each of the B-cells of an enriched population of B-cells, which has been obtained from an original population of B-cell by binding to the antibody according to the current invention, which itself was bound to a solid surface, with murine EL-4 B5 cells as feeder cells, and
b) selecting a B-cell clone proliferating and secreting antibody in step a).

One aspect as reported herein is a method for producing an antibody binding to a target antigen comprising the following steps
- a) co-cultivating one or more B-cells of an enriched population of B-cells, which has been obtained from an original population of B-cell by binding to the antibody according to the current invention, which itself was bound to a solid surface, optionally in the presence of murine EL-4 B5 cells as feeder cells and IL-1β, TNFα, IL-10, and one or more selected from IL-21, SAC, BAFF, IL-2, IL-4, and IL-6 as feeder mix,
- b) selecting a B-cell clone producing an antibody specifically binding to the target antigen,
- b1) determining the nucleic acid sequence encoding the variable light chain domain and the variable heavy chain domain of the antibody by a reverse transcriptase PCR,
- b2) transfecting a cell with a nucleic acid comprising the nucleic acid sequence encoding the antibody variable light chain domain and the variable heavy chain domain,
- c) cultivating the cell, which contains the nucleic acid that encodes the antibody produced by the B-cell clone selected in step b) or a humanized variant thereof, and recovering the antibody from the cell or the cultivation supernatant and thereby producing the antibody.

One aspect as reported herein is a method for co-cultivating one or more rabbit B-cells comprising the steps of
- incubating a multitude of rabbit B-cells/labelling individual B-cells of a multitude of rabbit B-cells with an antibody according to the current invention that is bound to a solid surface,
- selecting/depositing one or more rabbit B-cells that have the antibody according to the invention bound to their surface either as individual B-cells (single deposited B-cell) or as a pool of B-cells, and
- co-cultivating the single deposited rabbit B-cells or the pool of rabbit B-cells with feeder cells,
- optionally incubating after the co-cultivation the obtained cell mixture with an antibody according to the current invention that is conjugated to a detectable label and selecting/depositing/counting rabbit B-cells that have the antibody according to the invention bound to their surface/that have been labelled.

B. Recombinant Methods and Compositions

Antibodies may be produced using recombinant methods and compositions, e.g., as described in U.S. Pat. No. 4,816,567. In one embodiment, isolated nucleic acid encoding an anti-human CD19 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making an anti-rabbit CD19 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-rabbit CD19 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.)

After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Methods and Compositions for Diagnostics and Detection

In certain embodiments, any of the anti-rabbit CD19 antibodies provided herein is useful for detecting the presence of rabbit CD19 presenting cells in a biological sample. The term "detecting" as used herein encompasses quantitative or qualitative detection. In certain embodiments, a biological sample comprises a cell or tissue, such as e.g. blood, blood serum, or blood plasma.

In one embodiment, an anti-rabbit CD19 antibody for use in a method of diagnosis or detection is provided. These aspects have been outlined above.

In certain embodiments, labeled anti-rabbit CD19 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

III. DESCRIPTION OF THE SEQUENCE LISTING

SEQ ID NO: 01 rabbit CD19 amino acid sequence without signal peptide
SEQ ID NO: 02 rabbit CD19 amino acid sequence with signal peptide
SEQ ID NO: 03 rabbit CD19 cDNA
SEQ ID NO: 04 hamster CD19 amino acid sequence
SEQ ID NO: 05 mouse CD19 amino acid sequence
SEQ ID NO: 06 rat CD19 amino acid sequence
SEQ ID NO: 07 squirrel CD19 amino acid sequence
SEQ ID NO: 08 marmoset CD19 amino acid sequence
SEQ ID NO: 09 rhesus monkey CD19 amino acid sequence
SEQ ID NO: 10 human CD19 amino acid sequence
SEQ ID NO: 11 cat CD19 amino acid sequence
SEQ ID NO: 12 naked mole rat CD19 amino acid sequence
SEQ ID NO: 13 guinea pig CD19 amino acid sequence
SEQ ID NO: 14 pig CD19 amino acid sequence
SEQ ID NO: 15 dog CD19 amino acid sequence
SEQ ID NO: 16 gap consensus amino acid sequence
SEQ ID NO: 17 primer
SEQ ID NO: 18 primer
SEQ ID NO: 19 primer
SEQ ID NO: 20 primer
SEQ ID NO: 21 primer
SEQ ID NO: 22 primer
SEQ ID NO: 23 primer
SEQ ID NO: 24 antibody 1H2 light chain amino acid sequence
SEQ ID NO: 25 antibody 1H2 light chain leader peptide amino acid sequence
SEQ ID NO: 26 antibody 1H2 light chain variable domain amino acid sequence
SEQ ID NO: 27 antibody 1H2 light chain constant region amino acid sequence
SEQ ID NO: 28 antibody 1H2 heavy chain amino acid sequence
SEQ ID NO: 29 antibody 1H2 heavy chain leader peptide amino acid sequence
SEQ ID NO: 30 antibody 1H2 heavy chain variable domain amino acid sequence
SEQ ID NO: 31 antibody 1H2 heavy chain constant region amino acid sequence
SEQ ID NO: 32 antibody 1H2 heavy chain HVR-1 variant 1
SEQ ID NO: 33 antibody 1H2 heavy chain HVR-1 variant 2
SEQ ID NO: 34 antibody 1H2 heavy chain HVR-1 variant 3
SEQ ID NO: 35 antibody 1H2 heavy chain HVR-2 variant 1
SEQ ID NO: 36 antibody 1H2 heavy chain HVR-2 variant 2
SEQ ID NO: 37 antibody 1H2 heavy chain HVR-3
SEQ ID NO: 38 antibody 1H2 light chain HVR-1
SEQ ID NO: 39 antibody 1H2 light chain HVR-2
SEQ ID NO: 40 antibody 1H2 light chain HVR-3
SEQ ID NO: 41 human kappa light chain constant region amino acid sequence
SEQ ID NO: 42 human lambda light chain constant region amino acid sequence
SEQ ID NO: 43 human IgG1 heavy chain constant region amino acid sequence; caucasian allotype
SEQ ID NO: 44 human IgG1 heavy chain constant region amino acid sequence; afroamerican allotype
SEQ ID NO: 45 human IgG1 heavy chain constant region amino acid sequence; LALA variant
SEQ ID NO: 46 human IgG1 heavy chain constant region amino acid sequence; LALAPG variant
SEQ ID NO: 47 human IgG4 heavy chain constant region amino acid sequence
SEQ ID NO: 48 human IgG4 heavy chain constant region amino acid sequence; SPLE variant
SEQ ID NO: 49 human IgG4 heavy chain constant region amino acid sequence; SPLEPG variant
SEQ ID NO: 50 mouse kappa light chain constant region amino acid sequence
SEQ ID NO: 51 human lambda light chain constant region amino acid sequence SEQ ID NO: 52 GPI anchor amino acid sequence SEQ ID NO: 53 3' UTR primer SEQ ID NO: 54 5' UTR primer

IV. DESCRIPTION OF THE FIGURES

Figure 1B:
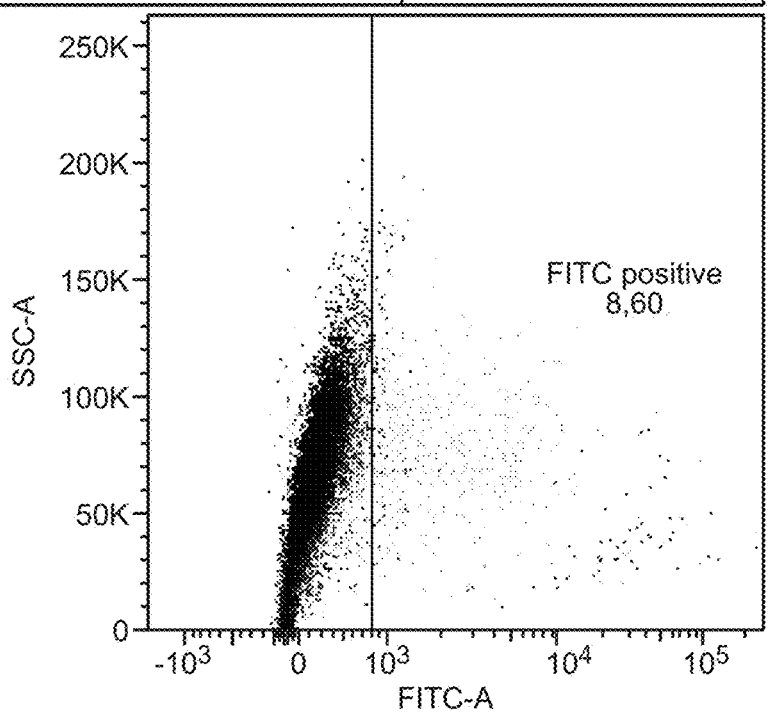

FIGS. 1A-1C FACS analysis of recombinant murine cells transfected with expression plasmid for rabbit CD19 fused to a FLAG-tag. Rabbit CD19 expression was indirectly confirmed by cell surface staining using an FITC labeled anti-FLAG-tag antibody.

FIG. 1A: NIH/3T3, normal transfection using LipofectAmine, 24 h after transfection;

FIG. 1B: C2C12, normal transfection using LipofectAmine, 24 h after transfection;

FIG. 1C: NIH/3T3, reverse transfection using LipofectAmine, 48 h after transfection.

FIGS. 2A-2B FACS analysis of rabbit PBMC for identification of rabbit CD19-binding hybridoma supernatants. Rabbit PBMCs were double stained with a FITC-labeled anti-rabbit IgM antibody and with hybridoma supernatants. The unlabeled mouse antibodies of the individual hybridoma supernatants were developed by PE-labeled anti-mouse IgG antibody.

FIG. 2A: positive hybridoma supernatant binding to rabbit CD19 on rbIgM-positive B cells;

FIG. 2B: exemplarily, a negative hybridoma supernatant showing no binding to rabbit IgM-positive B-cells.

FIGS. 3A-3D Use of rabbit CD19 as a B-cell marker using the purified and Alexa 647-labeled anti-rabbit CD19 antibody. The comparison of the FACS plots of the gates used during single B-cell sorting with the plot generated by the index sort approach revealed that the antigen specific and IgG-secreting B-cells were highly rabbit CD19-positive.

Figure 3A:
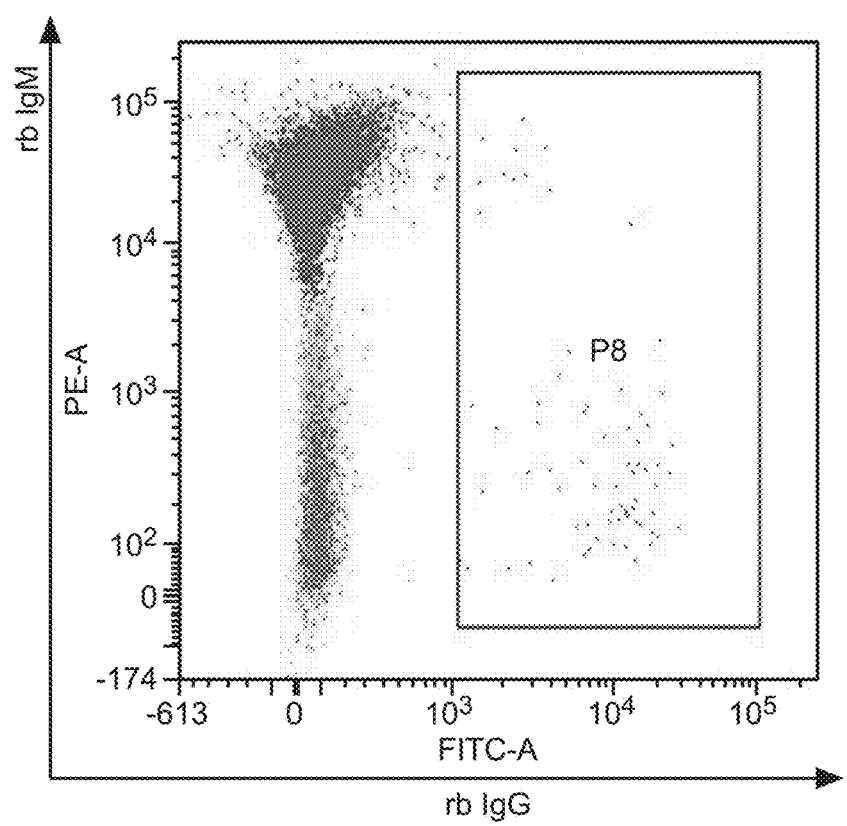
Figure 3B:
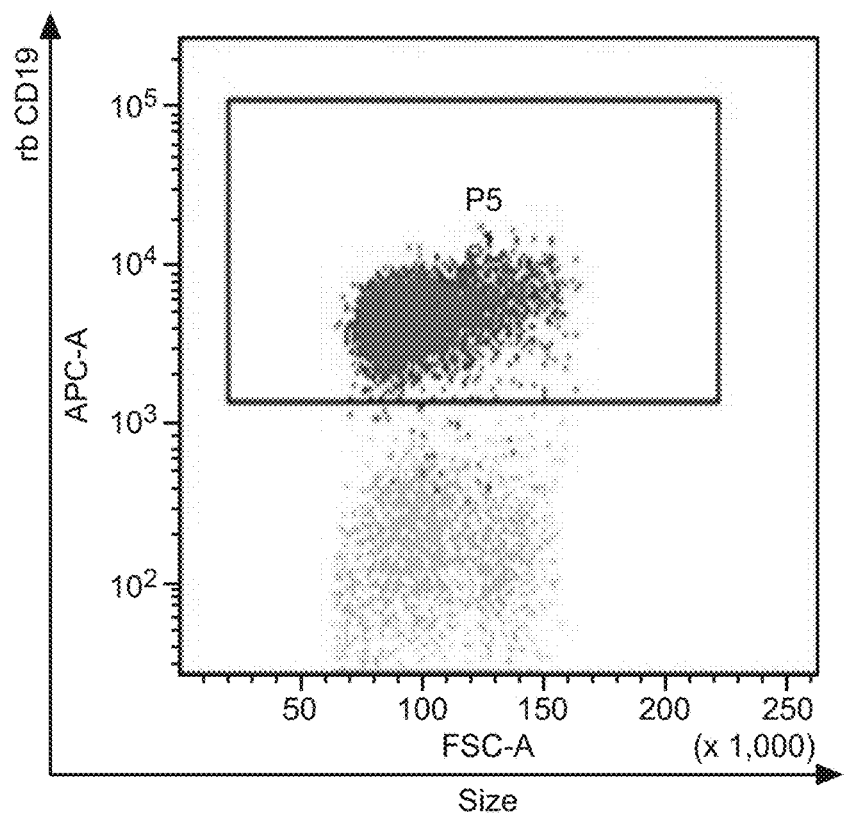
Figure 3C:
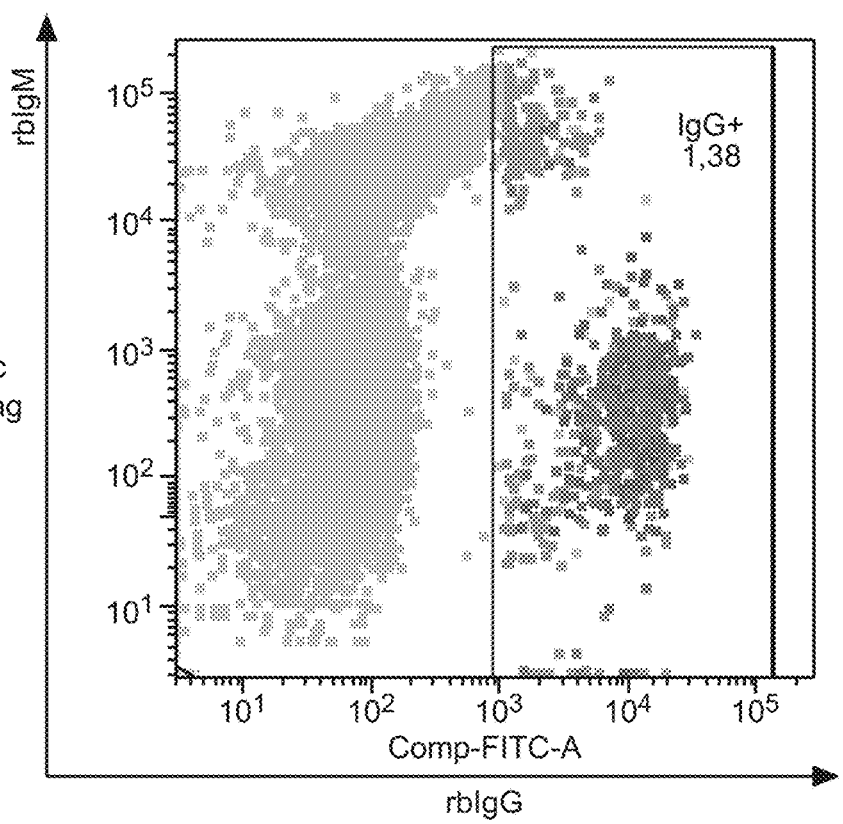
Figure 3D:
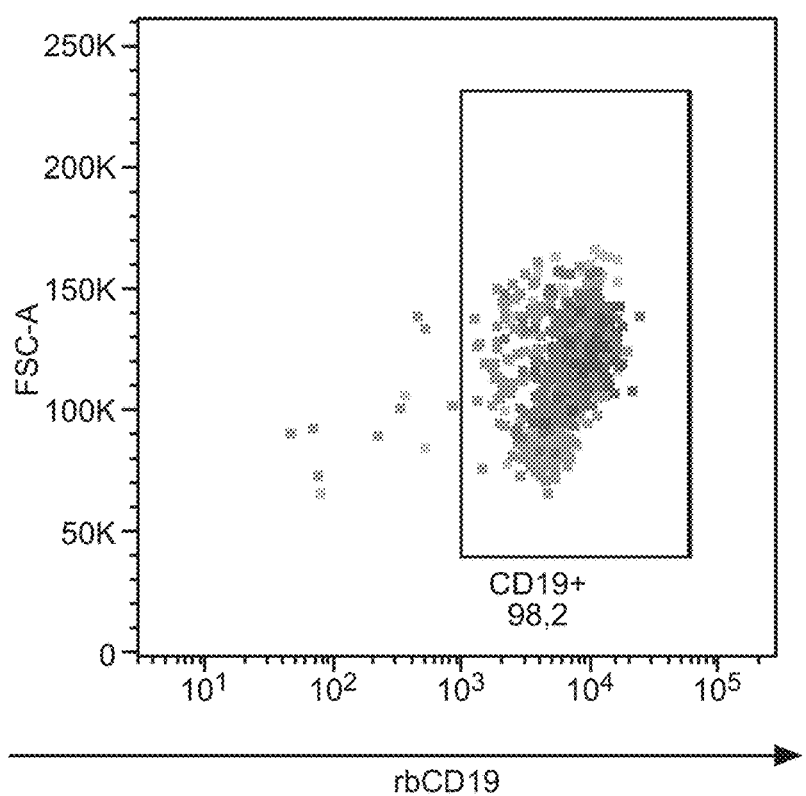

FIG. 3A: FACS plot of the rabbit IgG-FITC labeled B-cells (gate P8) that was used for single cell sorting. Rabbit IgM-PE labeling of rabbit B-cells was used as a counter staining;

FIG. 3B: use of anti-rabbit CD19 antibody based labeling (gate P5) for characterization of the sorted B cells;

FIG. 3C: FACS plot generated by the index sort approach including data of the rabbit IgG- and antigen-specific ELISA depicting the rabbit IgG gate;

FIG. 3D: FACS plot generated by the index sort approach including data of the rabbit IgG- and antigen-specific ELISA depicting the rabbit CD19 gate.

Figure 4A:
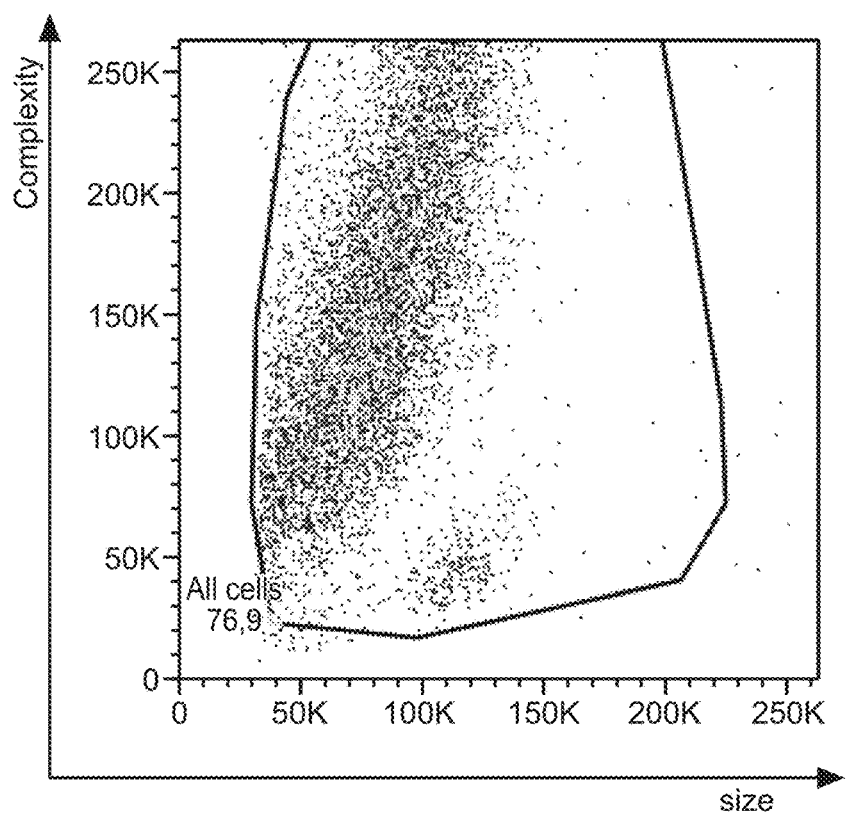
Figure 4B:
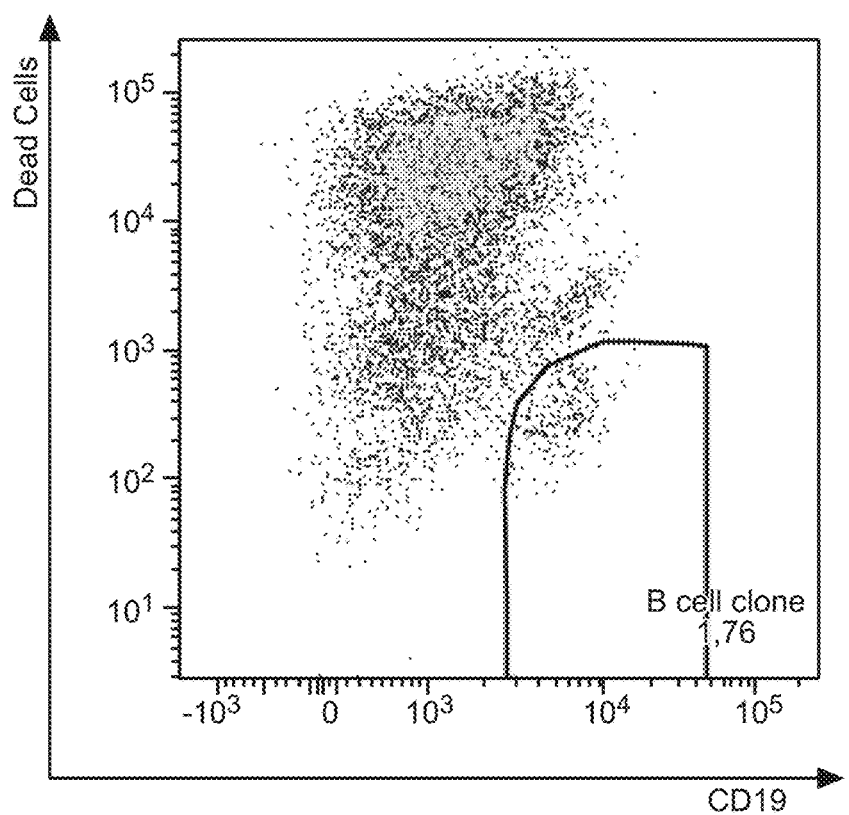
Figure 4C:
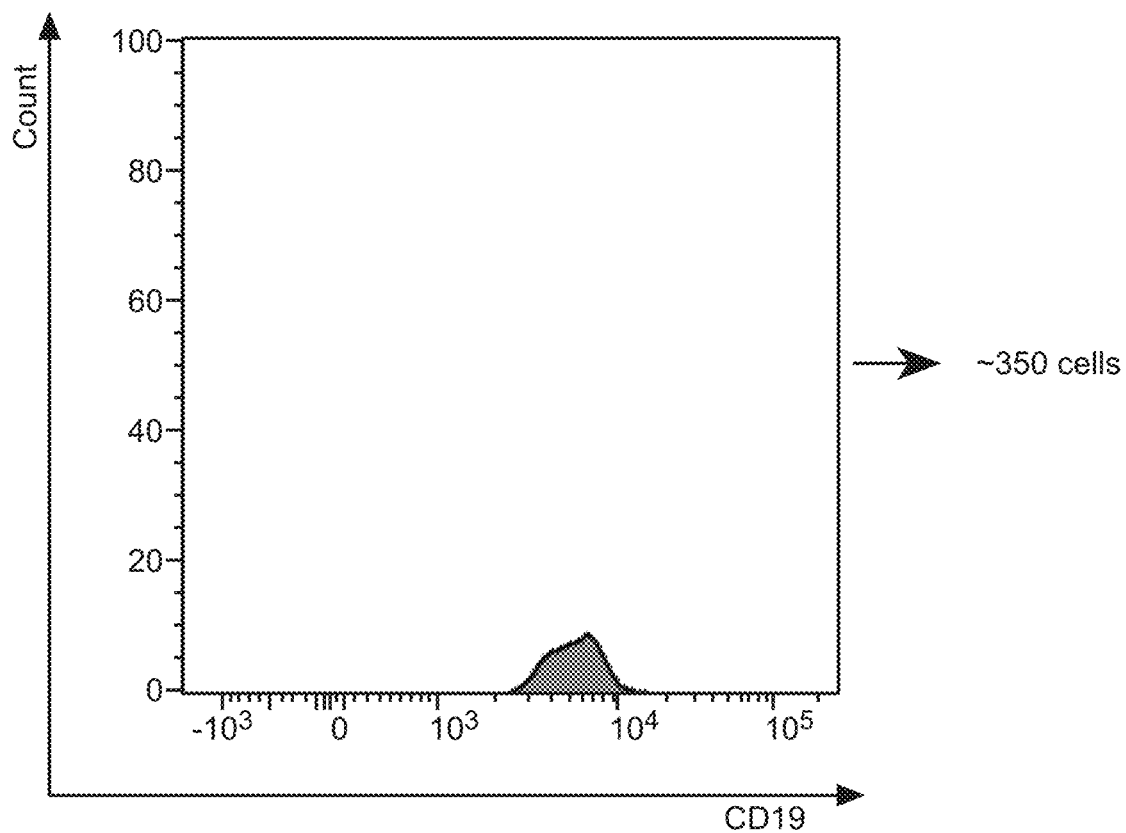

FIGS. 4A-4C FACS analysis of B-cells and feeder cells after 7 days of B-cell culture.

FIG. 4A: FACS plot showing all cells distributed via cell size (FSC; forward scatter) and cell complexity (SSC; side scatter);

FIG. 4B: FACS plot showing all cells distributed via rabbit CD19 staining (Alexa 647) and dead cells (propidium iodide);

FIG. 4C: exact count of B-cells of a well containing very few B-cells.

Figure 5A:
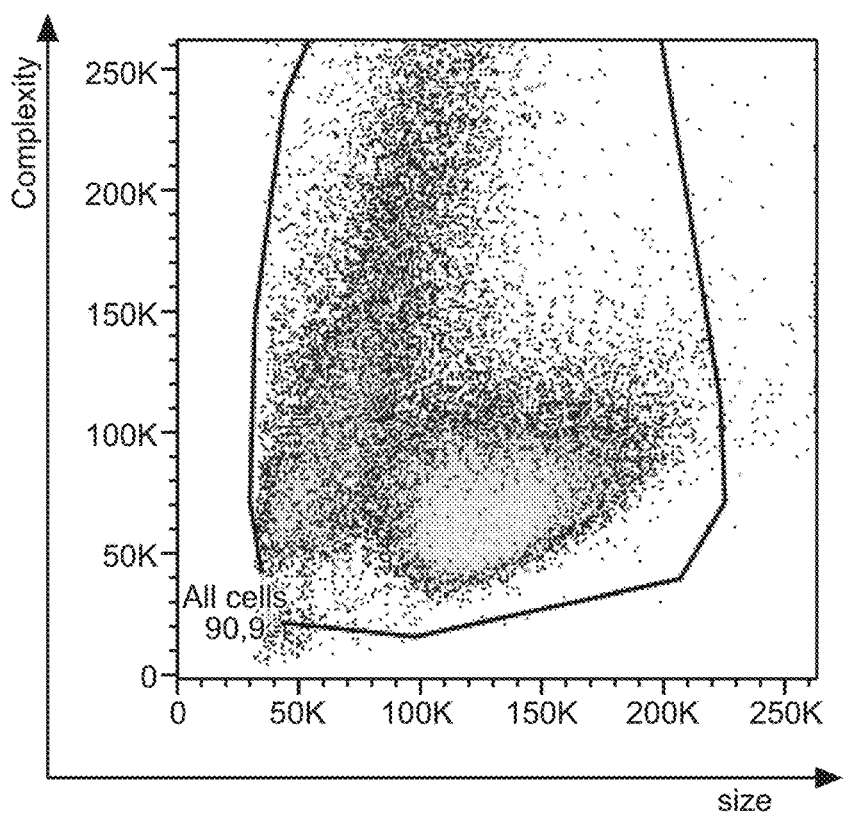
Figure 5B:
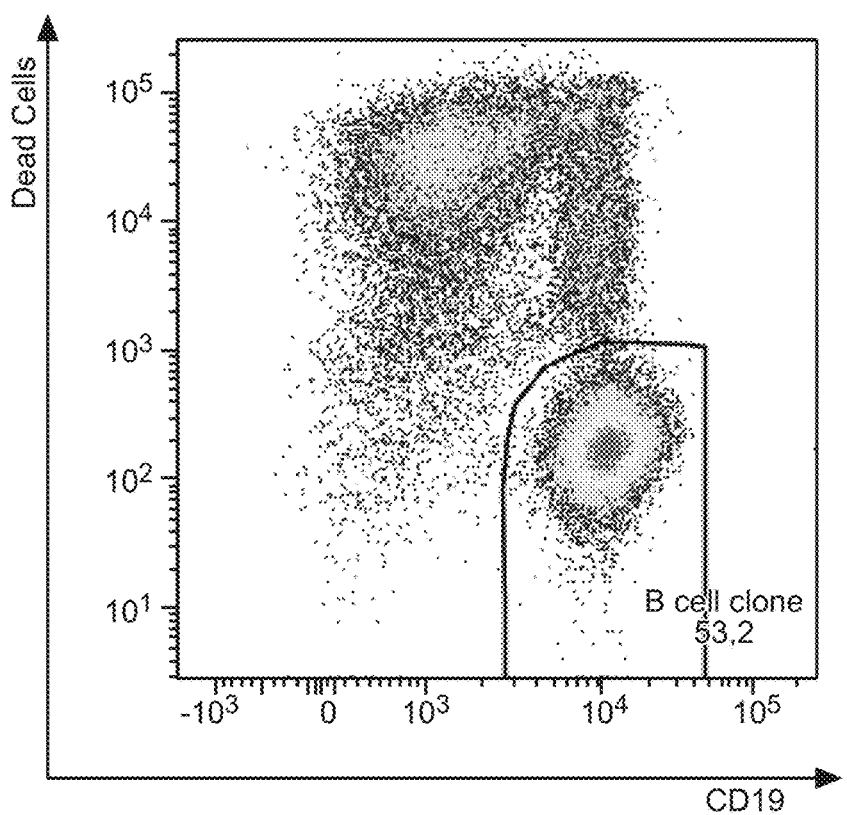
Figure 5C:
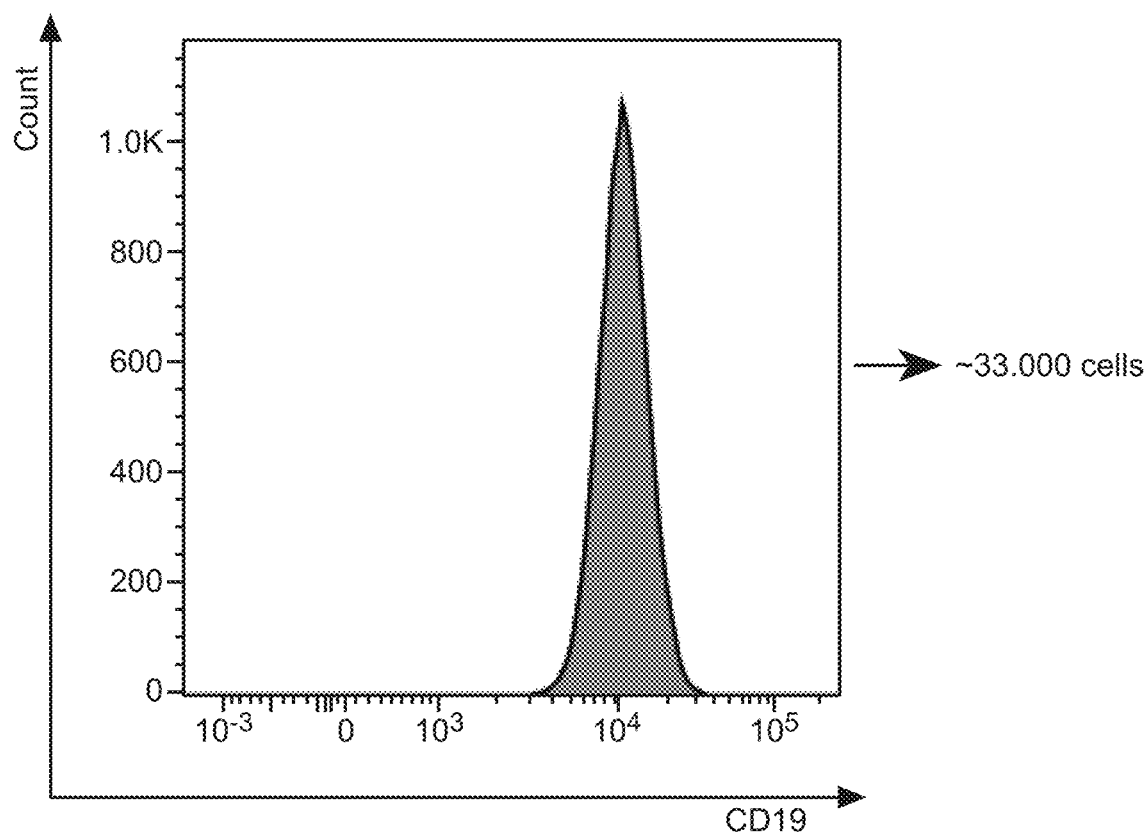

FIGS. 5A-5C FACS analysis of B-cells and feeder cells after 7 days of B-cell culture.

FIG. 5A: FACS plot showing all cells distributed via cell size (FSC) and cell complexity (SSC);

FIG. 5B: FACS plot showing all cells distributed via rabbit CD19 staining (Alexa 647) and dead cells (propidium iodide);

FIG. 5C: exact count of B-cells of a well containing a high number of B-cells.

FIGS. 6A-6B FIG. 6A: FACS Plot of peripheral blood lymphocytes (PBLs) from rabbit showing the cell size (FSC) and the cell complexity (SSC).

FIG. 6B: FACS Plot of PBLs from rabbit showing the cell size (FSC) and the rabbit IgG-stained cell population (=gate P5) in the FITC channel.

Figure 7A:
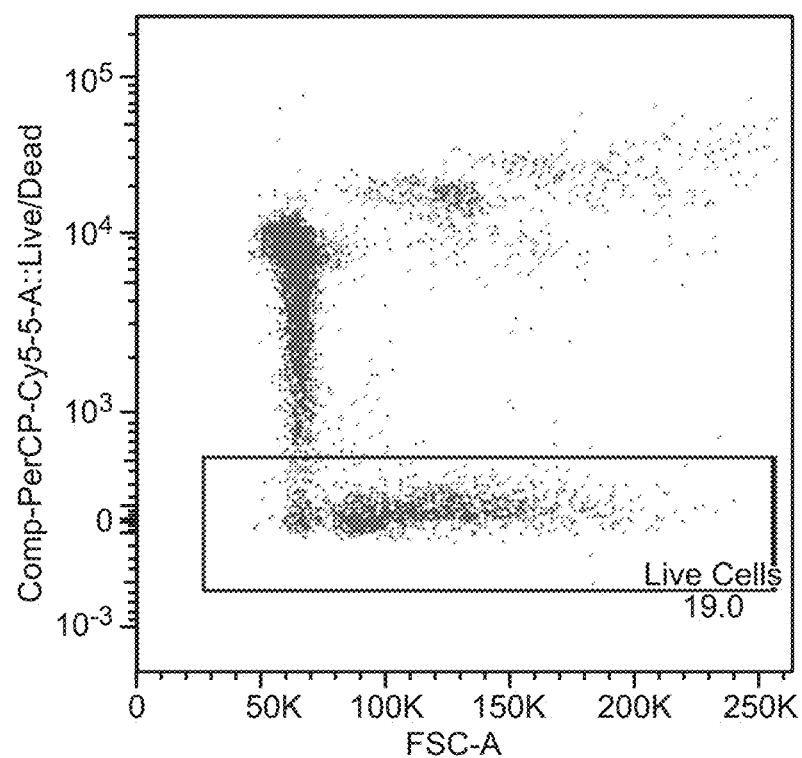
Figure 7B:
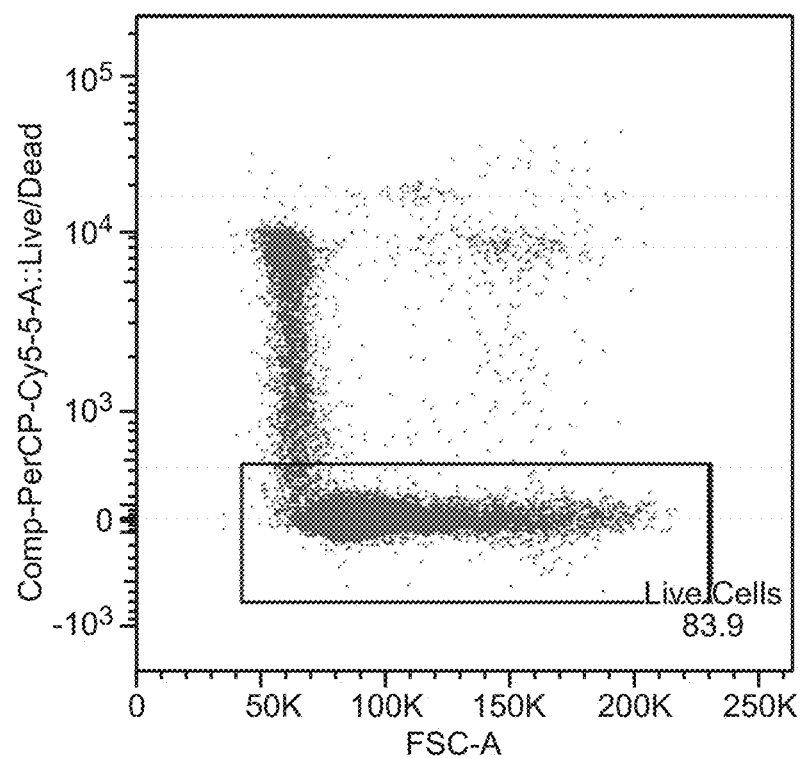

FIGS. 7A-7B FIG. 7A: FACS plot showing the viability of the B-cells after antigen enrichment with magnetic beads.

FIG. 7B: FACS plot showing the viability of the B-cells after CD19+ B-cell enrichment.

V. EXAMPLES

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1

Immunization and Generation of Mouse Anti-Rabbit CD19 Antibodies (Hybridomas)

NMRI mice obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number AZ. 55.2-1-54-2531-83-13) and performed according to the German Animal Welfare Act and the Directive 2010/63 of the European Parliament and Council.

NMRI mice (n=5), 6-8 week old, received plasmid DNA-based immunizations over a course of three months. The plasmid DNA encoding for rabbit CD19 as a single chain molecule was used for this purpose. Before harvest of spleens for hybridoma fusion a boost with NIH/3T3 cells (ATCC CRL-1658) transiently transfected with the same vector for expression of rabbit CD19 was given.

For the first immunization, animals were isoflurane-anesthetized and intradermally (i.d.) immunized with 100 µg plasmid DNA in sterile $H_2O$ applied to one spot at the shaved back, proximal to the animal's tail. After i.d. application, the spot was electroporated using following parameters on an ECM 830 electroporation system (BTX Harvard Apparatus): two times 1000V/cm for 0.1 ms each, separated by an interval of 125 ms, followed by four times 287.5V/cm for 10 ms, separated also by intervals of 125 ms. Booster immunizations were given on days 14, 28, 49, 63 and 77 in a similar fashion. Six weeks after the final immunization, 0.9×10E6 NIH/3T3 cells transiently transfected for expression of rabbit CD19 and dissolved in sterile PBS were injected intravenously (i.v.) and intraperitoneally (i.p.) each into mice. 72h later, spleens were aseptically harvested and prepared for hybridoma generation.

Fusions of spleen cells from immunized mice were performed according to a standard protocol: Myeloma cell line P3X63-Ag8653 was cultivated in RPMI 1640 medium containing 5% (v/v) FCS and 8-Azaguanin to a cell density of $3\times10^5$ cells/mL. Cells were then harvested (1,000 rpm, 10 min, 37° C.) and washed in 50 mL RPMI (37° C.). After a second centrifugation step under the same conditions, cells were resuspended in 50 mL RPMI (37° C.) and stored on ice afterwards. A sterile extracted spleen from an immunized mouse was used to decollate single cells through a cell strainer (70 µm). The single cell culture was transferred into a 15 mL tube and incubated on ice for 10 min. After incubation, the cell suspension supernatant was transferred into a 50 mL tube, harvested (250×g, 10 min, 4° C.) and resuspended in 15 mL RPMI medium.

After detection of cell densities, spleen cells and myeloma cells were mixed at a ratio of 5:1 and centrifuged (250×g, 10 min, 37° C.). 1 mL polyethylene glycol (PEG) per $10^8$ spleen cells was added under gentle shaking and the sample was incubated for at least 30 min at 37° C. and an atmosphere of 6% $CO_2$. After incubation, cells were harvested for 10 min at 250×g (37° C.) and resuspended in 20 mL of RPMI medium. The whole fusion sample was finally transferred into microtitre plates (MTPs, 200 µl/well), incubated (37° C., 6% $CO_2$) and used for further analysis.

Example 2

Hybridoma Screening and Cell Biological Functional Evaluation of Anti-CD19 Antibody
High Throughput FACS Analysis for Screening Antibodies Against Rabbit CD19

The hybridoma supernatants were characterized by a mouse IgG ELISA. Primary screening of IgG containing culture supernatants was performed by ELISA using a standard protocol: Streptavidine coated 384-well-MTPs were incubated with a biotinylated polyclonal anti-murine Fcg-region antibody (pAK<MFcg>S-IgH-(IS)-Bi (XOSu)). 50 µl/well of supernatants (diluted 1:600) were applied and incubated for 60 min. at room temperature. Afterwards, samples were washed three times with 0.9% (w/v) NaCl, 0.05% (v/v) Tween 20, 0.2% (v/v) BronidoxL. For the detection of IgG, samples were incubated with a peroxidase-conjugated AffiniPure goat-anti-mouse F(ab')2 fragment (1:15,000 dilution, 50 µl/well) and incubated for 60 min. at room temperature. After washing as described above, ABTS solution (1 mg/mL, 50 µl/well) was added and incubated for further 20 min. Read out was performed at a wave lengths of 405/492 nm with an X Read Plus Reader (Tecan). Only IgG-positive hybridoma supernatants were subjected to the antigen-specific high throughput FACS analysis.

FACS analysis was applied for screening of hybridomas and to identify those hybridomas that secrete antibodies against rabbit CD19. All IgG-producing hybridomas were screened by FACS analysis of rabbit peripheral blood mononuclear cells (PBMCs) double stained with a rabbit IgM binding antibody for B-cell identification.

Freshly isolated rabbit (PBMCs) were incubated with FITC labeled anti-rabbit IgM antibody (Southern Biotech) and IgG-positive hybridoma supernatants on ice. After 45 min. incubation the PBMCs were washed once with ice cold PBS and resuspended in an PE-labeled anti-mouse IgG antibody (Invitrogen) binding the murine IgG of the hybridoma supernatant. After another 45 min. incubation on ice the cells were washed again once with ice cold PBS. Finally, the PBMCs were resuspended in ice cold PBS and immediately subjected to the FACS analyses. DAPI-HCl in a concentration of 2 µg/ml (Cayman) was added prior to the FACS analyses to discriminate between dead and live cells. A Becton Dickinson FACS Canto II device equipped with a computer and the FACSDiva software (BD Biosciences) were used for the analysis.

After identification of the hybridoma supernatant binding to rabbit IgM positive B-cells the rabbit CD19 specificity was confirmed by FACS analysis of CHO or HEK293 cells transfected with rbCD19 expression plasmid. Cells transfected with rabbit-CD19 were used as positive cells, whereas non-transfected CHO or HEK293 cells served as negative control cells. The rabbit CD19 staining was performed as described in Example 7.

Example 3

Expression of CD19 Binding Antibodies

The antibody variable domain encoding sequences are generated by gene syntheses.

All sequences are verified by sequencing. All sequences are cloned into vectors that enable selection and propagation in E. coli (e.g. origin of replication from the vector pUC18, beta-lactamase for ampicillin resistance). These vectors additionally contain cassettes that enable expression in mammalian cells (e.g. origin of replication, oriP, of Epstein-Barr-Virus (EBV), the immediate early enhancer and promoter from the human cytomegalovirus (HCMV) and a polyadenylation sequence).

All gene segments that code for antibody light and heavy chains are preceded by a DNA sequence coding for a signal peptide (e.g. MGWSCIILFLVATATGVHS; SEQ ID NO: 55 or MPPPLLLAFL LFLTLGRVRP; SEQ ID NO: 56). The proteins are expressed by transient transfection human embryonic kidney HEK 293 cells in suspension. These cells are cultivated at 37° C. and 8% $CO_2$. On the day of transfection, cells are seeded in fresh medium at a density of $1-2\times10^6$ viable cells/mL. Equimolar amounts of both heavy and light chain plasmid DNAs are co-transfected. Cell culture supernatants are harvested 7 days after transfection, centrifuged (14,000×g for 45 min at 4° C.), and subsequently filtrated through a 0.22-µm filter. These supernatants could be frozen and stored at −20° C. before purification.

Example 4

Purification of CD19 Binding Antibodies

Cell free hybridoma supernatant is loaded onto a pre-equilibrated (phosphate buffered saline, PBS) protein A affinity column (MabSelect™ SuRe, GE Healthcare, 8×100 mm) with a contact time of 5 minutes. After washing (PBS, 5 column volumes) the antibody is eluted with 25 mM citric acid/NaOH (pH 3.0). The eluate is adjusted to pH 5.5 with 1 M Tris and incubated overnight at 4° C. Thereafter a final filtration (0.45 µm) is performed:

Example 5

Provision of CD19 ECD Expressing Cells and Binding of the Antibodies Thereto

Cells were transfected with plasmids encoding rabbit CD19 (SEQ ID NO: 01) extracellular domain (ECD) fused to the human PSCA GPI anchor sequence (DTDLCNASGA HALQPAAAIL ALLPALGLLL WGPGQL; SEQ ID NO: 52) for extracellular presentation. For transfection of NIH/3T3 cells for immunization, 1×10E7 cells were seeded out into three T175 flasks. Subsequently, the cells were reverse transfected in solution using Lipofectamine. The efficiency of transfection was determined using an FITC anti FLAG antibody (abcam) and FACS to 40% positive cells after 48 hours (FIG. 1 C). To confirm CD19 specificity by FACS analysis CHO or HEK293 cells were transfected with rbCD19. 3×10E5 HEK293 and 1×10E5 CHO cells were transfected using Lipofectamine. The expression was confirmed after 48 hours by FACS using an FITC anti FLAG antibody (abcam).

Example 6

Conjugating the Anti-Rabbit CD19 Antibody to a Detectable Label

The anti-rabbit CD19 antibody in phosphate buffer, pH 8.5, was adjusted to a protein concentration of about 5 mg/ml. D-biotinyl-aminocaproic acid-N-hydroxysuccinimide was dissolved in DMSO and added to the antibody solution in a molar ratio of 1:5. The reaction was stopped after 60 min. by adding L-lysine, and the surplus of the labeling reagent was removed by dialysis against 50 mM potassium phosphate buffer, with 150 mM NaCl, pH 7.5.

Example 7

Labeling of B-Cells with Labelled Anti-Rabbit CD19 Antibody Including Index Sort Approach B-cells were stained with anti-IgG FITC (1:200, AbD Serotec), anti-IgM PE (1:200 BD Pharmingen) and the anti-CD19 A647 (1:200, Roche) antibody in DPBS supplemented with normal mouse serum (1:20, Southern Biotech) for 30 min in the dark (4° C.). Subsequently, cells were washed and resuspended in ice-cold DPBS. Live/dead discrimination was achieved by adding propidium iodide (PI) in a concentration of 0.5 µg/ml (BD Pharmingen) shortly prior to single cell sort on a Becton Dickinson FACSAria equipped with a computer and the FACSDiva software (BD Biosciences). Single IgG+ and IgG+IgM+ cells were sorted into 96 well plates. The index sort tool of the FACSAria was applied to save the CD19 expression of each sorted cell. Cells were cultured as described in Example 9. After 7 days of culture, the supernatant was used to determine the number of IgG producing and antigen-specific clones by ELISA. A plugin was developed in FlowJo that combined ELISA data and FACS index sorted data. This plugin adds IgG positive and antigen-specific wells from ELISA to the fluorescent data from anti-rabbit IgG, anti-rabbit IgM, and anti-rabbit CD19 staining, thus IgG producing and antigen-specific clones can be visualized in FlowJo. Results show that all IgG producing and all antigen-specific clones are IgG and CD19 double positive. Furthermore, by checking the percentage of sorted double positive cells, sorting efficiency (more specific sorted cells) can be improved by about 14-20%.

Example 8

Immune Fluorescence Staining and Flow Cytometry Prior to B-Cell Culture

The anti-IgG FITC (AbD Serotec) and the anti-huCk PE (BD Bioscience) antibody were used for single cell sorting. For surface staining, cells from the depletion and enrichment step were incubated with the anti-IgG FITC and the anti-huCk PE antibody in PBS for 45 min. in the dark at 4° C. After staining the PBMCs were washed two fold with ice-cold PBS. Finally, the PBMCs were resuspended in ice-cold PBS and immediately subjected to the FACS analyses. Propidium iodide in a concentration of 0.5 µg/ml (BD Pharmingen) was added prior to the FACS analyses to discriminate between dead and live cells. A Becton Dickinson FACSAria equipped with a computer and the FACSDiva software (BD Biosciences) were used for single cell sort.

Example 9

B-Cell Culture

The cultivation of the rabbit B cells was performed by a method described by Seeber et al. (2014). Briefly, single-cell sorted rabbit B cells were incubated in 96-well plates with 200 µl/well EL-4 B5 medium containing Pansorbin Cells (1:100000) (Calbiochem) and the synthetic cytokine mix as described in this table:

| compound | final concentration |
| --- | --- |
| mIL-1b | 0.063 ng/ml |
| mTNF-alpha | 0.063 ng/ml |
| mIL-2 | 1.58 ng/ml |
| mIL-6 | 0.32 ng/ml |
| mIL-10 | 0.32 ng/ml |

In addition, 0.35 ng/µl phorbol myristate acetate and gamma-irradiated (4 Gy) murine EL-4 B5 thymoma cells (2×10E5 cells/well) were used and the cells were cultivated for 7 days at 37° C. in the incubator. The supernatants of the B-cell cultivation were removed for screening and the remaining cells were lysed in 100 µl RLT buffer (Qiagen) immediately and were frozen at −80° C.

Example 10

Determination of CD19-Positive B-Cells in Blood and Spleen

The blood was objected to density gradient centrifugation for isolation of PBMCs. The spleen was mashed and centrifuged prior to lysis of erythrocytes with a normal erythrocyte lysis buffer according to manufacturer's instructions. The cells from blood or spleen were seeded in a concentration of $6 \times 10^6$ PBMCs per well at maximum in 1 ml medium on sterile 6-well plates. The depletion of macrophages occurs by unspecific adhesion to the cell culture plates during 1 h incubation at 37° C. in the incubator. Isolated PBMCs were stained and washed as described in Example 7. Live/dead discrimination was achieved by DAPI (Biomol) in a concentration of 0.1 µg/ml shortly prior to analysis of cell populations on a Becton Dickinson FACSCanto equipped with a computer and the FACSDiva software (BD Biosciences). Analysis of CD19-positive B-cells in blood and spleen was performed with FlowJo v10.0.7.

Example 11

Counting of B-Cells after Co-Cultivation

B-cells were sorted and co-cultivated with feeder cells as described in Example 7 and 9. After 7 days of cultivation days, the 96 well culture plates were centrifuged at 300×g for 5 min, the medium removed and the pellet resuspended in ice-cold DPBS containing the anti-CD19 A647 antibody (1:400, Roche) and supplemented with normal mouse serum (1:20, Southern Biotech), for incubation of 30 min in the dark (4° C.). Subsequently, cells were washed and resuspended in a defined volume of ice-cold DPBS. Live/dead discrimination was achieved by adding DAPI (Biomol) in a concentration of 0.1 µg/ml shortly prior to analysis of cell populations on a Becton Dickinson FACSCanto equipped with a computer and the FACSDiva software (BD Biosciences). It is important to set a defined analysis volume at the FACSCanto and consider the total sample volume for exact calculation of total B-cell number per well. Analysis was performed with FlowJo v10.0.7 and the cell count of B-cells calculated with the number of CD19+ cells taking into consideration the total sample volume. With this method, it enables for the first time the counting of B cells within a B-cell clone after in-house B-cell cloning approach since e.g. cell surface IgG decreases during cultivation.

Example 12

Enrichment of CD19-Positive B-Cells Using the Antibody According to the Invention PBMCs from immunized rabbits were isolated from blood as described in example 10 and stained and cultivated as described in examples 8 and 9. Half of the cells were processed as follows: Biotinylated anti-rabbit CD19 was incubated for 15 min together with PBMCs at 4° C. in a 1:500 dilution. PBMC were washed with cold MACS buffer (Miltenyi) and then incubated with streptavidin MACS beads (Miltenyi) according to manufacturer instructions. Cells were washed with MACS buffer and subsequently purified using a Miltenyi LS column according to manufacturer instructions. Purified cells were incubated with fluorescently labeled antigen and anti-rabbit IgG FITC antibody (Southern Biotech) for 15 min at 4° C. and subsequently washed. The other half of the cells was first incubated with biotinylated antigen (1:10000) for 15 min at 4° C. Cells were washed and then incubated with streptavidin MACS beads according to manufacturer instructions. Cells were washed and subjected to a LS column. Cells were subsequently incubated with fluorescently labeled anti-rabbit CD19 and anti-rabbit IgG antibody. Finally, PBMCs were resuspended in ice-cold PBS and immediately sorted on a BD Aria III. 7-AAD (BD Pharmingen) was added according to manufacturer instructions to discriminate between dead and live cells. The first half of cells was gated on size, antigen positivity and IgG positivity. The second half of cells was gated on size, CD19 positivity, and IgG positivity. Cells were single cell sorted and cultivated as described in Example 9. After one week of incubation, number of IgG positive clones, specific clones, and cross-reactive clones were determined using ELISA. Enrichment with anti-rabbit CD19 resulted in increased viability of cells (FIGS. 7A-7B), increased number of IgG producing clones, and increased number of antigen-specific clones. Furthermore, the number of cross-reactive clones was reduced.

The invention claimed is:

1. An antibody binding to rabbit CD19 comprising
   (a) a HVR-H1 comprising the amino acid sequence of SEQ ID NO: 32 or 33 or 34,
   (b) a HVR-H2 comprising the amino acid sequence of SEQ ID NO: 35 or 36,
   (c) a HVR-H3 comprising the amino acid sequence of SEQ ID NO: 37,
   (d) a HVR-L1 comprising the amino acid sequence of SEQ ID NO: 38,
   (e) a HVR-L2 comprising the amino acid sequence of SEQ ID NO: 39, and
   (f) a HVR-L3 comprising the amino acid sequence of SEQ ID NO: 40.

2. The antibody according to claim 1, wherein the antibody is a monoclonal antibody.

3. The antibody according to claim 1, wherein the antibody is a chimeric or humanized antibody.

4. The antibody according to claim 1, wherein the antibody comprises a variable heavy chain domain of SEQ ID NO: 30 and a variable light chain domain of SEQ ID NO: 26.

5. The antibody according to claim 1, wherein the antibody is a full length antibody or an antibody fragment.

6. The antibody according to claim 1, wherein the antibody is conjugated to a detectable label.

7. The antibody according to claim 6, wherein the detectable label is a fluorescent dye.

8. A method for selecting a rabbit B-cell comprising the following steps:
   a) incubating a multitude of rabbit B-cells with an antibody according to claim 1
   b) selecting one or more B-cells to which the antibody according to claim 1 is bound and thereby selecting a rabbit B-cell.

9. The method according to claim 8 further comprising one or more of the following steps:
   after step b) and prior to step c): incubating the rabbit B-cells at 37° C. for one hour in co-cultivation medium, and/or
   c) single depositing one or more rabbit B-cells to which the antibody according to claim 1 is bound, and/or
   d) co-cultivating the single deposited rabbit B-cells with feeder cells in a co-cultivation medium, and/or
   e) selecting a rabbit B-cell proliferating in step d) and thereby selecting a rabbit B-cell.

10. A method for removing non B-cells for a cultivation comprising the following steps:
    a) co-cultivating rabbit B-cells, which have been deposited either as single cells or as pool of cells, with feeder cells,
    b) incubating the cells from the co-cultivation obtained in step a) with the antibody according to claim 1, and
    c) selecting one or more rabbit B-cells to which the antibody according to claim 1 is bound and thereby removing non-B-cells.

11. A method for determining the number B-cells in a co-cultivation of a single deposited B-cell with feeder cells comprising the following steps:
    a) co-cultivating a single deposited rabbit B-cell with feeder cells,
    b) incubating the cells from the co-cultivation obtained in step a) with the antibody according to claim 1, and
    c) determining the number of B-cells in the cultivation by counting the number of cells to which the antibody according to claim 1 is bound.

12. A method for co-cultivating one or more rabbit B-cells comprising the steps of
    incubating a multitude of rabbit B-cells/labelling individual B-cells of a multitude of rabbit B-cells with an antibody according to claim 1,
    selecting/depositing one or more rabbit B-cells that have the antibody according to any one of claims 1 to 7 bound to their surface/that have been labelled either as individual B-cells (single deposited B-cell) or as a pool of B-cells, and
    co-cultivating the single deposited rabbit B-cells or the pool of rabbit B-cells with feeder cells.

13. The method according to claim 9, wherein the co-cultivating is in the presence of a synthetic feeder mix that comprises IL-1β, TNFα, IL-10, and one or more selected from IL-21, SAC, BAFF, IL-2, IL-4, and IL-6.

14. A method for selecting B-cells comprising the following steps:
    a) obtaining B-cells from the blood of a rabbit,
    b) incubating the B-cells with an antibody according to claim 1, which is bound to a bead,
    c) removing non-bound B-cells,
    d) recovering the bound B-cells from the beads and thereby selecting one or more B-cells.

15. The method according to claim 14 further comprising the following steps
    e) optionally incubating the recovered B-cells at 37° C. for one hour in co-cultivation medium,
    f) depositing one or more recovered B-cells in an individual container,
    g) co-cultivating the deposited cells with a feeder cell in a co-cultivation medium,
    h) selecting a B-cell proliferating in step g) and thereby selecting a B-cell.

* * * * *

SEQUENCE LISTING

```
<160> NUMBER OF SEQ ID NOS: 56

<210> SEQ ID NO 1
<211> LENGTH: 523
<212> TYPE: PRT
<213> ORGANISM: Oryctolagus cuniculus

<400> SEQUENCE: 1

Gln Lys Leu Leu Gln Val Glu Met Glu Glu Gly Ser Asp Ala Val Leu
1               5                   10                  15

Pro Cys Leu Gln Asp Pro Pro Asp Gly Pro Pro Glu Arg Leu Ile Trp
                20                  25                  30

Ser Arg Asp Ser Gln Gly Pro Phe Leu Glu Leu Ser Pro Gly Ser Pro
            35                  40                  45

Gly Leu Gly Ile His Val Gly Arg Leu Gly Ile Leu Leu Leu Ile Phe
        50                  55                  60

Asn Val Ser Asn Glu Met Gly Gly Phe Tyr Leu Cys Gln Pro Ala Pro
65                  70                  75                  80

Pro Ser Gln Gln Ala Trp Gln Pro Gly Trp Thr Val Ser Val Glu Gly
                85                  90                  95

Ser Gly Glu Leu Phe Arg Trp Asn Ala Ser Asp Leu Gly Gly Pro Gly
                100                 105                 110

Cys Gly Leu Gly Asn Glu Ser Ser Ser Ser Gln Pro Tyr Val Trp Asp
            115                 120                 125

Arg Asp His Pro Lys Glu Trp Asp Met Gly Pro Ala Cys Ala Ser Pro
        130                 135                 140

Arg Gly Asp Leu Asn Gln Ser Ser Ser Leu Asp Leu Thr Val Ala Pro
145                 150                 155                 160

Gly Ser Thr Val Trp Leu Ser Cys Gly Val Pro Pro Ala Ser Val Ala
                165                 170                 175

Thr Gly Pro Val Ser Trp Ala His Ile His Pro Thr Lys Pro Asn Ile
                180                 185                 190

Leu Leu Pro Ser Leu Asn Leu Thr Ala Glu Ser Pro Ala Arg Glu Met
            195                 200                 205

Trp Val Leu Gly Pro Val Leu Met Leu Pro Gln Val Thr Ala Val Asp
        210                 215                 220

Ala Gly Met Tyr Val Cys Arg Arg Gly Asn Leu Thr Thr Glu Ile His
225                 230                 235                 240

Val Thr Ile Thr Val Arg Pro Ala Ile Trp His Trp Leu Gln Arg Lys
                245                 250                 255
```

```
Ser Gly Trp Ile Val Pro Val Val Ala Leu Leu Tyr Leu Ile Phe Cys
            260                 265                 270

Leu Gly Cys Leu Val Ser Phe Leu His Leu Arg Arg Ala Leu Ile Leu
        275                 280                 285

Arg Arg Lys Arg Lys Arg Met Thr Asp Pro Thr Arg Arg Phe Phe Lys
    290                 295                 300

Val Thr Pro Pro Ala Gly Asn Gly Ala Gln Ser Gln Tyr Gly Asn Val
305                 310                 315                 320

Leu Ser Leu Pro Thr Pro Thr Ser Gly Thr Gly Arg Ala Gln Arg Trp
                325                 330                 335

Ala Ala Ser Leu Gly Gly Ala Ala Pro Tyr Gly His Pro Leu Ser
        340                 345                 350

Asp Val Gln Glu Ala Gly Ala Ala Gly Ser Arg Ser Leu Pro Arg Ala
        355                 360                 365

Ser Pro Glu Glu Glu Gly Glu Ala Tyr Glu Glu Pro Asp Ser Glu
        370                 375                 380

Ala Asp Ser Glu Phe Tyr Glu Asn Asp Ser Asn Pro Ala Gln Asp Gln
385                 390                 395                 400

Leu Ser Gln Asp Gly Ser Gly Tyr Glu Asn Pro Glu Glu Pro Ser
                405                 410                 415

Gly Pro Glu Asp Asp Asp Ser Phe Ser Asn Ala Glu Ser Tyr Glu Asn
                420                 425                 430

Glu Asp Glu Glu Leu Ala Pro Pro Val Thr Arg Thr Ala Asp Phe Leu
        435                 440                 445

Ser Pro His Gly Ser Ala Trp Asp Pro Ser Arg Glu Ala Val Ser Leu
    450                 455                 460

Gly Ser Gln Ser Tyr Glu Asp Met Arg Gly Ile Leu Tyr Ala Ala Pro
465                 470                 475                 480

Gln Leu Arg Ser Ser Arg Pro Gly Pro Ser Tyr Glu Asp Ala Asp
                485                 490                 495

Ser Tyr Glu Asn Met Asp Asn Pro Asp Gly Pro Glu Pro Ala Trp Gly
                500                 505                 510

Ala Gly Gly His Gly Gly Thr Trp Ser Thr Arg
        515                 520

<210> SEQ ID NO 2
<211> LENGTH: 543
<212> TYPE: PRT
<213> ORGANISM: Oryctolagus cuniculus

<400> SEQUENCE: 2

Met Pro Pro Pro Leu Leu Leu Ala Phe Leu Leu Phe Leu Thr Leu Gly
1               5                   10                  15

Arg Val Arg Pro Gln Lys Leu Leu Gln Val Glu Met Glu Glu Gly Ser
            20                  25                  30

Asp Ala Val Leu Pro Cys Leu Gln Asp Pro Asp Gly Pro Pro Glu
        35                  40                  45

Arg Leu Ile Trp Ser Arg Asp Ser Gln Gly Pro Phe Leu Glu Leu Ser
    50                  55                  60

Pro Gly Ser Pro Gly Leu Gly Ile His Val Gly Arg Leu Gly Ile Leu
65                  70                  75                  80

Leu Leu Ile Phe Asn Val Ser Asn Glu Met Gly Gly Phe Tyr Leu Cys
                85                  90                  95

Gln Pro Ala Pro Pro Ser Gln Gln Ala Trp Gln Pro Gly Trp Thr Val
            100                 105                 110
```

```
Ser Val Glu Gly Ser Gly Glu Leu Phe Arg Trp Asn Ala Ser Asp Leu
        115                 120                 125

Gly Gly Pro Gly Cys Gly Leu Gly Asn Glu Ser Ser Ser Gln Pro
130                 135                 140

Tyr Val Trp Asp Arg Asp His Pro Lys Glu Trp Asp Met Gly Pro Ala
145                 150                 155                 160

Cys Ala Ser Pro Arg Gly Asp Leu Asn Gln Ser Ser Ser Leu Asp Leu
                165                 170                 175

Thr Val Ala Pro Gly Ser Thr Val Trp Leu Ser Cys Gly Val Pro Pro
            180                 185                 190

Ala Ser Val Ala Thr Gly Pro Val Ser Trp Ala His Ile His Pro Thr
        195                 200                 205

Lys Pro Asn Ile Leu Leu Pro Ser Leu Asn Leu Thr Ala Glu Ser Pro
210                 215                 220

Ala Arg Glu Met Trp Val Leu Gly Pro Val Leu Met Leu Pro Gln Val
225                 230                 235                 240

Thr Ala Val Asp Ala Gly Met Tyr Val Cys Arg Arg Gly Asn Leu Thr
                245                 250                 255

Thr Glu Ile His Val Thr Ile Thr Val Arg Pro Ala Ile Trp His Trp
            260                 265                 270

Leu Gln Arg Lys Ser Gly Trp Ile Val Pro Val Val Ala Leu Leu Tyr
        275                 280                 285

Leu Ile Phe Cys Leu Gly Cys Leu Val Ser Phe Leu His Leu Arg Arg
        290                 295                 300

Ala Leu Ile Leu Arg Arg Lys Arg Lys Arg Met Thr Asp Pro Thr Arg
305                 310                 315                 320

Arg Phe Phe Lys Val Thr Pro Pro Ala Gly Asn Gly Ala Gln Ser Gln
                325                 330                 335

Tyr Gly Asn Val Leu Ser Leu Pro Thr Pro Thr Ser Gly Thr Gly Arg
            340                 345                 350

Ala Gln Arg Trp Ala Ala Ser Leu Gly Gly Ala Ala Ala Pro Tyr Gly
        355                 360                 365

His Pro Leu Ser Asp Val Gln Glu Ala Gly Ala Ala Gly Ser Arg Ser
        370                 375                 380

Leu Pro Arg Ala Ser Pro Glu Glu Glu Gly Glu Ala Tyr Glu Glu
385                 390                 395                 400

Pro Asp Ser Glu Ala Asp Ser Glu Phe Tyr Glu Asn Asp Ser Asn Pro
                405                 410                 415

Ala Gln Asp Gln Leu Ser Gln Asp Gly Ser Gly Tyr Glu Asn Pro Glu
            420                 425                 430

Glu Glu Pro Ser Gly Pro Glu Asp Asp Ser Phe Ser Asn Ala Glu
        435                 440                 445

Ser Tyr Glu Asn Glu Asp Glu Glu Leu Ala Pro Pro Val Thr Arg Thr
450                 455                 460

Ala Asp Phe Leu Ser Pro His Gly Ser Ala Trp Asp Pro Ser Arg Glu
465                 470                 475                 480

Ala Val Ser Leu Gly Ser Gln Ser Tyr Glu Asp Met Arg Gly Ile Leu
                485                 490                 495

Tyr Ala Ala Pro Gln Leu Arg Ser Ser Arg Pro Gly Pro Ser Tyr Glu
            500                 505                 510

Glu Asp Ala Asp Ser Tyr Glu Asn Met Asp Asn Pro Asp Gly Pro Glu
        515                 520                 525
```

```
Pro Ala Trp Gly Ala Gly Gly His Gly Gly Thr Trp Ser Thr Arg
    530                 535                 540
```

<210> SEQ ID NO 3
<211> LENGTH: 1632
<212> TYPE: DNA
<213> ORGANISM: Oryctolagus cuniculus

<400> SEQUENCE: 3

```
atgccacctc ctctcctgct cgccttcctc ctcttcctga ccctggggag agtcaggccc      60
cagaaactac tgcaggtgga gatggaagag gaagtgatg ctgtgttgcc gtgcctccag      120
gacccccgg atggtcccc tgagcggctg atctggtctc gggactccca agggcctttc      180
ctggagctga gccccgggtc cccaggcctg gcatccatg tggggcgtct tggcatcttg      240
ctgctcatct tcaacgtctc taatgagatg ggggcttct acctgtgcca gccagcgccc      300
ccctcccagc aggcctggca gcctggttgg acggtcagcg tggagggcag cggggagctc      360
ttccggtgga atgcttcgga cctaggtggc ccaggctgtg gctgggcaa tgagtcttcc      420
agctcccagc cgtacgtgtg ggacagagac caccccaagg agtgggacat ggggcctgcc      480
tgcgcttccc ccaggggtga tctgaaccag agctccagcc tggacctcac cgtggcccct      540
ggctccactg tctggctgtc ctgtggggtg ccccctgcct ctgtggccac tggccccgtt      600
tcctgggccc acatacaccc tacgaagccc aacatcttat tgccaagcct aaacctgacc      660
gcggaatccc cagcaagaga gatgtgggtc ctggggcctg ttctgatgct gccccaggtc      720
acagctgtgg atgctgggat gtatgtctgt cgccgtggca acctgaccac ggaaattcac      780
gtgacaatca ctgtccggcc agcaatatgg cactggctgc agaggaaaag cggctggatt      840
gttccagttg tggcttttgct ttatctgatc ttctgcctgg gctgcctggt gagctttctt      900
caccttcgga gagccctgat cctgagaagg aaaagaaaga aatgacgga ccccaccagg      960
agattcttca agtgacgcc cccgcagga acggggctc agagccagta tgggaacgtg      1020
ctctctcttc ccacgccac ctctggcaca ggacgcgccc agcgttgggc ggcaagcctg      1080
gggggcgccg ccgcaccta tggacatccg ctcagcgacg tccaggaggc tggagccgcg      1140
gggtcccgga gcctgccaag agccagccca gaagaagagg aaggggaggc ctacgaggag      1200
ccggacagtg aggcggactc cgagttctac gagaacgact ctaacccggc caggaccag      1260
ctctcccaag acggcagcgg ctatgagaac cccgaggagg agccgtcggg tcctgaggac      1320
gatgactcct tctccaacgc cgagtcctat gagaatgagg atgaggagct ggccccgccg      1380
gtcaccagga cagcagactt cctgagcccc acgggtctg cctgggaccc cagcggggaa      1440
gcagtctccc ttggctccca gtcctatgag gatatgagag ggatcctgta cgcggctccc      1500
cagctccgct cctcacggcc agggccctct tatgaggaag atgcagactc ttacgagaac      1560
atggacaatc ccgacgggcc agaaccagcg tggggagcag ggggccatgg ggggacctgg      1620
agcactaggt ga                                                          1632
```

<210> SEQ ID NO 4
<211> LENGTH: 437
<212> TYPE: PRT
<213> ORGANISM: Cricetulus griseus

<400> SEQUENCE: 4

```
Met Pro Ser Pro Leu Ser Leu Ser Phe Leu Leu Phe Leu Thr Leu Val
1               5                   10                  15

Glu Gly Thr Ser Gln Lys Pro Leu Leu Leu Glu Val Glu Glu Gly Ser
```

```
            20                  25                  30
Asn Leu Val Leu Pro Cys Leu Pro Asp Pro Ser Pro Asn Ser Thr Glu
            35                  40                  45
Lys Leu Ala Trp Tyr Arg Gly Asn Gln Ser Thr Pro Phe Leu Glu Leu
            50                  55                  60
Ser Leu Gly Ser Pro Gly Leu Gly Leu Arg Val Gly Ser Leu Gly Ile
65                  70                  75                  80
Leu Leu Val Ile Val Asn Ala Ser Asp His Met Gly Gly Phe Tyr Leu
                85                  90                  95
Cys Gln Asn Gly Pro Pro Phe Lys Asp Thr Trp Gln Pro Ala Trp Thr
            100                 105                 110
Val Asn Val Glu Asp Ser Gly Glu Leu Phe Arg Trp Asn Ala Ser Asp
            115                 120                 125
Val Arg Asp Leu Asp Cys Gly Leu Glu Asn Arg Ser Ser Gly Ser His
            130                 135                 140
Arg Pro Ser Ser Gly Ser His Asn Ser Ser Trp Leu Tyr Val Trp Ala
145                 150                 155                 160
Lys Asp His Pro Glu Val Val Gly Thr Lys Pro Val Cys Ala Pro Gln
                165                 170                 175
Arg Ile Ser Leu Asn Gln Ser Leu Ile Asn Gln Asp Leu Thr Val Ala
            180                 185                 190
Pro Gly Ser Thr Leu Trp Leu Ser Cys Gly Val Pro Pro Val Pro Val
            195                 200                 205
Thr Arg Gly Ser Ile Ser Trp Thr Arg Val His Pro Arg Arg Pro Asn
            210                 215                 220
Val Ser Leu Leu Asn Leu Ser Leu Trp Glu Glu His Pro Val Arg Glu
225                 230                 235                 240
Met Trp Val Trp Gly Pro Val Leu Ser Leu Pro Gln Ala Thr Ala Leu
                245                 250                 255
Asp Glu Gly Ile Tyr Tyr Cys Leu His Gly Gly Leu Thr Ile Glu Met
            260                 265                 270
His Val Lys Val Asn Glu Arg Phe Phe Lys Val Thr Pro Pro Ser Gly
            275                 280                 285
Asn Gly Thr Gln Asn Gln Tyr Gly Asn Val Leu Ser Leu Pro Thr Pro
            290                 295                 300
Thr Ser Gly Ser Ala His Ala Gln Arg Trp Ala Ala Gly Leu Ala Ser
305                 310                 315                 320
Ala Pro Gly Ser Tyr Gly Asn Pro Arg Ile Glu Val Gln Asp Thr Gly
                325                 330                 335
Ala Gln Ser His Glu Thr Gly Leu Glu Glu Glu Glu Gly Glu Gly
            340                 345                 350
Tyr Glu Glu Pro Asp Ser Glu Gly Ser Glu Phe Tyr Glu Asn Asp
            355                 360                 365
Ser Asn Leu Gly Gln Glu Gln Leu Ser Gln Asp Gly Ser Asp Tyr Glu
            370                 375                 380
Asn Pro Glu Asp Glu Pro Met Gly Pro Glu Glu Asp Ser Phe Ser
385                 390                 395                 400
Asn Ala Glu Ser Tyr Glu Asn Ala Asp Glu Leu Ala Gln Pro Val
                405                 410                 415
Gly Arg Thr Met Gly Val Tyr Ala Arg Val Leu Pro Glu Pro Pro Arg
            420                 425                 430
Ile Cys Leu Gly Pro
            435
```

<210> SEQ ID NO 5
<211> LENGTH: 547
<212> TYPE: PRT
<213> ORGANISM: Mus musculus

<400> SEQUENCE: 5

```
Met Pro Ser Pro Leu Pro Val Ser Phe Leu Leu Phe Leu Thr Leu Val
1               5                   10                  15

Gly Gly Arg Pro Gln Lys Ser Leu Leu Val Glu Val Glu Glu Gly Gly
            20                  25                  30

Asn Val Val Leu Pro Cys Leu Pro Asp Ser Ser Pro Val Ser Ser Glu
        35                  40                  45

Lys Leu Ala Trp Tyr Arg Gly Asn Gln Ser Thr Pro Phe Leu Glu Leu
    50                  55                  60

Ser Pro Gly Ser Pro Gly Leu Gly Leu His Val Gly Ser Leu Gly Ile
65                  70                  75                  80

Leu Leu Val Ile Val Asn Val Ser Asp His Met Gly Gly Phe Tyr Leu
                85                  90                  95

Cys Gln Lys Arg Pro Pro Phe Lys Asp Ile Trp Gln Pro Ala Trp Thr
            100                 105                 110

Val Asn Val Glu Asp Ser Gly Glu Met Phe Arg Trp Asn Ala Ser Asp
        115                 120                 125

Val Arg Asp Leu Asp Cys Asp Leu Arg Asn Arg Ser Ser Gly Ser His
    130                 135                 140

Arg Ser Thr Ser Gly Ser Gln Leu Tyr Val Trp Ala Lys Asp His Pro
145                 150                 155                 160

Lys Val Trp Gly Thr Lys Pro Val Cys Ala Pro Arg Gly Ser Ser Leu
                165                 170                 175

Asn Gln Ser Leu Ile Asn Gln Asp Leu Thr Val Ala Pro Gly Ser Thr
            180                 185                 190

Leu Trp Leu Ser Cys Gly Val Pro Pro Val Pro Val Ala Lys Gly Ser
        195                 200                 205

Ile Ser Trp Thr His Val His Pro Arg Arg Pro Asn Val Ser Leu Leu
    210                 215                 220

Ser Leu Ser Leu Gly Gly Glu His Pro Val Arg Glu Met Trp Val Trp
225                 230                 235                 240

Gly Ser Leu Leu Leu Leu Pro Gln Ala Thr Ala Leu Asp Glu Gly Thr
                245                 250                 255

Tyr Tyr Cys Leu Arg Gly Asn Leu Thr Ile Glu Arg His Val Lys Val
            260                 265                 270

Ile Ala Arg Ser Ala Val Trp Leu Trp Leu Leu Arg Thr Gly Gly Trp
        275                 280                 285

Ile Val Pro Val Val Thr Leu Val Tyr Val Ile Phe Cys Met Val Ser
    290                 295                 300

Leu Val Ala Phe Leu Tyr Cys Gln Arg Ala Phe Ile Leu Arg Arg Lys
305                 310                 315                 320

Arg Lys Arg Met Thr Asp Pro Ala Arg Arg Phe Phe Lys Val Thr Pro
                325                 330                 335

Pro Ser Gly Asn Gly Thr Gln Asn Gln Tyr Gly Asn Val Leu Ser Leu
            340                 345                 350

Pro Thr Ser Thr Ser Gly Gln Ala His Ala Gln Arg Trp Ala Ala Gly
        355                 360                 365

Leu Gly Ser Val Pro Gly Ser Tyr Gly Asn Pro Arg Ile Gln Val Gln
```

```
              370                 375                 380
Asp Thr Gly Ala Gln Ser His Glu Thr Gly Leu Glu Glu Gly Glu
385                 390                 395                 400

Ala Tyr Glu Glu Pro Asp Ser Glu Glu Gly Glu Phe Tyr Glu Asn
                405                 410                 415

Asp Ser Asn Leu Gly Gln Asp Gln Val Ser Gln Asp Gly Ser Gly Tyr
                420                 425                 430

Glu Asn Pro Glu Asp Glu Pro Met Gly Pro Glu Glu Asp Ser Phe
                435                 440                 445

Ser Asn Ala Glu Ser Tyr Glu Asn Ala Asp Glu Glu Leu Ala Gln Pro
450                 455                 460

Val Gly Arg Met Met Asp Phe Leu Ser Pro His Gly Ser Ala Trp Asp
465                 470                 475                 480

Pro Ser Arg Glu Ala Ser Ser Leu Gly Ser Gln Ser Tyr Glu Asp Met
                485                 490                 495

Arg Gly Ile Leu Tyr Ala Ala Pro Gln Leu His Ser Ile Gln Ser Gly
                500                 505                 510

Pro Ser His Glu Glu Asp Ala Asp Ser Tyr Glu Asn Met Asp Lys Ser
                515                 520                 525

Asp Asp Leu Glu Pro Ala Trp Glu Gly Glu Gly His Met Gly Thr Trp
530                 535                 540

Gly Thr Thr
545

<210> SEQ ID NO 6
<211> LENGTH: 547
<212> TYPE: PRT
<213> ORGANISM: Rattus norvegicus

<400> SEQUENCE: 6

Met Pro Ser Pro Leu Pro Val Ser Leu Leu Phe Leu Thr Leu Val
1               5                   10                  15

Gly Gly Arg Pro Gln Asn Ser Leu Leu Val Glu Val Glu Glu Gly Asp
                20                  25                  30

Asn Val Val Leu Ser Cys Leu Arg Asp Ser Ser Pro Val Ser Ser Glu
                35                  40                  45

Lys Leu Ala Trp Tyr Arg Gly Asn Gln Ser Thr Pro Phe Leu Glu Leu
50                  55                  60

Ser Leu Arg Ser Pro Asp Leu Gly Leu His Ile Gly Pro Leu Gly Ile
65                  70                  75                  80

Leu Leu Val Ile Val Asn Val Ser Asp His Arg Gly Phe Tyr Leu
                85                  90                  95

Cys Gln Lys Arg Pro Ser Phe Lys Asp Thr Trp Gln Pro Ala Trp Thr
                100                 105                 110

Val Asn Val Glu Asp Ser Gly Glu Leu Phe Arg Trp Asn Ala Ser Asp
                115                 120                 125

Leu Gly Asp Leu Asp Cys Asp Leu Gly Asn Arg Ser Gly Ser His
                130                 135                 140

Arg Ser Thr Ser Gly Ser Gln Leu Tyr Val Trp Ala Thr Asp His Pro
145                 150                 155                 160

Glu Val Trp Lys Thr Lys Pro Val Cys Ala Pro Arg Glu Ile Ser Leu
                165                 170                 175

Asn Gln Ser Leu Ile Asn Gln Asp Leu Thr Val Ala Pro Gly Ser Thr
                180                 185                 190
```

```
Leu Trp Leu Ser Cys Gly Val Pro Val Pro Val Thr Lys Gly Ser
            195                 200                 205

Ile Ser Trp Thr His Val His Pro Lys Thr Leu Asn Val Ser Leu Leu
210                 215                 220

Ser Leu Ser Leu Gly Gly Glu His Pro Val Arg Glu Met Trp Val Trp
225                 230                 235                 240

Gly Ser Leu Leu Leu Pro Gln Ala Lys Ala Ser Asp Glu Gly Thr
            245                 250                 255

Tyr Tyr Cys Leu Gln Gly Gly Leu Thr Ile Lys Met His Val Lys Val
            260                 265                 270

Ile Ala Arg Ser Ala Val Trp Leu Trp Leu Arg Thr Gly Gly Trp
            275                 280                 285

Ile Val Pro Val Val Thr Leu Val Tyr Val Ile Phe Cys Met Val Ser
            290                 295                 300

Met Ala Ala Phe Leu Tyr Phe Arg Arg Ala Phe Ile Leu Arg Arg Lys
305                 310                 315                 320

Arg Lys Arg Met Thr Asp Pro Ala Arg Arg Phe Phe Lys Val Thr Pro
                325                 330                 335

Pro Ser Gly Asn Gly Thr Gln Asn Gln Tyr Gly Asn Val Leu Ser Leu
            340                 345                 350

Pro Thr Ser Thr Ser Gly Gln Ala His Ala Gln Arg Trp Ala Ala Ser
            355                 360                 365

Leu Gly Ser Gly Pro Val Ser Tyr Gly Asn Pro Arg Ile Glu Val Gln
            370                 375                 380

Asp Ala Gly Ala Gln Arg His Glu Thr Gly Leu Glu Glu Gly Glu
385                 390                 395                 400

Ala Tyr Glu Glu Pro Asp Ser Glu Glu Gly Ser Glu Phe Tyr Glu Asn
                405                 410                 415

Asp Ser Asn Leu Glu Gln Asp Gln Leu Ser Gln Asp Gly Ser Gly Tyr
            420                 425                 430

Glu Asn Pro Glu Asp Asp Pro Val Gly Pro Glu Glu Asp Ser Phe
            435                 440                 445

Ser Asn Ala Glu Ser Tyr Glu Asn Ala Asp Glu Glu Leu Ala Gln Pro
450                 455                 460

Val Gly Arg Thr Met Asp Phe Leu Ser Pro His Gly Ser Ala Trp Asp
465                 470                 475                 480

Pro Ser Arg Glu Ala Ser Ser Leu Gly Ser Gln Ser Tyr Glu Asp Met
                485                 490                 495

Arg Gly Ile Leu Tyr Ala Ala Pro Gln Leu Gln Ser Ile Arg Ser Gly
                500                 505                 510

Pro Ser His Glu Glu Asp Ala Asp Ser Tyr Glu Asn Met Asp Lys Ser
            515                 520                 525

Asp Asp Pro Glu Pro Ala Trp Ala Gly Glu Gly His Met Gly Thr Trp
530                 535                 540

Gly Ala Thr
545

<210> SEQ ID NO 7
<211> LENGTH: 546
<212> TYPE: PRT
<213> ORGANISM: Ictidomys tridecemlineatus

<400> SEQUENCE: 7

Met Cys Asp His Trp His Pro Ser Ser Ile Thr Ala Gly Arg Ile Leu
1               5                   10                  15
```

-continued

```
Pro Thr Leu Gln Val His Trp Gln Gly Ser Pro Gly Leu Pro Pro Glu
            20                  25                  30

Gly Lys Glu Ile Leu Leu Pro Cys Leu Gln Asp His Ala Pro Ser Gln
        35                  40                  45

Gln Leu Ala Trp Ser Arg Gly Asn Gln Ser Glu Pro Phe Leu Glu Leu
    50                  55                  60

Ser Leu Gly Leu Pro Asp Leu Asp Val Leu Val Gly His Leu Gly Ile
65                  70                  75                  80

Leu Leu Val Phe Asn Val Ser His Gln Met Gly Gly Phe Tyr Leu Cys
                85                  90                  95

Arg Ser Gly Pro Pro Ser Lys Asp Thr Trp Arg Pro Gly Trp Thr Val
            100                 105                 110

Ser Val Glu Gly Ser Gly Glu Leu Phe Arg Trp Asn Ala Ser Asp Leu
        115                 120                 125

Glu Ala Leu Lys Cys Ser Arg Gly Asn Met Ser Ser Gly Thr Gly
    130                 135                 140

Leu Ser Ser Ala Pro Pro Asn Thr Ser Gln Leu Tyr Val Trp Ala Lys
145                 150                 155                 160

Asp His Pro Lys Ile Trp Asn Thr Glu Pro Val Cys Ala Pro Arg
                165                 170                 175

Gly Ser Leu Lys Gln Ser Phe Asn Gln Asp Leu Thr Val Ala Pro Asn
            180                 185                 190

Ser Thr Leu Trp Leu Ser Cys Gly Gly Phe Pro Thr Pro Val Val Ser
        195                 200                 205

Gly Pro Leu Ser Trp Ile Phe Arg Arg Pro Val Lys Ser His Ile Ser
    210                 215                 220

Leu Leu Asn Leu Ser Leu Ser Lys Glu Ala Pro Ser Arg Asp Met Trp
225                 230                 235                 240

Val Arg Gly Ser Val Leu Ser Leu Pro Gln Ala Thr Ala Gln Asp Ala
                245                 250                 255

Gly Thr Tyr Tyr Cys Leu Arg Asp Asn Leu Thr Ile Glu Ile Arg Val
            260                 265                 270

Lys Val Thr Ala Arg Thr Val Trp His Trp Leu Leu Thr Thr Gly Gly
        275                 280                 285

Trp Lys Val Pro Leu Val Thr Leu Val Tyr Leu Ile Phe Cys Leu Gly
    290                 295                 300

Ser Leu Val Ala Phe Leu His Leu Arg Arg Ala Leu Ile Gln Arg Arg
305                 310                 315                 320

Leu Arg Lys Arg Met Ile Asp Pro Thr Arg Arg Phe Phe Lys Val Thr
                325                 330                 335

Pro Pro Gln Gly Asn Gly Thr Gln Asn Gln Tyr Gly Asn Val Leu Ser
            340                 345                 350

Leu Pro Thr Pro Thr Ser Gly Pro Gly Arg Thr Lys Arg Trp Ala Ala
        355                 360                 365

Gly Met Gly Ser Ala Ser Leu Ser Tyr Gly Asn Pro Arg Arg Asp Ala
    370                 375                 380

Gln Glu Ala Gly Thr Pro Glu Ala Gly Leu Glu Glu Gly Glu Gly
385                 390                 395                 400

Tyr Glu Glu Pro Asp Ser Glu Glu Gly Ser Glu Phe Tyr Glu Asn Asp
                405                 410                 415

Ser Asn Leu Gly Arg Asp Gln Leu Ser Gln Asp Gly Ser Gly Tyr Glu
            420                 425                 430
```

Asn Pro Glu Asp Gly Ser Leu Gly Pro Glu Asp Ala Asp Ser Phe Ser
            435                 440                 445

Asn Ala Glu Ser Tyr Glu Asn Glu Asp Glu Leu Ala Pro Pro Val
    450                 455                 460

Thr Lys Thr Met Asp Phe Leu Ser Pro His Gly Ser Ala Arg Asp Pro
465                 470                 475                 480

Ser Arg Glu Ala Thr Ser Leu Gly Ser Gln Ser Tyr Glu Asp Met Arg
            485                 490                 495

Gly Ile Leu Tyr Val Ala Pro Gln Leu Arg Pro Leu Arg Thr Gly Pro
            500                 505                 510

Asn His Glu Glu Asp Ala Asp Ser Tyr Glu Asn Met Asp Asn Pro Asp
            515                 520                 525

Glu Pro Glu Pro Ala Trp Gly Gly Gly Arg Met Gly Ala Trp Ser
    530                 535                 540

Asn Arg
545

<210> SEQ ID NO 8
<211> LENGTH: 558
<212> TYPE: PRT
<213> ORGANISM: Callithrix jacchus

<400> SEQUENCE: 8

Met Pro Pro Ala Cys Leu Leu Phe Phe Leu Leu Phe Leu Thr Pro Met
1               5                   10                  15

Gly Val Arg Pro Gln Glu Pro Arg Leu Val Lys Val Glu Glu Gly Asp
            20                  25                  30

Asp Ala Met Leu Leu Cys Leu Glu Glu Thr Ser Gln Asp Pro Ala Gln
        35                  40                  45

Gln Val Ala Trp Trp Arg Glu Ser Pro Ser Leu Glu Pro Phe Leu Lys
    50                  55                  60

Leu Asn Leu Gly Leu Pro Gly Leu Gly Phe His Val Gly Pro Trp Gly
65                  70                  75                  80

Ile Trp Leu Phe Ile Phe Asn Val Ser His Gln Met Gly Gly Phe Tyr
                85                  90                  95

Leu Cys Gln Pro Gly Pro Pro Ser Glu Lys Ala Trp Gln Pro Gly Trp
            100                 105                 110

Thr Val Ser Val Glu Gly Ser Gly Glu Leu Phe Arg Trp Asn Ala Ser
        115                 120                 125

Asp Leu Ser Gly Gln Gly Cys Gly Leu Glu Asn Arg Ser Ser Glu Asp
    130                 135                 140

Pro Ser Ser Pro Ser Gly Asn Leu Met Ser Ser Gln Leu Tyr Val Trp
145                 150                 155                 160

Ala Lys Asp Arg Pro Lys Ile Trp Glu Gly Glu Pro Pro Cys Gly Leu
                165                 170                 175

Leu Arg Asp Ser Leu Asn Gln Thr Leu Ser Gln Asp Leu Thr Met Ala
            180                 185                 190

Pro Gly Ser Thr Leu Trp Leu Ser Cys Gly Val Pro Pro Asp Ser Val
        195                 200                 205

Ser Arg Gly Pro Leu Ser Trp Thr His Val Arg Pro Lys Glu Thr Asn
    210                 215                 220

Phe Ser Leu Leu Ser Leu Glu Leu Lys Asp Asn Arg Pro Ala Arg Asp
225                 230                 235                 240

Met Trp Val Met Glu Lys Gly Leu Leu Leu Pro Gln Ala Thr Ala Gln
                245                 250                 255

```
Asp Ala Gly Lys Tyr Tyr Cys His Arg Gly Asn Leu Thr Ile Ser Trp
            260                 265                 270

His Leu Glu Ile Thr Ala Arg Ser Ala Leu Trp His Trp Leu Val Arg
        275                 280                 285

Thr Gly Gly Trp Lys Val Leu Ala Val Thr Leu Thr Tyr Met Ile Phe
    290                 295                 300

Cys Leu Gly Ser Leu Val Gly Ile Leu His Leu Gln Arg Ala Leu Val
305                 310                 315                 320

Leu Arg Arg Lys Arg Lys Arg Met Thr Asp Pro Thr Arg Arg Phe Phe
                325                 330                 335

Lys Val Thr Pro Pro Gly Ser Gly Pro Gln Asn Gln Tyr Gly Asn
            340                 345                 350

Val Leu Ser Leu Pro Thr Pro Thr Ser Gly Leu Gly Arg Ala Gln Arg
        355                 360                 365

Trp Ala Ala Gly Leu Gly Gly Thr Ala Pro Ser Tyr Arg Asn Pro Arg
    370                 375                 380

Ser Asp Val Glu Ala Asp Gly Thr Val Gly Ser Arg Ser Pro Pro Gly
385                 390                 395                 400

Ala Gly Pro Glu Glu Glu Gly Glu Gly Tyr Glu Glu Pro Asp Ser
            405                 410                 415

Glu Glu Gly Ser Glu Phe Tyr Glu Asn Asp Ser Ser Leu Gly Gln Asp
        420                 425                 430

Gln Leu Ser Gln Asp Gly Ser Gly Tyr Glu Asn Pro Glu Asp Glu Pro
    435                 440                 445

Leu Gly Pro Glu Asp Glu Asp Ser Phe Ser Asn Ala Glu Ser Tyr Glu
    450                 455                 460

Asn Glu Asp Glu Glu Leu Thr Gln Pro Val Ser Arg Thr Met Asp Phe
465                 470                 475                 480

Leu Ser Pro His Gly Ser Ala Trp Asp Pro Ser Arg Glu Ala Thr Ser
            485                 490                 495

Leu Gly Ser Gln Ser Tyr Glu Asp Met Arg Gly Ile Leu Tyr Ser Ala
        500                 505                 510

Pro Gln Leu Arg Ser Ile Arg Gly Gln Pro Gly Pro Asn His Glu Glu
    515                 520                 525

Asp Ala Asp Ser Tyr Glu Asn Met Asp Asn Pro Asp Arg Pro Asp Pro
530                 535                 540

Pro Trp Gly Gly Gly Gly His Val Gly Thr Trp Gly Ala Arg
545                 550                 555

<210> SEQ ID NO 9
<211> LENGTH: 557
<212> TYPE: PRT
<213> ORGANISM: Macaca mulatta

<400> SEQUENCE: 9

Met Pro Pro Pro Cys Leu Leu Phe Phe Leu Phe Leu Thr Pro Met
1               5                   10                  15

Glu Val Arg Pro Gln Glu Pro Leu Val Val Lys Val Glu Glu Gly Asp
            20                  25                  30

Asn Ala Val Leu Gln Cys Leu Glu Gly Thr Ser Asp Gly Pro Thr Gln
        35                  40                  45

Gln Leu Val Trp Cys Arg Asp Ser Pro Phe Glu Pro Phe Leu Asn Leu
    50                  55                  60

Ser Leu Gly Leu Pro Gly Met Gly Ile Arg Met Gly Pro Leu Gly Ile
```

```
           65                  70                  75                  80
Trp Leu Leu Ile Phe Asn Val Ser Asn Gln Thr Gly Gly Phe Tyr Leu
                    85                  90                  95

Cys Gln Pro Gly Leu Pro Ser Glu Lys Ala Trp Gln Pro Gly Trp Thr
                100                 105                 110

Val Ser Val Glu Gly Ser Gly Glu Leu Phe Arg Trp Asn Val Ser Asp
                115                 120                 125

Leu Gly Gly Leu Gly Cys Gly Leu Lys Asn Arg Ser Ser Glu Gly Pro
130                 135                 140

Ser Ser Pro Ser Gly Lys Leu Asn Ser Ser Gln Leu Tyr Val Trp Ala
145                 150                 155                 160

Lys Asp Arg Pro Glu Met Trp Glu Gly Glu Pro Val Cys Gly Pro Pro
                165                 170                 175

Arg Asp Ser Leu Asn Gln Ser Leu Ser Gln Asp Leu Thr Met Ala Pro
                180                 185                 190

Gly Ser Thr Leu Trp Leu Ser Cys Gly Val Pro Pro Asp Ser Val Ser
                195                 200                 205

Arg Gly Pro Leu Ser Trp Thr His Val Arg Pro Lys Gly Pro Lys Ser
210                 215                 220

Ser Leu Leu Ser Leu Glu Leu Lys Asp Asp Arg Pro Asp Arg Asp Met
225                 230                 235                 240

Trp Val Val Asp Thr Gly Leu Leu Leu Thr Arg Ala Thr Ala Gln Asp
                245                 250                 255

Ala Gly Lys Tyr Tyr Cys His Arg Gly Asn Trp Thr Lys Ser Phe Tyr
                260                 265                 270

Leu Glu Ile Thr Ala Arg Pro Ala Leu Trp His Trp Leu Leu Arg Ile
                275                 280                 285

Gly Gly Trp Lys Val Pro Ala Val Thr Leu Thr Tyr Leu Ile Phe Cys
                290                 295                 300

Leu Cys Ser Leu Val Gly Ile Leu Gln Leu Gln Arg Ala Leu Val Leu
305                 310                 315                 320

Arg Arg Lys Arg Lys Arg Met Thr Asp Pro Thr Arg Arg Phe Phe Lys
                325                 330                 335

Val Thr Pro Pro Pro Gly Ser Gly Pro Gln Asn Gln Tyr Gly Asn Val
                340                 345                 350

Leu Ser Leu Pro Thr Pro Thr Ser Gly Leu Gly Arg Ala Gln Arg Trp
                355                 360                 365

Ala Ala Gly Leu Gly Gly Thr Ala Pro Ser Tyr Gly Asn Pro Ser Ser
370                 375                 380

Asp Val Gln Val Asp Gly Ala Val Gly Ser Arg Ser Pro Pro Gly Ala
385                 390                 395                 400

Gly Pro Glu Glu Glu Gly Glu Gly Tyr Glu Glu Pro Asp Ser Glu
                405                 410                 415

Glu Gly Ser Glu Phe Tyr Glu Asn Asp Ser Asn Phe Gly Gln Asp Gln
                420                 425                 430

Leu Ser Gln Asp Gly Ser Gly Tyr Glu Asn Pro Glu Asp Glu Pro Leu
                435                 440                 445

Gly Pro Glu Asp Glu Asp Ser Phe Ser Asn Ala Glu Ser Tyr Glu Asn
450                 455                 460

Glu Asp Glu Glu Leu Thr Gln Pro Val Ala Arg Thr Met Asp Phe Leu
465                 470                 475                 480

Ser Pro His Gly Ser Ala Trp Asp Pro Ser Arg Glu Ala Thr Ser Leu
                485                 490                 495
```

```
Gly Ser Gln Ser Tyr Glu Asp Met Arg Gly Leu Leu Tyr Ala Ala Pro
            500                 505                 510

Gln Leu Arg Thr Ile Arg Gly Gln Pro Gly Pro Asn His Glu Glu Asp
            515                 520                 525

Ala Asp Ser Tyr Glu Asn Met Asp Asn Pro Asp Gly Pro Asp Pro Ala
            530                 535                 540

Trp Gly Gly Gly Arg Met Gly Thr Trp Ser Ala Arg
545                 550                 555
```

<210> SEQ ID NO 10
<211> LENGTH: 556
<212> TYPE: PRT
<213> ORGANISM: Homo sapiens

<400> SEQUENCE: 10

```
Met Pro Pro Pro Arg Leu Leu Phe Phe Leu Leu Phe Leu Thr Pro Met
1               5                   10                  15

Glu Val Arg Pro Glu Pro Leu Val Val Lys Val Glu Glu Gly Asp
            20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
            130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
            210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
```

```
              305                 310                 315                 320
Arg Lys Arg Lys Arg Met Thr Asp Pro Thr Arg Arg Phe Phe Lys Val
                      325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
        370                 375                 380

Val Gln Ala Asp Gly Ala Leu Gly Ser Arg Ser Pro Pro Gly Val Gly
385                 390                 395                 400

Pro Glu Glu Glu Glu Gly Gly Tyr Glu Glu Pro Asp Ser Glu Glu
                405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
        450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
                500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
        530                 535                 540

Gly Gly Gly Gly Arg Met Gly Thr Trp Ser Thr Arg
545                 550                 555

<210> SEQ ID NO 11
<211> LENGTH: 558
<212> TYPE: PRT
<213> ORGANISM: Felis catus

<400> SEQUENCE: 11

Met Pro Pro Pro Leu Leu Leu Phe Phe Leu Leu Phe Leu Thr Pro Glu
1               5                   10                  15

Gly Val Arg Pro Gln Lys Thr Leu Leu Val Glu Ala Lys Glu Gly Gly
                20                  25                  30

Lys Ala Glu Leu Pro Cys Leu Lys Gly Pro Ser Asp Gly Pro Pro Glu
            35                  40                  45

Gln Gln Ala Trp Phe Gln Gly Ala Gln Ser Glu Leu Asp Pro Gly Ser
        50                  55                  60

Gln Gly Leu Gly Ile Gln Lys Gly Pro Leu Gly Gln Leu Leu Ile
65                  70                  75                  80

Phe Asn Val Ser Asp Gln Met Gly Gly Phe Tyr Val Cys Gln Leu Gly
                85                  90                  95

Pro Pro Ser Glu Gln Ala Trp Gln Ser Gly Trp Thr Val Thr Val Glu
                100                 105                 110

Gly Ser Gly Glu Leu Phe Arg Trp Asn Ala Ser Tyr Leu Asn Asp Pro
            115                 120                 125
```

```
Gly Cys Gly Leu Gly Asn Arg Ser Ser Glu Gly Pro Lys Pro Ser Ser
        130                 135                 140

Gly Tyr Pro Thr Ser Ser Gln Leu Tyr Val Trp Ala Lys Gly His Pro
145                 150                 155                 160

Glu Ile Trp Glu Thr Asp Pro Asp Cys Ala Ser Pro Arg Gly Gly Leu
                165                 170                 175

Asp Gln Ser Leu Asn Gln Asp Val Thr Val Ala Pro Gly Ser Thr Phe
            180                 185                 190

Trp Leu Pro Cys Glu Val Pro Pro Ala Ser Val Ala Arg Gly Pro Ile
        195                 200                 205

Ser Trp Thr Leu Val Arg Pro Lys Lys His Asn Ile Ser Leu Leu His
210                 215                 220

Leu Asn Leu Arg Glu Asp Ala Pro Val Arg Glu Met Trp Val Leu Asp
225                 230                 235                 240

Thr Leu Arg Gly Gly Ala Val Leu Leu Leu Pro Gln Ala Thr Ala Gln
                245                 250                 255

Asp Ala Gly Thr Tyr His Cys Tyr His Gly Asn Met Thr Ile Glu Met
                260                 265                 270

Gln Leu Lys Val Thr Ala Gln Ser Ala Val Arg His Trp Leu Leu Glu
            275                 280                 285

Ala Gly Gly Trp Lys Val Pro Val Pro Leu Leu Tyr Leu Ile Ile
        290                 295                 300

Cys Leu Gly Ser Leu Val Ser Phe Val His Leu Arg Arg Ala Leu Ile
305                 310                 315                 320

Leu Arg Lys Lys Arg Lys Arg Met Thr Asp Pro Thr Arg Arg Phe Phe
                325                 330                 335

Lys Val Thr Pro Ser Pro Gly Ser Gly Ala Gln Asn Gln Tyr Gly Asn
                340                 345                 350

Val Leu Ser Leu Pro Thr Pro Thr Ser Gly Thr Gly Arg Ala Leu Arg
            355                 360                 365

Trp Ala Ala Gly Leu Gly Ala Ala Val Gln Ser Tyr Gly Asn Pro Arg
        370                 375                 380

Ser Asp Val Gln Glu Val Gly Ala Ala Gly Pro Arg Ser Pro Pro Pro
385                 390                 395                 400

Ala Gly Pro Glu Glu Glu Gly Glu Ala Tyr Glu Glu Pro Asp Ser
                405                 410                 415

Glu Glu Gly Ser Glu Phe Tyr Glu Asn Asp Ser Asn Leu Gly Gln Asp
            420                 425                 430

Gln Leu Ser Gln Asp Gly Ser Gly Tyr Glu Asn Pro Glu Asp Asp Ala
        435                 440                 445

Leu Gly Pro Gly Asp Glu Asp Ser Phe Ser Ser Ala Glu Ser Tyr Glu
450                 455                 460

Asn Glu Asp Glu Glu Leu Ala Gln Pro Val Ala Arg Thr Ala Asp Phe
465                 470                 475                 480

Leu Ser Pro His Gly Ser Ala Trp Asp Pro Ser Arg Glu Ala Thr Ser
                485                 490                 495

Leu Gly Ser Gln Ser Tyr Glu Asp Met Arg Gly Ile Leu Tyr Ala Ala
            500                 505                 510

Pro Gln Leu Arg Ser Leu Arg Ala Gln Pro Gly Pro Asn His Glu Glu
        515                 520                 525

Asp Ala Asp Ser Tyr Glu Asn Met Asp Asn Pro Asn Gly Pro Glu Pro
530                 535                 540

Ala Trp Gly Gly Gly Gly Arg Met Gly Thr Trp Ser Thr Arg
```

```
545                 550                 555
```

<210> SEQ ID NO 12
<211> LENGTH: 555
<212> TYPE: PRT
<213> ORGANISM: Heterocephalus glaber

<400> SEQUENCE: 12

```
Met Pro Pro Leu Leu Leu Ser Phe Leu Leu Phe Leu Phe Pro Lys
1               5                   10                  15

Gly Gly Arg Pro Gln Lys Pro Leu Leu Val Glu Val Gln Glu Gly
            20                  25                  30

Asp Ala Val Leu Pro Cys Leu Arg Gly Pro Ser Ser Ala Arg Ser Glu
        35                  40                  45

Pro Leu Val Trp Ser Arg Gly Asn Gln Ser Ala Pro Phe Leu Glu Leu
    50                  55                  60

Ser Leu Gly Leu Pro Gly Leu Gly Val Gln Met Gly Pro Leu Gly Ile
65                  70                  75                  80

Leu Leu Leu Ile Phe Asn Val Ser Asp Gln Met Gly Gly Phe Tyr Leu
                85                  90                  95

Cys Gln Arg Gly Pro Pro Ser Lys Asn Ala Trp Gln Pro Gly Trp Thr
            100                 105                 110

Val Ser Val Glu Gly Ser Gly Lys Leu Phe Arg Trp Asn Ala Ser Asp
        115                 120                 125

Leu Gly Asp Leu Ser Cys Gly Pro Gly Asn Gly Ser Ser Gly Arg Pro
    130                 135                 140

Arg Leu Ala Pro His His Arg Asn Asn Ser Gln Leu Tyr Val Trp Asn
145                 150                 155                 160

Lys Gly His Pro Glu Ile Trp Glu Ala Glu Pro Gly Cys Ala Pro Ser
                165                 170                 175

Arg Gly Ser Leu Lys Glu Ser Leu Thr Gln Asp Phe Thr Val Ala Pro
            180                 185                 190

Gly Ser Thr Leu Trp Leu Ser Cys Gly Ala Pro Pro Thr His Val Thr
        195                 200                 205

Arg Gly Pro Ile Ser Trp Thr Gln Val His Pro Lys Lys Pro Asn Thr
    210                 215                 220

Thr Leu Leu Asn Leu Tyr Leu Arg Glu Lys Pro Pro Val Gln Lys Met
225                 230                 235                 240

Trp Val Leu Gly Pro Val Leu Ser Leu Ser Gln Ala Thr Val Gln Ala
                245                 250                 255

Ser Gly Thr Tyr Tyr Cys Leu Arg Gly Asn Leu Thr Thr Glu Ile His
            260                 265                 270

Met Lys Val Ile Pro Arg Pro Val Ala Trp His Trp Leu Leu Arg Asn
        275                 280                 285

Gly Gly Trp Lys Ile Pro Val Val Pro Leu Ala Tyr Leu Ala Phe Cys
    290                 295                 300

Leu Gly Ser Leu Val Ala Phe Leu His Ile Arg Ala Leu Val Leu
305                 310                 315                 320

Arg Arg Lys Arg Lys Arg Met Thr Asp Pro Thr Arg Arg Phe Phe Lys
                325                 330                 335

Val Thr Pro Pro Pro Gly Lys Gly Thr Gln Ser Gln Tyr Gly Asn Val
            340                 345                 350

Leu Ser Leu Pro Thr Pro Thr Ser Gly Thr Gly Arg Ala Gln Arg Trp
        355                 360                 365
```

```
Ala Ala Ala Leu Gly Gly Thr Val Gln Pro Tyr Gly Asn Pro Arg Gly
        370                 375                 380

Asp Val Gln Glu Ala Gly Ala Ala Gly Pro Arg Ser Pro Pro Thr Ala
385                 390                 395                 400

Gly Pro Glu Glu Glu Gly Glu Ala Tyr Glu Glu Pro Asp Ser Glu
                405                 410                 415

Glu Gly Ser Glu Phe Tyr Glu Asn Asp Ser Ser Leu Gly Arg Asp Arg
                420                 425                 430

Leu Ser Arg Asp Gly Ser Gly Tyr Glu Asn Pro Glu Asp Ala Pro Ser
            435                 440                 445

Gly Pro Ala Asp Asp Ser Phe Ser Asn Ala Glu Ser Tyr Glu Asn
        450                 455                 460

Ala Asp Glu Glu Met Ala Pro Pro Ala Ala Arg Thr Thr Asp Phe Leu
465                 470                 475                 480

Ser Pro His Gly Ser Ala Arg Asp Pro Ser Arg Glu Ala Thr Ser Leu
                485                 490                 495

Gly Ser Gln Ser Tyr Glu Asp Met Arg Gly Ile Leu Tyr Ala Ala Pro
            500                 505                 510

Gln Leu Arg Ser Leu Gln Pro Gly Pro His Gln Glu Glu Asp Ala Asp
            515                 520                 525

Ser Tyr Glu Asn Met Asp Asn Pro Asp Glu Pro Glu Leu Ala Trp Gly
530                 535                 540

Gly Gly Gly His Met Gly Val Trp Ser Thr Arg
545                 550                 555

<210> SEQ ID NO 13
<211> LENGTH: 536
<212> TYPE: PRT
<213> ORGANISM: Cavia porcellus

<400> SEQUENCE: 13

Met Pro Pro Pro Leu Leu Leu Ser Phe Leu Leu Phe Leu Phe Pro Lys
1               5                   10                  15

Gly Val Arg Pro Gln Lys Pro Leu Leu Val Glu Val Glu Glu Gly Gly
                20                  25                  30

Asp Ala Val Leu Pro Cys Leu Arg Gly Pro Ser Thr Ala Pro Ser Glu
            35                  40                  45

Gln Leu Val Trp Ser Arg Gly Asn Gln Ser Ala Pro Phe Leu Glu Leu
        50                  55                  60

Asn Leu Gly Leu Pro Asp Leu Gly Ile His Thr Gly Pro Leu Gly Ile
65                  70                  75                  80

Leu Leu Leu Ile Phe Asn Val Ser Asp Lys Met Gly Gly Phe Tyr Leu
                85                  90                  95

Cys Gln Pro Gly Pro Pro Ser Lys Asn Ala Trp Gln Pro Gly Trp Thr
                100                 105                 110

Val Ser Val Glu Gly Ser Gly Glu Leu Phe Arg Trp Asn Ser Ser Asp
            115                 120                 125

Leu Gly Asp Phe Ser Cys Gly Pro Gly Asn Gly Ser Ser Glu Gly Pro
        130                 135                 140

Thr Ser Gln Leu Tyr Val Trp Asp Lys Arg Asp Ser Pro Ser Trp Glu
145                 150                 155                 160

Pro Glu Pro Val Cys Ala Pro Pro Arg Gly Ser Leu Asn Glu Asn Leu
                165                 170                 175

Thr Gln Asp Leu Thr Val Ala Leu Gly Ser Thr Leu Trp Leu Ser Cys
            180                 185                 190
```

Gly Val Pro Pro Ala His Val Thr Arg Gly Pro Val Ser Trp Thr Gln
            195                 200                 205

Val His Pro Lys Lys Pro Asp Ser Thr Leu Leu Ser Leu Tyr Leu Arg
    210                 215                 220

Glu Lys Pro Pro Val Gln Glu Met Trp Val Leu Gly Pro Val Leu Ser
225                 230                 235                 240

Leu Ser Gln Val Thr Val Gln Ala Ala Gly Thr Tyr Tyr Cys Leu Arg
                245                 250                 255

Gly Asn Leu Thr Thr Glu Ile His Met Lys Val Thr Ala Arg Gln Ala
            260                 265                 270

Val Trp His Trp Leu Leu Arg Ser Gly Gly Trp Lys Val Pro Ala Val
    275                 280                 285

Ser Leu Val Tyr Leu Ile Phe Cys Leu Gly Ser Leu Val Val Phe Leu
290                 295                 300

Gln Ile Arg Lys Ala Leu Val Leu Arg Arg Lys Arg Met Thr
305                 310                 315                 320

Asp Pro Asn Arg Arg Phe Phe Lys Val Thr Pro Pro Ser Gly Asn Gly
            325                 330                 335

Thr Pro Asn Gln Tyr Gly Asn Val Leu Ser Leu Pro Thr Pro Gly Arg
    340                 345                 350

Thr Gln Arg Trp Ala Ala Ala Leu Gly Gly Thr Ile Gln Ser Tyr Gly
                355                 360                 365

Asn Ser Arg Ser Asp Val Gln Glu Thr Gly Ala Met Gly Ser Arg Ser
            370                 375                 380

Pro Thr Thr Ala Glu Glu Gly Glu Gly Tyr Glu Gly Pro Asp Ser
385                 390                 395                 400

Glu Glu Gly Ser Glu Phe Tyr Glu Asn Asp Ser Asn Arg Gly Gln Asp
                405                 410                 415

Gln Leu Ser Gln Asp Ala Ser Gly Tyr Glu Asn Pro Glu Asp Gly Pro
            420                 425                 430

Leu Gly Ser Ala Asp Glu Asp Ser Phe Ser Asn Glu Ser Tyr Glu Asn
    435                 440                 445

Ala Asp Glu Glu Leu Ala Gln Pro Val Ala Arg Thr Thr Asp Phe Leu
450                 455                 460

Ser Pro His Gly Ser Ala Trp Asp Pro Ser Arg Glu Ala Thr Ser Leu
465                 470                 475                 480

Gly Ser Gln Ser Tyr Glu Asp Met Arg Gly Ile Leu Tyr Ala Ala Pro
                485                 490                 495

Gln Leu Arg Ser Leu Gln Pro Gly His His Glu Asp Ala Asp
            500                 505                 510

Ser Tyr Glu Asn Met Asp Asn Pro Asp Glu Pro Glu Pro Ala Trp Gly
    515                 520                 525

Gly Gly Gly His Met Gly Ile Trp
530                 535

<210> SEQ ID NO 14
<211> LENGTH: 572
<212> TYPE: PRT
<213> ORGANISM: Sus scrofa

<400> SEQUENCE: 14

Met Pro Pro Pro Leu Leu Leu Phe Ser Leu Leu Phe Ser Phe Phe
1                   5                   10                  15

Leu Thr Pro Val Glu Ala Arg Pro Gln Glu Pro Tyr Leu Val Glu Ala

```
            20                  25                  30
Gln Glu Gly Gly Asn Ala Val Leu Pro Cys Leu Glu Gly Pro Ser Glu
            35                  40                  45

Gly Pro Pro Glu Gln Leu Ala Trp Phe Arg Gly Ser Gln Ser Thr Pro
        50                  55                  60

Phe Leu Glu Leu Ser Leu Gly Leu Pro Gly Leu Gly Ile His Val Gly
 65                  70                  75                  80

Pro Leu Gly Thr Leu Lys Glu Pro Gln Gly Thr Leu Leu Phe Ile Phe
                85                  90                  95

Asn Val Ser Asp Gln Met Gly Gly Phe Tyr Leu Cys Gln Gln Gly Pro
            100                 105                 110

Pro Leu Asp Gln Ser Trp Gln Pro Gly Trp Thr Val Asn Val Lys Gly
            115                 120                 125

Ser Gly Glu Leu Phe Arg Trp Asn Ala Ser Asp Leu Asn Asp Pro Ser
        130                 135                 140

Cys Asp Leu Gly Ala Arg Ser Ser Glu Gly Arg Arg Ser Ser Ser Ser
145                 150                 155                 160

His Pro Thr Arg Ser Lys Leu Tyr Val Trp Ala Lys Asn Gln Ala Lys
                165                 170                 175

Val Leu His Thr Asp Leu Thr Cys Pro Pro Asn Ser Thr Val Asn
            180                 185                 190

Gln Ser Asn Ser His Asp Leu Thr Val Ala Pro Gly Ser Thr Leu Ser
            195                 200                 205

Leu Ser Cys Gly Ser Ser Arg Ala Ser Leu Val Arg Gly Pro Ile Ser
        210                 215                 220

Trp Ile His Val Arg Pro Lys Lys His Val Lys Leu Leu Ser Leu Asn
225                 230                 235                 240

Leu Thr Glu Asp Ala Gln Leu Arg Glu Met Trp Val Met Gly Ser Leu
                245                 250                 255

Arg Gly Lys Ala Val Leu Leu Leu Pro Glu Ala Thr Ala Gln Asp Ala
            260                 265                 270

Asp Thr Tyr His Cys Asn His Gly Asn Val Thr Thr Gln Met Arg Leu
            275                 280                 285

Lys Val Thr Ala Arg Ser Val Trp His Trp Leu Leu Glu Thr Gly Gly
            290                 295                 300

Trp Gln Val Pro Val Val Thr Leu Val Tyr Leu Ile Phe Cys Leu Gly
305                 310                 315                 320

Ser Leu Val Gly Phe Leu His Leu Arg Arg Ala Leu Ile Leu Arg Arg
                325                 330                 335

Lys Arg Lys Arg Met Thr Asp Pro Thr Arg Arg Phe Phe Lys Val Thr
            340                 345                 350

Pro Pro Pro Gly Asn Gly Ala Gln Asn Gln Tyr Gly Asn Val Leu Ser
            355                 360                 365

Leu Ser Thr Pro His Ser Gly Thr Gly Arg Ala Leu Arg Trp Ala Ala
            370                 375                 380

Gly Leu Gly Ala Ala Val Pro Ser Tyr Gly Asn Pro Arg Ser Asp Val
385                 390                 395                 400

Gln Glu Ala Arg Ala Ala Gly Ser Arg Ser Pro Pro Gly Thr Gly Pro
            405                 410                 415

Glu Glu Glu Glu Gly Glu Ala Tyr Glu Glu Pro Asp Ser Glu Glu Gly
            420                 425                 430

Ser Glu Phe Tyr Glu Asn Asp Ser Asn Leu Gly Arg Asp Gln Leu Ser
            435                 440                 445
```

```
Gln Asp Gly Ser Asn Tyr Glu Asn Pro Glu Glu Gly Val Leu Gly Pro
    450                 455                 460

Glu Asp Glu Asp Ser Phe Ser Asn Ala Ala Glu Ser Tyr Glu Asn Glu
465                 470                 475                 480

Asp Glu Glu Leu Val Gln Pro Val Ala Arg Thr Thr Asp Phe Leu Ser
                485                 490                 495

Pro His Gly Ser Ala Trp Asp Pro Ser Arg Glu Ala Thr Ser Leu Gly
            500                 505                 510

Ser Gln Ser Tyr Glu Asp Met Arg Gly Ile Leu Tyr Ala Ala Pro Gln
            515                 520                 525

Leu Arg Ser Phe Arg Gly Gln Pro Gly Pro Asn His Glu Glu Asp Ala
    530                 535                 540

Asp Ser Tyr Glu Asn Met Asp Asn Pro Asp Gly Pro Glu Pro Ala Trp
545                 550                 555                 560

Gly Gly Gly Gly His Met Gly Ala Trp Ser Thr Arg
                565                 570

<210> SEQ ID NO 15
<211> LENGTH: 611
<212> TYPE: PRT
<213> ORGANISM: Canis familiaris

<400> SEQUENCE: 15

Met Glu Lys Gly Thr Gly Gly Val Thr Thr Pro Ser Ser Leu Gly Asp
1               5                   10                  15

Cys Pro Leu Ala Arg Pro His Arg Arg Ser Trp Phe Ser Ala Pro Gln
            20                  25                  30

Ala Pro Ala Cys Pro Ser Ile Pro Cys Ala Ala Lys Leu Gly Ala Pro
        35                  40                  45

Gly Ser Leu Ala Ala Met Pro Pro Leu Leu Leu Phe Phe Leu Leu
    50                  55                  60

Phe Leu Thr Pro Glu Gly Val Arg Pro Gln Glu Thr Leu Gln Val Glu
65                  70                  75                  80

Ala Lys Glu Gly Gly Lys Ala Glu Leu Pro Cys Leu Lys Val Pro Ser
                85                  90                  95

Asp Gly Pro Leu Glu Gln Gln Ala Trp Phe Gln Gly Ala Gln Ser Glu
            100                 105                 110

Leu Gly Leu Trp Ser Gln Gly Leu Gly Val Arg Lys Gly Ser Leu Gly
        115                 120                 125

Ile Gln Leu Phe Val Phe Asn Val Ser Asp Gln Met Gly Gly Phe Tyr
    130                 135                 140

Leu Cys Gln Pro Gly Pro Pro Ser Glu Gln Ala Trp Gln Ser Gly Trp
145                 150                 155                 160

Thr Val Ser Val Glu Gly Ser Gly Glu Leu Phe Arg Trp Asn Ala Ser
                165                 170                 175

Ala Leu Asn Asp Ser Gly Cys Gly Leu Gly Asn Arg Pro Ser Glu Gly
            180                 185                 190

Pro Lys Pro Ser Ser Arg Tyr Pro Thr Ser Ser Gln Leu Tyr Val Trp
        195                 200                 205

Glu Lys Asp His Pro Glu Ile Trp Glu Thr Asp Pro Glu Cys Ala Leu
    210                 215                 220

Pro Arg Gly Thr Leu Asn Gln Ser Leu Asn Gln Asp Leu Ile Val Ala
225                 230                 235                 240

Pro Gly Ser Thr Phe Trp Leu Pro Cys Glu Val Pro Pro Ala Phe Val
```

```
                         245                 250                 255
Ala Arg Gly Pro Ile Ser Trp Thr His Val Arg Pro Lys Lys His Asn
            260                 265                 270

Ile Ser Leu Leu Ser Leu Asp Leu Arg Glu Asp Ala Pro Gly Arg Glu
            275                 280                 285

Met Trp Val Leu Gly Thr Leu Ser Gly Gly Ala Val Leu Leu Leu Pro
            290                 295                 300

Gln Ala Thr Val Arg Asp Ala Gly Thr Tyr Arg Cys Tyr His Gly Asn
305                 310                 315                 320

Arg Thr Val Glu Met Gln Leu Lys Val Ile Ala Gln Ser Val Arg Tyr
                325                 330                 335

Trp Leu Leu Glu Thr Gly Gly Trp Lys Val Pro Ala Val Pro Leu Leu
            340                 345                 350

Tyr Leu Ile Phe Cys Leu Gly Ser Leu Val Ser Phe Leu His Leu Arg
            355                 360                 365

Arg Ala Leu Ile Leu Arg Arg Lys Arg Lys Met Thr Asp Pro Thr
            370                 375                 380

Arg Arg Phe Phe Lys Val Thr Pro Pro Gly Ser Gly Ala Gln Asn
385                 390                 395                 400

Gln Tyr Gly Asn Val Leu Ser Leu Pro Thr Pro Thr Ser Gly Thr Gly
                405                 410                 415

Arg Ala Leu Arg Trp Ala Ala Gly Phe Gly Ala Ala Val Gln Ser Tyr
            420                 425                 430

Gly Ser Pro Arg Ser Asp Val Pro Glu Ala Gly Ala Gly Ser Arg
            435                 440                 445

Ser Pro Pro Pro Ala Gly Pro Glu Glu Glu Gly Glu Ala Tyr Glu
450                 455                 460

Glu Pro Asp Ser Glu Glu Gly Ser Glu Phe Tyr Glu Asn Asp Ser Asn
465                 470                 475                 480

Arg Gly Gln Asp Gln Leu Ser Gln Asp Gly Ser Gly Tyr Glu Asn Pro
                485                 490                 495

Glu Asp Glu Ala Leu Gly Pro Glu Asp Glu Asp Ser Phe Ser Ser Ala
            500                 505                 510

Ala Glu Ser Tyr Glu Asn Glu Asp Glu Leu Ala Gln Pro Val Thr
            515                 520                 525

Arg Thr Val Asp Phe Leu Ser Pro Arg Gly Ser Val Trp Asp Pro Ser
            530                 535                 540

Lys Glu Ala Thr Ser Leu Gly Ser Gln Ser Tyr Glu Asp Met Arg Gly
545                 550                 555                 560

Ile Leu Tyr Ala Ala Pro Gln Leu Arg Ser Val Arg Ala Gln Pro Gly
                565                 570                 575

Pro Ser His Glu Glu Asp Ala Asp Ser Tyr Glu Asn Met Asp Asn Pro
            580                 585                 590

Asn Gly Pro Glu Pro Ala Trp Gly Gly Gly Arg Met Ser Thr Trp
            595                 600                 605

Ser Thr Arg
    610

<210> SEQ ID NO 16
<211> LENGTH: 11
<212> TYPE: PRT
<213> ORGANISM: Artificial Sequence
<220> FEATURE:
<223> OTHER INFORMATION: rabbit CD19 gap fill consensus sequence
```

<400> SEQUENCE: 16

Gly Gly Pro Arg Pro Ser Ser Gly His Pro Asn
1               5                   10

<210> SEQ ID NO 17
<211> LENGTH: 34
<212> TYPE: DNA
<213> ORGANISM: Artificial Sequence
<220> FEATURE:
<223> OTHER INFORMATION: rb_5UTR_primer_region1

<400> SEQUENCE: 17
gaagctgggc ggcccgggga gtctggccac catg                               34

<210> SEQ ID NO 18
<211> LENGTH: 64
<212> TYPE: DNA
<213> ORGANISM: Artificial Sequence
<220> FEATURE:
<223> OTHER INFORMATION: rb_5UTR_primer_region2

<400> SEQUENCE: 18
cgcccccaca ggcgtccatg gttcagtgcc cagcaggccc ctgcctgccc cagcatcccc   60
tgcg                                                               64

<210> SEQ ID NO 19
<211> LENGTH: 102
<212> TYPE: DNA
<213> ORGANISM: Artificial Sequence
<220> FEATURE:
<223> OTHER INFORMATION: rb_3UTR_primer_region

<400> SEQUENCE: 19
ctggggctcc tgagacccct gagagccaca cctgactctg aaatctaggg actgcaagca   60
gatggtgtca acctgtggaa cagcattgct caggacgtgt gc                     102

<210> SEQ ID NO 20
<211> LENGTH: 21
<212> TYPE: DNA
<213> ORGANISM: Artificial Sequence
<220> FEATURE:
<223> OTHER INFORMATION: rbCD19 UTR forward primer

<400> SEQUENCE: 20
gcccctgcct gccccagcat c                                             21

<210> SEQ ID NO 21
<211> LENGTH: 31
<212> TYPE: DNA
<213> ORGANISM: Artificial Sequence
<220> FEATURE:
<223> OTHER INFORMATION: rbCD19 UTR reverse primer

<400> SEQUENCE: 21
caatgctgtt ccacaggttg acaccatctg c                                  31

<210> SEQ ID NO 22
<211> LENGTH: 27
<212> TYPE: DNA
<213> ORGANISM: Artificial Sequence
<220> FEATURE:
<223> OTHER INFORMATION: rbCD19 CDS forward primer

<400> SEQUENCE: 22

```
atgccacctc ctctcctgct cgccttc                                          27
```

<210> SEQ ID NO 23
<211> LENGTH: 26
<212> TYPE: DNA
<213> ORGANISM: Artificial Sequence
<220> FEATURE:
<223> OTHER INFORMATION: rbCD19 CDS reverse primer

<400> SEQUENCE: 23

```
acctagtgct ccaggtcccc ccatgg                                           26
```

<210> SEQ ID NO 24
<211> LENGTH: 234
<212> TYPE: PRT
<213> ORGANISM: Mus musculus

<400> SEQUENCE: 24

```
Met Val Ser Thr Ser Gln Leu Leu Gly Leu Leu Leu Phe Trp Thr Ser
1               5                   10                  15

Ala Ser Arg Cys Asp Ile Val Met Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Ile Ser Asp Phe Leu His Trp Tyr Gln Gln Ser Ser His Glu Ser Pro
    50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Ser Asp Phe Thr Leu Thr Ile Asn
                85                  90                  95

Ser Val Glu Pro Glu Asp Val Gly Val Tyr Tyr Cys Gln Asn Gly His
            100                 105                 110

Ser Phe Pro Tyr Thr Phe Gly Gly Gly Thr Asn Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Pro Thr Ser Pro
    210                 215                 220

Ile Val Lys Ser Phe Asn Arg Asn Glu Cys
225                 230
```

<210> SEQ ID NO 25
<211> LENGTH: 20
<212> TYPE: PRT
<213> ORGANISM: Mus musculus

<400> SEQUENCE: 25

```
Met Val Ser Thr Ser Gln Leu Leu Gly Leu Leu Leu Phe Trp Thr Ser
1               5                   10                  15

Ala Ser Arg Cys
```

20

<210> SEQ ID NO 26
<211> LENGTH: 107
<212> TYPE: PRT
<213> ORGANISM: Mus musculus

<400> SEQUENCE: 26

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Phe
            20                  25                  30

Leu His Trp Tyr Gln Gln Ser Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Thr Ile Asn Ser Val Glu Pro
65                  70                  75                  80

Glu Asp Val Gly Val Tyr Tyr Cys Gln Asn Gly His Ser Phe Pro Tyr
                85                  90                  95

Thr Phe Gly Gly Gly Thr Asn Leu Glu Ile Lys
            100                 105

<210> SEQ ID NO 27
<211> LENGTH: 102
<212> TYPE: PRT
<213> ORGANISM: Mus musculus

<400> SEQUENCE: 27

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Pro Thr Ser
                85                  90                  95

Pro Ile Val Lys Ser Phe
            100

<210> SEQ ID NO 28
<211> LENGTH: 463
<212> TYPE: PRT
<213> ORGANISM: Mus musculus

<400> SEQUENCE: 28

Phe Leu Phe Leu Leu Ser Ile Ile Ala Gly Val His Cys Gln Val Gln
1               5                   10                  15

Leu Gln Gln Ser Gly Pro Glu Val Val Lys Pro Gly Ala Ser Val Arg
            20                  25                  30

Met Ser Cys Lys Ala Ser Gly Tyr Ile Phe Thr Asn His Tyr Ile His
        35                  40                  45

Trp Met Lys Gln Arg Pro Gly Gln Gly Leu Glu Trp Val Gly Cys Ile
    50                  55                  60

```
Tyr Pro Gly Asn Val Asn Ser Asn Tyr Asn Glu Lys Phe Lys Gly Lys
 65                  70                  75                  80

Ala Thr Leu Thr Ala Asp Lys Ser Ser Thr Ala Tyr Leu Gln Leu
                 85                  90                  95

Ser Ser Leu Thr Ser Glu Asp Ser Ala Val Tyr Phe Cys Ala Arg Gly
                100                 105                 110

Gly Tyr Tyr Gly Ser Ser Tyr Ser Trp Phe Ala Tyr Trp Gly Gln Gly
                115                 120                 125

Thr Leu Val Ile Val Ser Ala Ala Lys Thr Thr Ala Pro Ser Val Tyr
            130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Gly Val His Thr Phe Pro Ala Val Leu
                180                 185                 190

Gln Ser Asp Leu Tyr Thr Leu Ser Ser Ser Val Thr Val Thr Ser Ser
            195                 200                 205

Thr Trp Pro Ser Gln Ser Ile Thr Cys Asn Val Ala His Pro Ala Ser
210                 215                 220

Ser Thr Lys Val Asp Lys Lys Ile Glu Pro Arg Gly Pro Thr Ile Lys
225                 230                 235                 240

Pro Cys Pro Pro Cys Lys Cys Pro Ala Pro Asn Leu Leu Gly Gly Pro
                245                 250                 255

Ser Val Phe Ile Phe Pro Pro Lys Ile Lys Asp Val Leu Met Ile Ser
                260                 265                 270

Leu Ser Pro Ile Val Thr Cys Val Val Val Asp Val Ser Glu Asp Asp
            275                 280                 285

Pro Asp Val Gln Ile Ser Trp Phe Val Asn Asn Val Glu Val His Thr
290                 295                 300

Ala Gln Thr Gln Thr His Arg Glu Asp Tyr Asn Ser Thr Leu Arg Val
305                 310                 315                 320

Val Ser Ala Leu Pro Ile Gln His Gln Asp Trp Met Ser Gly Lys Glu
                325                 330                 335

Phe Lys Cys Lys Val Asn Asn Lys Asp Leu Pro Ala Pro Ile Glu Arg
                340                 345                 350

Thr Ile Ser Lys Pro Lys Gly Ser Val Arg Ala Pro Gln Val Tyr Val
            355                 360                 365

Leu Pro Pro Glu Glu Met Thr Lys Lys Gln Val Thr Leu Thr
370                 375                 380

Cys Met Val Thr Asp Phe Met Pro Glu Asp Ile Tyr Val Glu Trp Thr
385                 390                 395                 400

Asn Asn Gly Lys Thr Glu Leu Asn Tyr Lys Asn Thr Glu Pro Val Leu
                405                 410                 415

Asp Ser Asp Gly Ser Tyr Phe Met Tyr Ser Lys Leu Arg Val Glu Lys
                420                 425                 430

Lys Asn Trp Val Glu Arg Asn Ser Tyr Ser Cys Ser Val Val His Glu
                435                 440                 445

Gly Leu His Asn His His Thr Thr Lys Ser Phe Ser Arg Thr Pro
                450                 455                 460

<210> SEQ ID NO 29
<211> LENGTH: 13
```

```
<212> TYPE: PRT
<213> ORGANISM: Mus musculus

<400> SEQUENCE: 29

Phe Leu Phe Leu Leu Ser Ile Ile Ala Gly Val His Cys
1               5                   10

<210> SEQ ID NO 30
<211> LENGTH: 122
<212> TYPE: PRT
<213> ORGANISM: Mus musculus

<400> SEQUENCE: 30

Gln Val Gln Leu Gln Gln Ser Gly Pro Glu Val Val Lys Pro Gly Ala
1               5                   10                  15

Ser Val Arg Met Ser Cys Lys Ala Ser Gly Tyr Ile Phe Thr Asn His
            20                  25                  30

Tyr Ile His Trp Met Lys Gln Arg Pro Gly Gln Gly Leu Glu Trp Val
        35                  40                  45

Gly Cys Ile Tyr Pro Gly Asn Val Asn Ser Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Leu Gln Leu Ser Ser Leu Thr Ser Glu Asp Ser Ala Val Tyr Phe Cys
                85                  90                  95

Ala Arg Gly Gly Tyr Tyr Gly Ser Ser Tyr Ser Trp Phe Ala Tyr Trp
            100                 105                 110

Gly Gln Gly Thr Leu Val Ile Val Ser Ala
        115                 120

<210> SEQ ID NO 31
<211> LENGTH: 328
<212> TYPE: PRT
<213> ORGANISM: Mus musculus

<400> SEQUENCE: 31

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
```

```
                165                 170                 175
Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro
                325

<210> SEQ ID NO 32
<211> LENGTH: 7
<212> TYPE: PRT
<213> ORGANISM: Mus musculus

<400> SEQUENCE: 32

Gly Tyr Ile Phe Thr Asn His
1               5

<210> SEQ ID NO 33
<211> LENGTH: 5
<212> TYPE: PRT
<213> ORGANISM: Mus musculus

<400> SEQUENCE: 33

Asn His Tyr Ile His
1               5

<210> SEQ ID NO 34
<211> LENGTH: 10
<212> TYPE: PRT
<213> ORGANISM: Mus musculus

<400> SEQUENCE: 34

Gly Tyr Ile Phe Thr Asn His Tyr Ile His
1               5                   10

<210> SEQ ID NO 35
<211> LENGTH: 6
<212> TYPE: PRT
<213> ORGANISM: Mus musculus

<400> SEQUENCE: 35

Tyr Pro Gly Asn Val Asn
1               5

<210> SEQ ID NO 36
<211> LENGTH: 17
```

```
<212> TYPE: PRT
<213> ORGANISM: Mus musculus

<400> SEQUENCE: 36

Cys Ile Tyr Pro Gly Asn Val Asn Ser Asn Tyr Asn Glu Lys Phe Lys
1               5                   10                  15

Gly

<210> SEQ ID NO 37
<211> LENGTH: 13
<212> TYPE: PRT
<213> ORGANISM: Mus musculus

<400> SEQUENCE: 37

Gly Gly Tyr Tyr Gly Ser Ser Tyr Ser Trp Phe Ala Tyr
1               5                   10

<210> SEQ ID NO 38
<211> LENGTH: 11
<212> TYPE: PRT
<213> ORGANISM: Mus musculus

<400> SEQUENCE: 38

Arg Ala Ser Gln Ser Ile Ser Asp Phe Leu His
1               5                   10

<210> SEQ ID NO 39
<211> LENGTH: 7
<212> TYPE: PRT
<213> ORGANISM: Mus musculus

<400> SEQUENCE: 39

Tyr Ala Ser Gln Ser Ile Ser
1               5

<210> SEQ ID NO 40
<211> LENGTH: 9
<212> TYPE: PRT
<213> ORGANISM: Mus musculus

<400> SEQUENCE: 40

Gln Asn Gly His Ser Phe Pro Tyr Thr
1               5

<210> SEQ ID NO 41
<211> LENGTH: 107
<212> TYPE: PRT
<213> ORGANISM: Homo sapiens

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95
```

Pro Val Thr Lys Ser Phe Asn Arg Gly Glu Cys
            100                 105

<210> SEQ ID NO 42
<211> LENGTH: 105
<212> TYPE: PRT
<213> ORGANISM: Homo sapiens

<400> SEQUENCE: 42

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 43
<211> LENGTH: 330
<212> TYPE: PRT
<213> ORGANISM: Homo sapiens

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 44
<211> LENGTH: 330
<212> TYPE: PRT
<213> ORGANISM: Homo sapiens

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 45
<211> LENGTH: 330
<212> TYPE: PRT
<213> ORGANISM: Homo sapiens

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 330
<212> TYPE: PRT
<213> ORGANISM: Homo sapiens

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 47
<211> LENGTH: 327
<212> TYPE: PRT
<213> ORGANISM: Homo sapiens

<400> SEQUENCE: 47

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 48
<211> LENGTH: 327
<212> TYPE: PRT
<213> ORGANISM: Homo sapiens

<400> SEQUENCE: 48

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 49
<211> LENGTH: 327
<212> TYPE: PRT
<213> ORGANISM: Homo sapiens

<400> SEQUENCE: 49

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Gly Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 50
<211> LENGTH: 107
<212> TYPE: PRT
<213> ORGANISM: Mus musculus

<400> SEQUENCE: 50

Arg Ala Asp Ala Ala Pro Thr Val Ser Ile Phe Pro Pro Ser Ser Glu
 1               5                  10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
 50                  55                  60

Thr Tyr Ser Met Ser Ser Thr Leu Thr Leu Thr Lys Asp Glu Tyr Glu
 65                  70                  75                  80
```

-continued

```
Arg His Asn Ser Tyr Thr Cys Glu Ala Thr His Lys Thr Ser Thr Ser
                 85                  90                  95

Pro Ile Val Lys Ser Phe Asn Arg Asn Glu Cys
            100                 105

<210> SEQ ID NO 51
<211> LENGTH: 324
<212> TYPE: PRT
<213> ORGANISM: Mus musculus

<400> SEQUENCE: 51

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 52
<211> LENGTH: 36
```

```
<212> TYPE: PRT
<213> ORGANISM: Artificial Sequence
<220> FEATURE:
<223> OTHER INFORMATION: GPI anchor

<400> SEQUENCE: 52

Asp Thr Asp Leu Cys Asn Ala Ser Gly Ala His Ala Leu Gln Pro Ala
1               5                   10                  15

Ala Ala Ile Leu Ala Leu Leu Pro Ala Leu Gly Leu Leu Leu Trp Gly
            20                  25                  30

Pro Gly Gln Leu
        35

<210> SEQ ID NO 53
<211> LENGTH: 30
<212> TYPE: DNA
<213> ORGANISM: Artificial Sequence
<220> FEATURE:
<223> OTHER INFORMATION: rabbit 3' UTR CDS primer

<400> SEQUENCE: 53
gcagatggtg tcaacctgtg gaacagcatt                                    30

<210> SEQ ID NO 54
<211> LENGTH: 21
<212> TYPE: DNA
<213> ORGANISM: Artificial Sequence
<220> FEATURE:
<223> OTHER INFORMATION: rabbit 5' UTR primer

<400> SEQUENCE: 54 gccccctgcct gccccagcat c                                            21

<210> SEQ ID NO 55
<211> LENGTH: 19
<212> TYPE: PRT
<213> ORGANISM: Mus musculus

<400> SEQUENCE: 55

Met Gly Trp Ser Cys Ile Ile Leu Phe Leu Val Ala Thr Ala Thr Gly
1               5                   10                  15

Val His Ser

<210> SEQ ID NO 56
<211> LENGTH: 20
<212> TYPE: PRT
<213> ORGANISM: Oryctolagus cuniculus

<400> SEQUENCE: 56

Met Pro Pro Pro Leu Leu Leu Ala Phe Leu Leu Phe Leu Thr Leu Gly
1               5                   10                  15

Arg Val Arg Pro
        20
```